(12) United States Patent
Ji et al.

(10) Patent No.: US 7,071,309 B2
(45) Date of Patent: Jul. 4, 2006

(54) ANTIBODIES TO BREAST SPECIFIC GENE 1

(75) Inventors: Hongjun Ji, San Diego, CA (US);
Craig A. Rosen, Laytonsville, MD (US)

(73) Assignee: Human Genome Sciences, Inc., Rockville, MD (US)

(*) Notice: Subject to any disclaimer, the term of this patent is extended or adjusted under 35 U.S.C. 154(b) by 544 days.

(21) Appl. No.: 10/267,849

(22) Filed: Oct. 10, 2002

(65) Prior Publication Data

US 2003/0087824 A1    May 8, 2003

Related U.S. Application Data

(63) Continuation of application No. 08/673,284, filed on Jun. 28, 1996, now abandoned.

(60) Provisional application No. 60/000,602, filed on Jun. 30, 1995.

(51) Int. Cl.
*C07K 16/00* (2006.01)
(52) U.S. Cl. ..................... 530/387.1; 435/7.1
(58) Field of Classification Search ............. 530/387.1, 530/350
See application file for complete search history.

(56) References Cited

U.S. PATENT DOCUMENTS 5,525,501 A    6/1996    Tokuyama

FOREIGN PATENT DOCUMENTS

EP    0 908 727 A1    4/1999

OTHER PUBLICATIONS

Bowie et al, Science, 1990, 247:1306-1310.*
Herbert et al, The Dictionary of Immunology, Academic Press, 3rd Edition, London, 1985, pp. 58-59.*
Ahn et al., "The structural and functional diversity of dystrophin," Nature Genetics 3(4):283-291 (1993).
Albert, B. (ed.). Molecular Biology of the Cell, 3rd Edition, p. 403. 1996.
Allred et al., "HER-2/neu in Node-Negative Breast Cancer: Prognostic Significance of Overexpression Influenced by the Presence of In Situ Carcinoma," J. Clin. Oncol. 10(4):599-605 (1992).
Angerer et al., "In situ hybridization to cellular RNA with radiolabelled RNA probes," in: In situ hybridization: a practical approach, Wilkinson, D.G., ed., IRL Press at Oxford University Press, Oxford and New York; pp. 15-32 (1992).
Bergh et al., "Complete sequencing of the p53 gene provides prognostic information in breast cancer patients, particularly in relation to adjuvant systemic therapy and radiotherapy," Nature Med. 1(10):1029-1034 (1995).
BIO Report. "Critical Synergy: The Biotechnology Industry and Intellectual Property Protection", pp. 75, 100-107; Oct. 17, 1994.
Bork et al., "Powers and pitfalls in sequence analysis," Genome Research 10:398-400 (2000).
Branch, A. "A hitchhiker's guide to antisense and nonantisense biochemical pathways,", Hepatology 24:1517-1529 (1996).
Broaddus et al., "Strategies for the design and delivery of antisense oligonucleotides in central nervous system", Methods in Enzymology 314:121-135 (2000).
Burgess et al., "Possible dissociation of the heparin-binding and mitogenic acitivies of heparin-binding growth factgor-1 from its receptor-binding activities by site-directed mutagenesis of a single lysine residue," J. Cellular Biology, vol. 111 (1990).
Cawthon et al., "cDNA sequence and genomic structure of EV12B, a gene lying within an intron of theneurofibromatosis Type 1 gene," Genomics 9(3):446-460 (1991).
Chen et al., "Differential expression human tissue factor in normal mammary epithelial cells and in carcinomas," Mol. Med. 1(2):153-160 (1995).
Donohue et al., "Human Hydroxyindole-O-Methyltransferase: presence of LINE-1 fragment in a cDNA clone and pineal mRNA," DNA and Cell Biology 12:715-727, Mary Ann Liebert, Inc. Publishers (1993).

(Continued)

*Primary Examiner*—Jeffrey Siew
*Assistant Examiner*—Laura Goddard
(74) *Attorney, Agent, or Firm*—Human Genome Sciences, Inc.

(57) ABSTRACT

Human breast specific gene polypeptides and DNA (RNA) encoding such polypeptides and a procedure for producing such polypeptides by recombinant techniques is disclosed. Also disclosed are methods for utilizing such polynucleotides or polypeptides as a diagnostic marker for breast cancer and as an agent to determine if breast cancer has metastasized. Also disclosed are antibodies specific to the breast specific gene polypeptides which may be used to target cancer cells and be used as part of a breast cancer vaccine. Methods of screening for antagonists for the polypeptide and therapeutic uses thereof are also disclosed.

16 Claims, 14 Drawing Sheets

OTHER PUBLICATIONS

Elledge et al., "The role and prognostic significance of p53 gene alterations in breast cancer," Breast Cancer Res. Treatment 27(1/2):95-102 (1993).

Ernster et al., "Incidence of and treatment for ductal carcinoma in situ of the breast," JAMA 275(12):913-918 (1996).

Ferno et al., "Cathepsin D, both a prognostic factor and a predictive factor for the effect of adjuvant tamoxifen in breast cancer," Eur. J. Cancer 30A(14):2042-2048 (1994).

Foekens et al., "Urokinase-type plasminogen activator and its inhibitor PAI-1: Predictors of poor response to tamoxifen therapy in recurrent breast cancer," J. Natl. Cancer Inst. 87(10):751-756 (1995).

Fritsch et al., "A soluble immunoglobulin variable domain without a disulfide bridge . . . ", Biol. Chem. Hoppe-Seyler, vol. 375:363-356 (1994).

Futreal et al., "BRCA1 mutations in primary breast and ovarian carcinomas," Science 266:120-122 (1994).

Gasparini et al., "Evaluating the potential usefulness of new prognostic and predictive indicators in node-negative breast cancer patients," J. Natl. Cancer Inst. 85(15):1206-1219 (1993).

Gasparini et al., Erratum: "Evaluating the potential usefulness of new prognostic and predictive indicators in node-negative breast cancer patients," J. Natl. Cancer Inst. 85(19):1605 (1993).

Geneseq Accession No. AAQ61427, "Human brain Expressed Sequence Tag EST01420", released Mar. 16, 1994.

GENBANK Accession No. H11372, "ym13a05.s1 Soares infant brain 1NIB Homo sapiens cDNA clone IMAGE:47522 3' similar to SP:S21265 S21265; Acetylserotonin N-Methyltransferase;, mRNA sequence," released Jun. 26, 1995.

GENBANK Accession No. M79265, "EST01420 Whole Brain, Clontech mRNA, Ruben Moreno Homo sapiens cDNA clone HRBAA27, mRNA sequence," released May 26, 1992.

GENBANK Accession No. M83779, "Homo sapiens (clone 179 or 217) hydroxyindole-O-methyltransferase (HIOMT) mRNA, complete cds." (1993).

Goldhirsch et al., "Meeting highlights: International consensus panel on the treatment of primary breast cancer," J. Natl. Cancer Inst. 87(19):1441-1445 (1995).

Gusterson et al., "Prognostic importance of c-erbB-2 expression in breast cancer," J. Clin. Oncol. 10(7):1049-1056 (1992).

Harris et al., "Polycystic kidney disease 1: Identification and analysis of the primary defect," J. Am. Soc. Nephrology 6:1125-1133 (1995).

Harris et al., "Breast cancer angiogenesis: therapy target and prognostic factor," Eur. Cancer 31A(5):831-832 (1995).

Hayes, D.F. "Tumor markers for breast cancer current utilities and future prospects," Hematology—Oncology Clinics of North America, W.B. Saunders, ed. 8(3):485-506 (1994).

Ji et al., "Identification of a breast cancer-specific gene, BCSG1, by direct differential cDNA sequencing," Cancer Research 57(4):759-764 (1997).

Kim et al., "Restoring allosterism with compensatory mutations in hemoglobin," PNAS 91:11547-11551 (1994).

Klijn et al., "Prognostic factors and response to therapy in breast cancer," Cancer Surveys 18:165-198 (1993).

Lavedan et al., "Identification, localization and characterization of the human gamma-synuclein gein," Human Genetics 103(1):106-112 (1998).

Lazar et al., "Transforming growth factor alpha: Mutation of aspartic acid 47 and leuine 48 results in different biological activities," Molecular and Cellular Biology 8:1247-1252 (1988).

Liang et al., "Differential display and cloning of messenger RNAs from human breast cancer versus mammary epithelial cells," Cancer Res. 52(24):6966-6968 (1992).

Lu et al., "Molecular mechanisms for aberrant expression of the human breast cancer specific gene 1 in breast cancer cells: control of transcription by DNA methylation and intronic sequences", Oncogene 20(37):5173-5185 (2001).

Manning et al., "Differential expression of oestrogen regulated genes in breast cancer," Acta Oncologica 34(5):641-646 (1995). Presented at the 5th Scandinavian Breast Cancer Symposium, Reykjavik, Iceland, 1994.

Miki et al., "A strong candidate for the breast and ovarian cancer susceptibility gene BRCA1," Science 266:66-71 (1994).

Matthews et al., Biochemistry, 2nd ed., The Benjamin/Cummings Publishing Co., Inc., Menlo Park, CA; pp. 165-171 (1996).

Matthews, B., "Genetic and Structural analysis of the protein stability problem, " In Perspectives in Biochemistry, vol. 1, pp. 6-9 (1989).

Porter-Jordan et al., "Overview of the biologic markers of breast cancer," Hematol.. Oncol. Clin. North Am. 8(1):73-100 (1994).

Sager et al., "Identification by differential display of alpha 6 integrin as a candidate tumor suppressor gene," FASEB J. 7(10):964-970 (1993).

Sambrook et al. Molecular Cloning: A Laboratory Manual, 2nd Edition, 1989, pp. 10.27-10.28.

Schena et al., "Quantitative monitoring of gene expression patterns with a complementary DNA microarray," Science 270:467-470 (1995).

Steeg et al., "Nm23 and breast cancer metastasis," Breast Cancer Res. Treatment 25(2):175-187 (1993).

Velculescu et al., "Serial analysis of gene expression," Science 270:484-487 (1995).

Watson et al., "Isolation of differentially expressed sequence tags from human breast cancer," Cancer Res. 54(17):4598-4602 (1994).

Wooster et al., "Localization of a breast cancer susceptibility gene, BRCA2, to chromosome 13q12-13," Science 265:2088-2090 (1994).

Wu et al., "Stage-specific expression of breast cancer-specific gene 'gammal-synuclen", Cancer Epidemiology Biomarkers and Prevention, 12(9):920-925 (2003).

Zhang et al., "Differential expression of elafin in human normal mammary epithelial cells and carcinomas is regulated at the transcriptional level," Cancer Res. 55(12):2537-2541 (1995).

Zou et al., "Maspin, a serpin with tumor-suppressing activity in human mammary epithelial cells," Science 263:526-529 (1994).

* cited by examiner

FIG. 1

BSG1 (assembly sequence)

```
GCCGCTGCGGCAGACTCGAGCCAGCTCAAGCCCGCAGCTCGCAGGGAGAT
CCAGCTCCGTCCTGCAGCAGCMCAACCCTGCACACCACCATGGAT
GTYTTCAAGAAGGGCTTCTCCATCGCCAAGGAGGGCGTGGGTGCGGTG
GAAAAGACCAAGCAGGGGGTGAGCAGCTGAGAAGACCAAGGAGGGG
GGTCATGTATGTGGGAGCCAAGACCAAGGAGAATGTTGTATACAGAGCGT
GACCTCAGTGCCGAGAAGACCAAGGAGCAGGCCAACGCCGTGAGCAAGG
CTGTGGTGAGCACGTCAACACTKTGGCCACCAAGACCGTKGAGGAGGCGG
AGAACATCGCGGTCAMCTCCGGKTGKTGCGCAAGGAGGAYTKAGGCCAT
YTKCCCCCAACAGGAGGGTGAGGCATCMARAGAGGGCTACAGGCCAGCTTGGAT
MRAKKRGGMSCAGAGTGGGAGACTAGAGAGGGCTACACCAGGCCAGCTTGGAT
GACCTGAAGAGCGCTCCTCGCCTTGAGTGGACACCATCCCCTCCTAGCACAAG
GAGTGCCCGCTTTGAGTGGACATGCGGCTGTCCMACGTTCCTGCCCTCGT
TTCCCTGGGCCAMCCCTTGGCCTGTCCAACTTTTGCTGTTGCAACCAAMCTTA
ATTGCCTTCCTTGGAATTTTTTAAAAKGATTTCAAATWAAATTGGCCCATTT
GTTGTTGTGAAAAAAAAAAAAAA
TTTAAAAAAAAAAAAA
```

FIG. 2

BSG2 (HBGBP46)

```
AGACCCACTTCCAACCCCGGACCCCGAGCAGTGCAGATCCACTTGCAGCAGTTGACTT
 T  H  F  Q  P  P  G  P  P  Q  Q  C  R  S  T  S  Q  Q  V  T  F

TTTCAGGACCCCTCCCCAGCGCTGAGCTGAGTCTGTGCCGATCTGCATGANT
 S  G  T  P  S  P  A  L  S  C  X  V  L  C  R  I  L  H  X  W

GGCCAGAGACAAGTCCACAGTTACTCAGCAGGTCCGAGAGTCCTGCAGNCAGGGC
 P  D  D  K  V  H  K  L  L  S  R  V  A  E  S  C  X  Q  G  P

CGGCCTGCTGCTGGTGGAGAGCTCTGATGAGGAGAAGAGGGTGCCAGGCCTNGN
 A  C  C  W  R  R  S  W  M  R  R  R  G  W  R  S  A  X  X

ATGCAGTCACTGAACATGCTGAGGTCAAGGCAAGAGCGAGCTNGGCGAGTTGTTC
 A  V  T  E  H  A  G  A  D  *  R  Q  E  R  S  X  A  S  F  Q

AGTGTTGNTGGAGNTNCAAGGTTTCCACCAGTTGCAAGTTGTTGCATTNGGGGGTT
 C  L  X  E  X  Q  G  F  P  P  V  A  S  C  C  I  X  G  G  F

TTTCCTGGATGNCCNTTNGGCCACAAATTGCCGTTNAAGGNCNGNAGTTTTTA
 S  W  M  X  X  X  A  T  K  L  P  V  X  R  X  X  X  F  F  N

ATTTNGGGGTTTNCTTCCCAGTTNAAGTTGGANCCCNGTTCNAAGTTCCTT
 F  X  G  F  X  F  P  R  F  X  V  G  X  P  V  X  K  V  P  L

TGGGNGATTTA
 G  D  L
```

BSG3 (HBGDQ94) FIG. 3

```
AGCNGNCTCTTCACCATCCGTTTTCCAGCAAGAGTCGTTCACCAGACAGGTGTTATGGA
 S  X  L  F  T  I  P  F  S  S  K  S  R  S  P  D  R  C  Y  G

AGCTGTGAAGTTGTGAAAATTCGGAGAAGTGATTTCTTACCAGCAATTAGCAGCCTG
 S  C  *  R  L  *  K  F  G  E  V  I  S  Y  Q  Q  L  A  A  L

GNAGGCAACCCAAGCCGCCCGACCAGTTGGACGAGCAATGAGAGCAATCTGTCC
 X  G  N  P  K  A  A  R  A  V  G  R  S  N  E  R  Q  S  C  P

CATCCTCATCCGTCCACAGAGTGTNCAGCAGGACCGTGGCAACTTACTTC
 H  P  H  P  V  P  Q  S  V  L  X  A  A  X  P  W  A  T  Y  F

CGGAGGACTGGCCGTGAAAGGAATGCCTTCTGGCCATGAAAGGCCACCGGTTTGGGAAG
 R  R  T  G  R  E  R  N  G  F  W  P  M  K  G  H  R  F  G  K

CCAAGNTTTGGAGGAAGCTTCAGTTTTGGCAAGGCCTGANTTCAAGGAGCCGGNGNT
 P  X  F  G  G  S  F  R  F  W  Q  G  P  G  F  K  G  A  G  X

ACCTTCGGGGNNCCCGNCTTTTTGCNGNAAATTNNTTTTTTTTNCATTAGGNTGCNTTT
 T  F  G  X  X  R  L  F  G  R  K  X  X  F  X  H  *  X  G  F

TTTTNGCNCAAAAAAGNTTAAATTNNATTGGTTTGGCGNNTTGNGNACCCTTTTTT
 F  X  P  Q  K  X  F  K  X  X  W  F  G  X  L  X  X  P  F  F

TAAGGAAGTTG
 *  G  S
```

FIG. 4

BSG4 (HBGDA42)

GAGGGACCCGCCGACCACCACCAGCTGCGCTCACTGACTGGCTCATCGAAACCTGTNTC
G T A D H H Q L R S L T G L I R N L X R

GGAACGTTAGAACAAGGACGAGATGTCCACGAGAAGTGAGCCACCTGATCGAGAAGC
N A R N K D E M S T K V V S H L I E K L

TGCCGGGCAGGGTGGGTGAGAAGTCGCCCAGCGAAGTCGCCCAGAGTCTGTCAACATCATAGCTG
P G S V G E K S P P A E V L V N I I A V

TGCTCAACAACCTGGTCGTGGCCAGCCCCATCNTGCCCGAGACCTGCTGTATTTGACG
L N N L V V A S P I X A R D L L Y F D G

GACTCCGAAAGCTCATCTTCATCAAGAAGAAGCGGGACAGCCCGACTTAGAAGTNCT
L R K L I F I K K K R D S P D S * K X S

CCCGGGCAGCATCAGCCTCCTGCNACAACAGTTGGCANTACAACAAGTTCCACCGTGAT
R A A S S L L X N L L A X Q Q V P P * F

TTCCGGNGAAGGTTTTGGAAGAGAGATTTCGGGCCTTAGTGAAGCTTTTNGAGG
P G E G F S E G G F L G P * V K L X E E

AGAGGTGACGTNGNCANGNCAGGAGGACAGATTANTTCAGTTTTTGACCCAGCTTGNG
R * R X P X X G T D X F S F W T Q L X X

NGAGGTATT
R Y

FIG. 5

BSG5 (HBGBP36)

```
AGCCCAGCCCCAGCCTGCCGGAGCCCACGGAGCTACCTCTACCTCCACTC
CTGCCACCGCGCCGCCCTCGACCACCGCCCTNTCCCCATCCGTCCCC
NCTCAGGGNACCAAGAAGTTNCAAGAGGGGCCGTGCGTGCCAGGCGC
TAGGGAAGCCGGGTGGGTGAGGGTAGCCCCTTGAGCCCTGTCCCTGCGG
CTGTNAAGAGAGCAGCAGGNACCCTGGGCCAGTTCCAGAGACCTGGGGTGT
GTTTGGGGGTGTGGGGTGTGAGTNCGTATGAAATGTGTTTGCTGGGGCAA
TTGTGCCCTGGAATCATGGGCAGGTNGGNCCGNTCCGGNNANGGNCCGGG
NTTNAAATTNTTCCGTGGAAGNTTTAAGGGTTGAATTTANGGTAAAAACC
TTNGGGGAAGGGAAGNTTTCCAAGGCAAAAAGGTTT
```

FIG. 6

BSG6 (HBNBF70)

```
AGACTCCCCGCTGGTACCCCCTGTGGTGCTTGGCTCTTGGTGAATCATGGATGCCCTGAA
 D  S  P  A  G  Y  P  P  V  A  G  S  A  *  I  M  D  A  L  N
CAGCCTTGCCACGGACTCGCCTTGTGGGATCCCCAAGATGTGNAAGACCAGCCTG
 S  L  A  T  D  S  P  C  G  I  P  P  K  M  W  X  D  Q  P  *
ACCCTCGCCGTGTCTGCGGCCCATCCAAGGCCGCTCCTGCCACATCTACCCGG
 P  L  A  G  V  C  R  P  I  Q  G  R  P  A  S  P  H  L  P  G
CCGTGAGTTCTGGGCCCTCGGAAGCAGNGANGNGAGAAACTCGGCTCCAGAATCC
 R  G  V  P  G  A  L  R  S  X  X  X  G  E  T  R  L  Q  N  P
ATCCTGGTGTTCGACCTGANTCCTTNCATTTGAGTGGCCGTTGTTCANTCATTNAGTTT
 S  C  W  F  R  P  L  G  P  S  R  W  C  L  P  F  P  S  A  A
ATCCCAGTGACTGNATCCCCTTNCATTNCATTGAGTGGCCGTTGTTCANTCATTNAGTTT
 S  Q  *  L  X  P  S  X  H  L  S  G  R  C  S  X  H  X  G  F
TAAGGAGTTGNGNTTGAGNTGCAGCAAGNCAAGNCAAATTAACGGGNCCATTNTGAGAAAAA
 K  E  L  X  X  E  V  Q  P  X  Q  I  N  G  X  H  X  E  K  K
GGAANCNAGGGTTTTAAAATTNCAATTGGGCAACTTTGGTTTANTTCATGTTAANGNA
 E  X  R  V  L  K  X  X  Q  L  G  Q  L  W  F  X  S  W  L  X  X
AAAAAGTTTGG
 K  S  L
```

FIG. 7

BSG7 (HBGBF39)

```
GCAGCAGCTGGACATCGAGGGCGAGCTGCGCCGGCTCATGGCCAAGCCCG
AGGCTCTGAAGTCACTGCAGGCGGGAGCAGGCAGGAGCTGCTGGAG
CANTACGTGAGCACCGTGAACNACCGCAGTGTACATCGTGGACTCGCTGGA
CGAGGACCGGCTCCGGGAACAAGAGGAGGATCAGATGCTGCGGGACATG
ATTNAGAAAGCTGGGCTGGCCTCCAGAGGAAGAAGTTCCAAGTTCCGTTTGTTCC
AAGATCTTGGTCACCAAAAGCAAAAGCAAAAGCAGCCCCTTCCCANTNGTTAGCC
CATTAGGGCCCTTGGGTTTTGGCCCGNAACCTTGGGAATTCCGGTTTTGGA
NTTTGGGGGGNCCATGGNTTTTGGCCCNNACCCGGAAACCCGGTTTT
TAATTNGGGGNCCCTNGGTTTTTGGNNCGNNACCNNGAATNTTTGGGTT
TTTNGNTTTGGNNAAGGGNTTT
```

FIG. 8

BSG8 (HBGBU61)

AGGTCATCGGGCAGCCTTCCCTGTGTGCCAAGCCAGCNTTCGCTTCTGAAA
ACCAAACTCCAGCCTGCCAGTCGGGACTTGGTCGCCCGGCGCTGCCAG
AATGNTCCACTGNCNACCGGNCCCCCTGCCTCGGTTTCCCTTCTGTTTAGT
GGCGACACAGGCACCCAGCTTTGGGGTGGTGCTGAGCGCTCCCAGGGGTGC
CAGGAGCCACTGGGACANGGGTGAGGNTCCCAGACGTTCCTTGAGGTGC
CCAGTTNTCCAGGGAGNTTCTGGGCCCAAGGCGTNTTNAGGGATCTTGTTC
CTTTAAACNNNNCCAATTG

FIG. 9

BSG9 (HBGCA96)

ACGAGAACAGANGATAGAGGGCATCTNTCCCAGGTGACCNTNCTNTTCTGT
CCCAGGAGGGTGGGTAATTCCCTNNGGGATGGGGCTCCCACACCTNCNTN
AGTCCCCACTCAGACCAGCACCAGTGTCTGCCTCTGAGAATGTTGGCAGC
TCACAGAGAGCAGGCCGNCCGGGATGGGGCAGGTACTCCCCACCTT
CCTGCNTNCGATCCTANTTCTNATCCAGCGTCCNCTTATTACCGTTTTNA
CTAATGCTTCTNTNGAGNANNGCTCTTTGGAAGNAGGAGCNNNAGCNTNNT
GGAGCNTCNCANGAGATGTTAAGGNTTATTAAGCTT

BSG10 (HBGDM44)

FIG. 10

ACATTGGTGTATGTNCTTGGCTGAGGTCTACTTGGCTTGCCTGCTTGATCC
TGAGAGNCACCCACCCATCTCACAGTGAATAGGTTGGCAGGTGTGGGCTG
GCGGGTGGACTACACCCTGNAGCTCCAGCCTGCTGCAATCCGTGGAAGAG
NCCATGGTGCACCTGCGCGCTGGAGGTGGCAGCTGCCCCAGGGACCCCAGN
CCAGCCTGTTGCCATGTCCCTCTCAGCAGACAATTCCAGGTNCTCCTGGCA
GAACTGAAGNAGGNCCAGACCCTGATGAGCTCCTGGGTGAGGAGAAGGG
TGTTTCCAGGCCTNTTGGGAGCCGNCTTGCCCGTATGGAGTTAAGGCCTTT
GAATTGTTTTGGCTGGGGAGGNAACCTGGNTTTAAGGTNNTNAAGNCCTTGCC
CGNATTTTCCAAATTNCCANTTGNNNAAATTTTTTTNNGAATTTGNTT
AAGGTTTGGGACTTTT

BSG11 (HBGBC21)

FIG. 11

AGCATTGTGGGTAAAGGCCTGGAGGCAGGAAAGTGAAGGACAATTTCAAGAA
ACTCNGTTCATCNGTTCATCAACACCTTCCTGGGCCATGCCTGGGTACTG
AGGAACCCAGCCTGAATCTGGACATCATTTCCCTTTCAGAGCATAGAATG
CAGGGGGATCCAGGATGGGTTAACAGGAGNGAAGCTTGGTTCAAGGAGAC
CTTTGCGCACGACAGGNTTCCTACCTGGGGNTAANTTGGGGAGGTTTANGCAGGGN
GAGCACGACAGGNTTCCTACCTGGGGNTAANTTGGGGAGGTTTANGCAGGGN
NTGTTGCCATCCGTAGNTCCNCGGNTAANTTGGGAGGTTTANGCAGGGN
GAATNGGTTTTGAACCCNGNGNGTTGGGGTTNGCAATTGNNGNTNNGNT
GNGAACCATTGAATNNGNGNGGCTTNGGTGNTCCAGGTTGGGATCCNNTTNN
AAAAAAAAAAAAATT

FIG. 12

BSG12 (HBGDN07)

GAGACGCACTCTCTAGCCCGGCAGATGAAGGCGANGGCGGGCGGCCGNACT
TGGATGAGATTCACCGCGAGCTGCGNCCTCAGGGATCCGCACGACCCCAG
CCCGACCCAAACGCCGAGTTCGACCCCGACCTGCCAGGGGCGGCCTGC
ACCGCTGTCTGGNCTGCGCGAGGTACTTCATCGATTCCACCAACCTGAAGA
CCCACTTCCGATCCAAAGACCACAAGAAAAAGGCTGAAGCAGCTTGAGCGTC
GAGCCCTTACAGTCAGGAAGAGGCGGAGAGGGCAGCGGGGTTATTGGGATT
CTATGTGNCCCCCCAGGNGGNTGGCAGTGCCCACGAAGTTTTCCATTGA
GGTNCCTNAGATTGGNTAACTTTTANCTGAAAATGGGCTTNAAGTTNCAAGG
NAAAAGGANTTNCCCCTGGGCAATTACGAAAGNTTAGTTNGGNAGGGAGGT
TTCAACCCTTTTNCCTTTGGTTTGGG

FIG. 13

BSG13 (HBGBD14)

AGGCACAGCTGTTGCGTCAGGCAAGGTCACCTGCATTTATTGAGCAGC
AGTNCTGTNTCAGGCCCAGGGCCGAGCCCTCTCCCTGTTCCCTATGGT
GTCTCCGAGGCCCTCTGGGAGGGCCNCACATCTGGGAGCAGCACCTCAGA
GTGGNACAGAAAGCATTAGCGTGCCACGAGCTTCACCCGACGCCGAGCCT
GTNAAGGTGGGCTGATGGTGCCCGTTTTAACCCAGCGCTTCAGGGAGGTTC
AGAATGGNAGCCGAAACCAGGGGNTGTTNAGCATCANCTTCTGGGAGNCC
TTTTNTACTTTTTATGGACTGGTTCCTAGGGTTNGGGGGCCTGTTTTNNCATTCNA
CANGNAGGCTTGGNGTTCCTTTAGGGTTNGGGGGCCTGTTTTNNCATTCNA
ACCCAAGCTTTTTNNNTTNCATTNNCTTNNTTTTTNGGGNGGCNAGTAAANN
GNTCCAAGGTTTTTT

FIG. 14

BSG14 (HBGBF11)

GGGCCACAGCTGCTCCTGCGCCTGGCCTTACTTCCTACCGAGACTTCCTG
GGCACCAACTGTCCAGCTCAGCTGCCTGGCTGNGACANAAGNTGACCAC
CGACTGGGGTGACACGCAGGCCTATCTGGCGACCCACTGGGGGTGGGGC
GCTGCACTAGCCACAGCCGATGGACTTCCTTGTTTCCTGCGCGCTCCCG
GCAGGTGGGCTGAGGCCCCTGGGCTGGGACGTAACTGGTGGGCAAC
CTGAGCCTCAGGTGGAACCTGNNCGTTGGTTTNAACCTGNAGGCAAGNCCT
TGTTTNTTGGGGAATTGNCNNAAAATNGNGGACCAATGNTTGGNCNNAGCC
ANTTGNCCGATTTTATNNTNCCAATTGAAAGTTNGNATTTTTGGNGGAAA
NTTNGNGGAAGGAATTTAACTTNGANNGGGGGGGGNACCCGANNGGGCCAAA
GGGGTTTAAAANGAATTTTTG

FIG. 15

BSG15 (HBNAC96)

AGCCCACTCTGAGCTCCCACGAGAAACACTGCTTCTCCAGGCCCGGGTTGT
TGGGGAGAGGCAGAGGCAGCTGGAGCGCCGTNTCTCTCCTGCTGGGGA
CAACGTTTGGGCTTTGGGGCTATTGACTGAGTGGCTGACAGTTATCTTTGCAACC
CCAAACTGGCTTTGGGGCCAGGACAAGGGTNGGCNTTTATGGTGGTCCAA
GTTTNNNTNCTTNCCNAACTNGGGNTTGNTCCNTGACTGTTGGANCNTGTTA
ATTGGCTNTTTCANTGGGTTTTATTTT

FIG. 16

BSG16 (HBGDH36)

CCCCGTTCGCCCCCTGCAAGCGCGCCCGCTTCGAGGACTTCTGCCCGGAC
TCGTCCCCGGAGCGTCCAACATCTCAAACTTGATCTCCATCTTTGGCTCCGG
CTTCTCGGGGCTGTGTGAGCGNACAGCCGGACTCCTCGGAGCAGCCGCCG
CCGCTCAACGGCAGCTGTGCGCCAAGCAGGCGTNCGCCAGCCTCGGCG
CCTGGNACTCGAGCCATTGTNGCCTTCTAGGGACCCCGAGGGGCACAGG
GGACCNGGGCCCCGNGGAACGAGNGGGGGNCCAGACAAAGATTTGGNAAAGG
GGCGAGAGGAGGAACGAGNGGGGGNCAATTGGGGGTTAATTTG
GNNNNAANGGGNNNAANNGNTNTTTTTTTAAATTNTTAAAAAAAAAA
AAAATTTTGGGGGGG

FIG. 17

BSG17 (HBGDD46)

AGTNTCATACCGCCAACCACCGCTGGCTGGGAGGAGTCGGAGNTGAGAAC
CTACACAGAGGTGGTGACAGAGTTGGGACCGAGGTTGGAGCCCGANTTTGG
GACCAAGGTGGAGCCCNGAGTTGGAGCCCAGTTGGAGACCTGANTTGAGAC
CCAGCTGGAACCCACTGAGTTTNAGGAAGAGGAGGAGAAAGAGGAGG
AGATAGCCACTGGCCAGGCATTCCCTTCACAACAGTAGAGACCTACACAG
TGAACTTTTGGGGACTTTTGAGATCANNGTCCTACCAGACCCCAGNCCAAN
TTNAGGTTTNAGCAGCAGGATTT

FIG. 18

BSG18 (HBNAI20)

AGGGCAGAAGCCATGGCCCATGTNTGCACATCCAGGGAGGAGGACAGAAG
GCCCAGCTCACATGTGAGTCCTGGCAGAAGCCATGGCCCATGTNTGCACAT
CCAGGGAGGAGGACAGAAGCCCAGCTCACATGTGAGTNCCTGGNCAGAA
GCCATGGCCCATGTTTGCACATCCAGGGAGGAGGACAGAAGCCCAGCTCA
CATGTGAGTTCCTGGCAGAGAAGCCATGGCCCATGTTTGCACATCCAGGGAGG
AGGACAGAAGGNCCAGNTCAGTGGCCCCTGGCCCCGNCAANTTNTANGNCCG
ANCAGNAGGGTAGNTAGNCTNTTNTTGGNGTGTGTTCCAATTCCGTATTTNG
GTNGGTTTTGGGGNCCANTCAANAATTGGTTTGGGGTNNTTNTTTNNNT
TAATTAAAGTTTTAACTNNAAAAAAAAATTNGGGGGGNTTNGNAT
TTTTTNNTTTGGGGGGTTTAAATTNNNCAAGTGAAATGTNTTAAATTTT
G

FIG. 19

BSG19 (HBNAI67)

AGGNGCCCTCCTGAGCAAGATCCACCTGTACACACGCGGCTGCCACAGCG
ACCAGAGCCTTAGCCATCTGTNTGTCACTGAAGCAGAGATGCTCAGGGACC
CAGAGGTAGGCCAGCAACTGCTGCGGCGGTGAGCGTGAGAACCAGCG
CCTGGAGGCTGTCCTGGCGTGGCGGCCAAGGCTGAGCTGTCCTGGCGGAN
GCAGGCCGNGCCGGCCTNGGAGGCAAGGCTTGAGGCTGTTGACGGGGCCAA
ANTTGAGTNTACAANATTTTNGNAGCNAAAAGTTGGCCCCGNCCAANCCCAT
GGAGNTNTACAANATTTTGTTANAAGGNAAGNTTTGGGNAAAAGGGACCGGA
NGGCAAAACGTTTGTTATTNAAAACCTTTAGGGNCCANAGNTTNTTNGNG
CTTGGGAAATTTTGTTATTNAAAACCTTTAGGGNCCANAGNTTNTTNGNG
GGTTTAATNGGTTTAAAGGCAATTTTGAAA

FIG. 20

BSG20 (HBGDQ22)

CANGCNTNTCCANGACCNTGGACCTCNCCTGGCCAGNCTGGANACCNNCATCGTCCCTATCAGTGGAGTNGCNTTACANGGCACTNGCGCGTCGANNTACATCGCCNGGNNNNNTATCCATNTNAACTGATGCTGGNGCATCAAACCCGCAGCTGTTCGCGCTTATGGGCACCCGGGCACCGGNGCAGGCATCGCCAGGAAGCTGGAGCTNGTGGAGCAGCAGTNTCGGCTGGAGCAGCAGTGCGGCAGAGCTGCAGAGCAGNAACCAGGGCCACTGGGCTGACTGNCTACAGCGTACAGAGCCCGGTTGGACAAGGACCTGGAA

SEQUENCE LISTING

<160> NUMBER OF SEQ ID NOS: 45

<210> SEQ ID NO 1
<211> LENGTH: 786
<212> TYPE: DNA
<213> ORGANISM: Homo sapiens

<400> SEQUENCE: 1

```
gccgctgcgg cagactcgag ccagctcaag cccgcagctc gcagggagat ccagctccgt    60
cctgcctgca gcagcmcaac cctgcacacc caccatggat gtyttcaaga agggcttctc   120
catcgccaag gagggcgtgg tgggtgcggt ggaaaagacc aagcaggggg tgacggaagc   180
agctgagaag accaaggagg gggtcatgta tgtgggagcc aagaccaagg agaatgttgt   240
atgtacagag cgtgacctca gtggccgaga agaccaagga gcaggccaac gccgtgagca   300
aggctgtggt gagcagcgtc aacactktgg ccaccaagac cgtkgaggag gcggagaaca   360
tcgcggtcam ctccgggktg ktgcgcaagg aggayttkag gccatytkcc cccaacagga   420
gggtgaggca tcmaragara rgakwgsaag wggcmrakkr ggmscagagt gggggagact   480
agagggctac aggccagctt ggatgacctg aagagcgctc ctctgccttg ggacaccatc   540
ccctcctagc acaaggagtg cccgctttga gtggacatgc ggctgtcccm acgttcctgc   600
cctcgttttc cctgggccam ccttggcctg tccaactgtg ctgttgcaac caamcttaat   660
tgccttcctt gggccccaac caacttttg gttctttttg amcccattta tgtttgttgt   720
gaattttttt tttaaaakga tttcaaatwa aaatttgggc ccatttttta aaaaaaaaa   780 aaaaaa                                                             786
```

<210> SEQ ID NO 2
<211> LENGTH: 549

-continued

```
<212> TYPE: DNA
<213> ORGANISM: Homo sapiens

<400> SEQUENCE: 2
ggcacgagcc cacttccaac cccccggacc gcaggcagtg cagatccact tcgcagcagg     60
tgactttttc agggaccccc tccccagcgc tgagctgtac gtcctgtgcc ggatcctgca    120
tgactggcca gacgacaaag tccacaagtt actcagcagg gtcgccgaga gctgcaagcc    180
aggggccggc ctgctgctgg tggagacgct cctggatgag gagaagaggg tggcgcagcg    240
cgccctgatg cagtcactga acatgctggt gcagactgaa ggcaaggagc ggagcctggg    300
cgagtatcag tgcttgctgg agctgcacgg cttccaccag gtgcaggtgg tgcacttggg    360
gggtgtcctg gatgccatct tggccaccaa agtggccccc tgaagcccag gcagcatgtt    420
cattataggg atgtcctccc ccaggctgca ggtggaccgc ccggtcccca agtaccatag    480
gacagtcaca taggagcgtg tagtcgtgac tgaataaaga aagcaaaagc caaaaaaaaa    540
aaaaaaaaa                                                            549

<210> SEQ ID NO 3
<211> LENGTH: 20
<212> TYPE: PRT
<213> ORGANISM: Homo sapiens

<400> SEQUENCE: 3

Gly Thr Ser Pro Leu Pro Thr Pro Arg Thr Ala Gly Ser Ala Asp Pro
1               5                   10                  15

Leu Arg Ser Arg
            20

<210> SEQ ID NO 4
<211> LENGTH: 491
<212> TYPE: DNA
<213> ORGANISM: Homo Sapiens
<220> FEATURE:
<221> NAME/KEY: CDS
<222> LOCATION: (1)..(489)
<223> OTHER INFORMATION:
<220> FEATURE:
<221> NAME/KEY: misc_feature
<222> LOCATION: (4)..(4)
<223> OTHER INFORMATION: May be any nucleotide
<220> FEATURE:
<221> NAME/KEY: misc_feature
<222> LOCATION: (6)..(6)
<223> OTHER INFORMATION: May be any nucleotide
<220> FEATURE:
<221> NAME/KEY: misc_feature
<222> LOCATION: (67)..(69)
<223> OTHER INFORMATION: May be any nucleotide
<220> FEATURE:
<221> NAME/KEY: misc_feature
<222> LOCATION: (76)..(78)
<223> OTHER INFORMATION: May be any nucleotide
<220> FEATURE:
<221> NAME/KEY: misc_feature
<222> LOCATION: (122)..(122)
<223> OTHER INFORMATION: May be any nucleotide
<220> FEATURE:
<221> NAME/KEY: misc_feature
<222> LOCATION: (207)..(207)
<223> OTHER INFORMATION: May be any nucleotide
<220> FEATURE:
<221> NAME/KEY: misc_feature
<222> LOCATION: (211)..(211)
<223> OTHER INFORMATION: May be any nucleotide
<220> FEATURE:
<221> NAME/KEY: misc_feature
<222> LOCATION: (222)..(222)
```

```
<223> OTHER INFORMATION: May be any nucleotide
<220> FEATURE:
<221> NAME/KEY: misc_feature
<222> LOCATION: (306)..(306)
<223> OTHER INFORMATION: May be any nucleotide
<220> FEATURE:
<221> NAME/KEY: misc_feature
<222> LOCATION: (342)..(342)
<223> OTHER INFORMATION: May be any nucleotide
<220> FEATURE:
<221> NAME/KEY: misc_feature
<222> LOCATION: (357)..(357)
<223> OTHER INFORMATION: May be any nucleotide
<220> FEATURE:
<221> NAME/KEY: misc_feature
<222> LOCATION: (359)..(359)
<223> OTHER INFORMATION: May be any nucleotide
<220> FEATURE:
<221> NAME/KEY: misc_feature
<222> LOCATION: (371)..(373)
<223> OTHER INFORMATION: May be any nucleotide
<220> FEATURE:
<221> NAME/KEY: misc_feature
<222> LOCATION: (378)..(378)
<223> OTHER INFORMATION: May be any nucleotide
<220> FEATURE:
<221> NAME/KEY: misc_feature
<222> LOCATION: (387)..(387)
<223> OTHER INFORMATION: May be any nucleotide
<220> FEATURE:
<221> NAME/KEY: misc_feature
<222> LOCATION: (390)..(390)
<223> OTHER INFORMATION: May be any nucleotide
<220> FEATURE:
<221> NAME/KEY: misc_feature
<222> LOCATION: (396)..(398)
<223> OTHER INFORMATION: May be any nucleotide
<220> FEATURE:
<221> NAME/KEY: misc_feature
<222> LOCATION: (405)..(405)
<223> OTHER INFORMATION: May be any nucleotide
<220> FEATURE:
<221> NAME/KEY: misc_feature
<222> LOCATION: (409)..(411)
<223> OTHER INFORMATION: May be any nucleotide
<220> FEATURE:
<221> NAME/KEY: misc_feature
<222> LOCATION: (413)..(413)
<223> OTHER INFORMATION: May be any nucleotide
<220> FEATURE:
<221> NAME/KEY: misc_feature
<222> LOCATION: (417)..(417)
<223> OTHER INFORMATION: May be any nucleotide
<220> FEATURE:
<221> NAME/KEY: misc_feature
<222> LOCATION: (425)..(425)
<223> OTHER INFORMATION: May be any nucleotide
<220> FEATURE:
<221> NAME/KEY: misc_feature
<222> LOCATION: (429)..(429)
<223> OTHER INFORMATION: May be any nucleotide
<220> FEATURE:
<221> NAME/KEY: misc_feature
<222> LOCATION: (438)..(438)
<223> OTHER INFORMATION: May be any nucleotide
<220> FEATURE:
<221> NAME/KEY: misc_feature
<222> LOCATION: (447)..(448)
<223> OTHER INFORMATION: May be any nucleotide
<220> FEATURE:
<221> NAME/KEY: misc_feature
<222> LOCATION: (461)..(462)
<223> OTHER INFORMATION: May be any nucleotide
<220> FEATURE:
<221> NAME/KEY: misc_feature
<222> LOCATION: (466)..(466)
<223> OTHER INFORMATION: May be any nucleotide
<220> FEATURE:
<221> NAME/KEY: misc_feature
```

<222> LOCATION: (469)..(469)
<223> OTHER INFORMATION: May be any nucleotide
<220> FEATURE:
<221> NAME/KEY: misc_feature
<222> LOCATION: (481)..(483)
<223> OTHER INFORMATION: May be any nucleotide

<400> SEQUENCE: 4

```
agc ngn ctc ttc acc atc ccg ttt tcc agc aag agt cgt tca cca gac      48
Ser Xaa Leu Phe Thr Ile Pro Phe Ser Ser Lys Ser Arg Ser Pro Asp
1               5                   10                  15 agg tgt tat gga agc tgc nnn agg ttg nnn aaa ttc gga gaa gtg att      96
Arg Cys Tyr Gly Ser Cys Xaa Arg Leu Xaa Lys Phe Gly Glu Val Ile
            20                  25                  30 tct tac cag caa tta gca gcc ctg gna ggc aac ccc aaa gcc gcg cga     144
Ser Tyr Gln Gln Leu Ala Ala Leu Xaa Gly Asn Pro Lys Ala Ala Arg
        35                  40                  45 gca gtt ggg agg agc aat gag agg caa tcc tgt ccc cat cct cat ccc     192
Ala Val Gly Arg Ser Asn Glu Arg Gln Ser Cys Pro His Pro His Pro
    50                  55                  60 gtg cca cag agt gtn ctt nca gca gcg gan ccg tgg gca act tac ttc     240
Val Pro Gln Ser Val Leu Xaa Ala Ala Xaa Pro Trp Ala Thr Tyr Phe
65                  70                  75                  80 cgg agg act ggc cgt gaa agg aat ggc ttc tgg ccc atg aaa ggc cac     288
Arg Arg Thr Gly Arg Glu Arg Asn Gly Phe Trp Pro Met Lys Gly His
                85                  90                  95 cgg ttt ggg aag cca agn ttt gga ggg agc ttc agg ttt tgg caa ggg     336
Arg Phe Gly Lys Pro Xaa Phe Gly Gly Ser Phe Arg Phe Trp Gln Gly
            100                 105                 110 cct ggn ttc aag gga gcc ggn gnt acc ttc ggg gnn ncc cgn ctt ttt     384
Pro Gly Phe Lys Gly Ala Gly Xaa Thr Phe Gly Xaa Xaa Arg Leu Phe
        115                 120                 125 ggn cgn aaa ttn nnt ttt ttn cat nnn gnt ggn ttt ttt tng ccn caa     432
Gly Arg Lys Xaa Xaa Phe Xaa His Xaa Xaa Gly Phe Phe Xaa Pro Gln
    130                 135                 140 aaa agn ttt aaa ttn nat tgg ttt ggg gnn ttg ngg nac cct ttt ttt     480
Lys Xaa Phe Lys Xaa Xaa Trp Phe Gly Xaa Leu Xaa Xaa Pro Phe Phe
145                 150                 155                 160 nnn gga agt tg                                                       491
Xaa Gly Ser
```

<210> SEQ ID NO 5
<211> LENGTH: 163
<212> TYPE: PRT
<213> ORGANISM: Homo Sapiens
<220> FEATURE:
<221> NAME/KEY: misc_feature
<222> LOCATION: (2)..(2)
<223> OTHER INFORMATION: The 'Xaa' at location 2 stands for Arg, Ser,
    Gly, a stop codon, Trp, or Cys.
<220> FEATURE:
<221> NAME/KEY: misc_feature
<222> LOCATION: (23)..(23)
<223> OTHER INFORMATION: The 'Xaa' at location 23 stands for Lys, Asn,
    Arg, Ser, Thr, Ile, Met, Glu, Asp, Gly, Ala, Val, Gln, His, Pro,
    Leu, a stop codon, Tyr, Trp, Cys, or Phe.
<220> FEATURE:
<221> NAME/KEY: misc_feature
<222> LOCATION: (26)..(26)
<223> OTHER INFORMATION: The 'Xaa' at location 26 stands for Lys, Asn,
    Arg, Ser, Thr, Ile, Met, Glu, Asp, Gly, Ala, Val, Gln, His, Pro,
    Leu, a stop codon, Tyr, Trp, Cys, or Phe.
<220> FEATURE:
<221> NAME/KEY: misc_feature
<222> LOCATION: (41)..(41)
<223> OTHER INFORMATION: The 'Xaa' at location 41 stands for Glu, Gly,
    Ala, or Val.

-continued

```
<220> FEATURE:
<221> NAME/KEY: misc_feature
<222> LOCATION: (71)..(71)
<223> OTHER INFORMATION: The 'Xaa' at location 71 stands for Thr, Ala,
      Pro, or Ser.
<220> FEATURE:
<221> NAME/KEY: misc_feature
<222> LOCATION: (74)..(74)
<223> OTHER INFORMATION: The 'Xaa' at location 74 stands for Glu, or
      Asp.
<220> FEATURE:
<221> NAME/KEY: misc_feature
<222> LOCATION: (102)..(102)
<223> OTHER INFORMATION: The 'Xaa' at location 102 stands for Arg, or
      Ser.
<220> FEATURE:
<221> NAME/KEY: misc_feature
<222> LOCATION: (120)..(120)
<223> OTHER INFORMATION: The 'Xaa' at location 120 stands for Asp, Gly,
      Ala, or Val.
<220> FEATURE:
<221> NAME/KEY: misc_feature
<222> LOCATION: (124)..(124)
<223> OTHER INFORMATION: The 'Xaa' at location 124 stands for Glu, Asp,
      Gly, Ala, or Val.
<220> FEATURE:
<221> NAME/KEY: misc_feature
<222> LOCATION: (125)..(125)
<223> OTHER INFORMATION: The 'Xaa' at location 125 stands for Thr, Ala,
      Pro, or Ser.
<220> FEATURE:
<221> NAME/KEY: misc_feature
<222> LOCATION: (132)..(132)
<223> OTHER INFORMATION: The 'Xaa' at location 132 stands for Leu, or
      Phe.
<220> FEATURE:
<221> NAME/KEY: misc_feature
<222> LOCATION: (133)..(133)
<223> OTHER INFORMATION: The 'Xaa' at location 133 stands for Asn, Ser,
      Thr, Ile, Asp, Gly, Ala, Val, His, Arg, Pro, Leu, Tyr, Cys, or Phe.
<220> FEATURE:
<221> NAME/KEY: misc_feature
<222> LOCATION: (135)..(135)
<223> OTHER INFORMATION: The 'Xaa' at location 135 stands for Leu, or
      Phe.
<220> FEATURE:
<221> NAME/KEY: misc_feature
<222> LOCATION: (137)..(137)
<223> OTHER INFORMATION: The 'Xaa' at location 137 stands for Lys, Asn,
      Arg, Ser, Thr, Ile, Met, Glu, Asp, Gly, Ala, Val, Gln, His, Pro,
      Leu, a stop codon, Tyr, Trp, Cys, or Phe.
<220> FEATURE:
<221> NAME/KEY: misc_feature
<222> LOCATION: (138)..(138)
<223> OTHER INFORMATION: The 'Xaa' at location 138 stands for Asp, Gly,
      Ala, or Val.
<220> FEATURE:
<221> NAME/KEY: misc_feature
<222> LOCATION: (142)..(142)
<223> OTHER INFORMATION: The 'Xaa' at location 142 stands for a stop
      codon, Trp, Ser, or Leu.
<220> FEATURE:
<221> NAME/KEY: misc_feature
<222> LOCATION: (146)..(146)
<223> OTHER INFORMATION: The 'Xaa' at location 146 stands for Arg, or
      Ser.
<220> FEATURE:
<221> NAME/KEY: misc_feature
<222> LOCATION: (149)..(149)
<223> OTHER INFORMATION: The 'Xaa' at location 149 stands for Leu, or
      Phe.
<220> FEATURE:
<221> NAME/KEY: misc_feature
<222> LOCATION: (150)..(150)
<223> OTHER INFORMATION: The 'Xaa' at location 150 stands for Asn, Asp,
      His, or Tyr.
<220> FEATURE:
<221> NAME/KEY: misc_feature
<222> LOCATION: (154)..(154)
```

```
<223> OTHER INFORMATION: The 'Xaa' at location 154 stands for Glu, Asp,
      Gly, Ala, or Val.
<220> FEATURE:
<221> NAME/KEY: misc_feature
<222> LOCATION: (156)..(156)
<223> OTHER INFORMATION: The 'Xaa' at location 156 stands for Arg, Gly,
      or Trp.
<220> FEATURE:
<221> NAME/KEY: misc_feature
<222> LOCATION: (157)..(157)
<223> OTHER INFORMATION: The 'Xaa' at location 157 stands for Asn, Asp,
      His, or Tyr.
<220> FEATURE:
<221> NAME/KEY: misc_feature
<222> LOCATION: (161)..(161)
<223> OTHER INFORMATION: The 'Xaa' at location 161 stands for Lys, Asn,
      Arg, Ser, Thr, Ile, Met, Glu, Asp, Gly, Ala, Val, Gln, His, Pro,
      Leu, a stop codon, Tyr, Trp, Cys, or Phe.
<220> FEATURE:
<221> NAME/KEY: misc_feature
<222> LOCATION: (4)..(4)
<223> OTHER INFORMATION: May be any nucleotide
<220> FEATURE:
<221> NAME/KEY: misc_feature
<222> LOCATION: (6)..(6)
<223> OTHER INFORMATION: May be any nucleotide
<220> FEATURE:
<221> NAME/KEY: misc_feature
<222> LOCATION: (67)..(69)
<223> OTHER INFORMATION: May be any nucleotide
<220> FEATURE:
<221> NAME/KEY: misc_feature
<222> LOCATION: (76)..(78)
<223> OTHER INFORMATION: May be any nucleotide
<220> FEATURE:
<221> NAME/KEY: misc_feature
<222> LOCATION: (122)..(122)
<223> OTHER INFORMATION: May be any nucleotide
<220> FEATURE:
<221> NAME/KEY: misc_feature
<222> LOCATION: (207)..(207)
<223> OTHER INFORMATION: May be any nucleotide
<220> FEATURE:
<221> NAME/KEY: misc_feature
<222> LOCATION: (211)..(211)
<223> OTHER INFORMATION: May be any nucleotide
<220> FEATURE:
<221> NAME/KEY: misc_feature
<222> LOCATION: (222)..(222)
<223> OTHER INFORMATION: May be any nucleotide
<220> FEATURE:
<221> NAME/KEY: misc_feature
<222> LOCATION: (306)..(306)
<223> OTHER INFORMATION: May be any nucleotide
<220> FEATURE:
<221> NAME/KEY: misc_feature
<222> LOCATION: (342)..(342)
<223> OTHER INFORMATION: May be any nucleotide
<220> FEATURE:
<221> NAME/KEY: misc_feature
<222> LOCATION: (357)..(357)
<223> OTHER INFORMATION: May be any nucleotide
<220> FEATURE:
<221> NAME/KEY: misc_feature
<222> LOCATION: (359)..(359)
<223> OTHER INFORMATION: May be any nucleotide
<220> FEATURE:
<221> NAME/KEY: misc_feature
<222> LOCATION: (371)..(373)
<223> OTHER INFORMATION: May be any nucleotide
<220> FEATURE:
<221> NAME/KEY: misc_feature
<222> LOCATION: (378)..(378)
<223> OTHER INFORMATION: May be any nucleotide
<220> FEATURE:
<221> NAME/KEY: misc_feature
<222> LOCATION: (387)..(387)
<223> OTHER INFORMATION: May be any nucleotide
<220> FEATURE:
```

```
<221> NAME/KEY: misc_feature
<222> LOCATION: (390)..(390)
<223> OTHER INFORMATION: May be any nucleotide
<220> FEATURE:
<221> NAME/KEY: misc_feature
<222> LOCATION: (396)..(398)
<223> OTHER INFORMATION: May be any nucleotide
<220> FEATURE:
<221> NAME/KEY: misc_feature
<222> LOCATION: (405)..(405)
<223> OTHER INFORMATION: May be any nucleotide
<220> FEATURE:
<221> NAME/KEY: misc_feature
<222> LOCATION: (409)..(411)
<223> OTHER INFORMATION: May be any nucleotide
<220> FEATURE:
<221> NAME/KEY: misc_feature
<222> LOCATION: (413)..(413)
<223> OTHER INFORMATION: May be any nucleotide
<220> FEATURE:
<221> NAME/KEY: misc_feature
<222> LOCATION: (417)..(417)
<223> OTHER INFORMATION: May be any nucleotide
<220> FEATURE:
<221> NAME/KEY: misc_feature
<222> LOCATION: (425)..(425)
<223> OTHER INFORMATION: May be any nucleotide
<220> FEATURE:
<221> NAME/KEY: misc_feature
<222> LOCATION: (429)..(429)
<223> OTHER INFORMATION: May be any nucleotide
<220> FEATURE:
<221> NAME/KEY: misc_feature
<222> LOCATION: (438)..(438)
<223> OTHER INFORMATION: May be any nucleotide
<220> FEATURE:
<221> NAME/KEY: misc_feature
<222> LOCATION: (447)..(448)
<223> OTHER INFORMATION: May be any nucleotide
<220> FEATURE:
<221> NAME/KEY: misc_feature
<222> LOCATION: (461)..(462)
<223> OTHER INFORMATION: May be any nucleotide
<220> FEATURE:
<221> NAME/KEY: misc_feature
<222> LOCATION: (466)..(466)
<223> OTHER INFORMATION: May be any nucleotide
<220> FEATURE:
<221> NAME/KEY: misc_feature
<222> LOCATION: (469)..(469)
<223> OTHER INFORMATION: May be any nucleotide
<220> FEATURE:
<221> NAME/KEY: misc_feature
<222> LOCATION: (481)..(483)
<223> OTHER INFORMATION: May be any nucleotide

<400> SEQUENCE: 5

Ser Xaa Leu Phe Thr Ile Pro Phe Ser Ser Lys Ser Arg Ser Pro Asp
 1               5                  10                  15

Arg Cys Tyr Gly Ser Cys Xaa Arg Leu Xaa Lys Phe Gly Glu Val Ile
             20                  25                  30

Ser Tyr Gln Gln Leu Ala Ala Leu Xaa Gly Asn Pro Lys Ala Ala Arg
         35                  40                  45

Ala Val Gly Arg Ser Asn Glu Arg Gln Ser Cys Pro His Pro His Pro
     50                  55                  60

Val Pro Gln Ser Val Leu Xaa Ala Ala Xaa Pro Trp Ala Thr Tyr Phe
65                  70                  75                  80

Arg Arg Thr Gly Arg Glu Arg Asn Gly Phe Trp Pro Met Lys Gly His
                 85                  90                  95

Arg Phe Gly Lys Pro Xaa Phe Gly Gly Ser Phe Arg Phe Trp Gln Gly
            100                 105                 110
```

-continued

```
Pro Gly Phe Lys Gly Ala Gly Xaa Thr Phe Gly Xaa Xaa Arg Leu Phe
        115                 120                 125

Gly Arg Lys Xaa Xaa Phe Xaa His Xaa Xaa Gly Phe Phe Xaa Pro Gln
130                 135                 140

Lys Xaa Phe Lys Xaa Xaa Trp Phe Gly Xaa Leu Xaa Xaa Pro Phe Phe
145                 150                 155                 160

Xaa Gly Ser

<210> SEQ ID NO 6
<211> LENGTH: 489
<212> TYPE: DNA
<213> ORGANISM: Homo sapiens
<220> FEATURE:
<221> NAME/KEY: CDS
<222> LOCATION: (3)..(488)
<223> OTHER INFORMATION:
<220> FEATURE:
<221> NAME/KEY: misc_feature
<222> LOCATION: (58)..(58)
<223> OTHER INFORMATION: May be any nucleotide
<220> FEATURE:
<221> NAME/KEY: misc_feature
<222> LOCATION: (214)..(214)
<223> OTHER INFORMATION: May be any nucleotide
<220> FEATURE:
<221> NAME/KEY: misc_feature
<222> LOCATION: (291)..(293)
<223> OTHER INFORMATION: May be any nucleotide
<220> FEATURE:
<221> NAME/KEY: misc_feature
<222> LOCATION: (298)..(298)
<223> OTHER INFORMATION: May be any nucleotide
<220> FEATURE:
<221> NAME/KEY: misc_feature
<222> LOCATION: (325)..(325)
<223> OTHER INFORMATION: May be any nucleotide
<220> FEATURE:
<221> NAME/KEY: misc_feature
<222> LOCATION: (339)..(339)
<223> OTHER INFORMATION: May be any nucleotide
<220> FEATURE:
<221> NAME/KEY: misc_feature
<222> LOCATION: (357)..(359)
<223> OTHER INFORMATION: May be any nucleotide
<220> FEATURE:
<221> NAME/KEY: misc_feature
<222> LOCATION: (368)..(368)
<223> OTHER INFORMATION: May be any nucleotide
<220> FEATURE:
<221> NAME/KEY: misc_feature
<222> LOCATION: (402)..(404)
<223> OTHER INFORMATION: May be any nucleotide
<220> FEATURE:
<221> NAME/KEY: misc_feature
<222> LOCATION: (416)..(416)
<223> OTHER INFORMATION: May be any nucleotide
<220> FEATURE:
<221> NAME/KEY: misc_feature
<222> LOCATION: (426)..(428)
<223> OTHER INFORMATION: May be any nucleotide
<220> FEATURE:
<221> NAME/KEY: misc_feature
<222> LOCATION: (432)..(432)
<223> OTHER INFORMATION: May be any nucleotide
<220> FEATURE:
<221> NAME/KEY: misc_feature
<222> LOCATION: (434)..(434)
<223> OTHER INFORMATION: May be any nucleotide
<220> FEATURE:
<221> NAME/KEY: misc_feature
<222> LOCATION: (438)..(438)
<223> OTHER INFORMATION: May be any nucleotide
<220> FEATURE:
<221> NAME/KEY: misc_feature
<222> LOCATION: (441)..(441)
```

```
<223> OTHER INFORMATION: May be any nucleotide
<220> FEATURE:
<221> NAME/KEY: misc_feature
<222> LOCATION: (455)..(455)
<223> OTHER INFORMATION: May be any nucleotide
<220> FEATURE:
<221> NAME/KEY: misc_feature
<222> LOCATION: (478)..(478)
<223> OTHER INFORMATION: May be any nucleotide
<220> FEATURE:
<221> NAME/KEY: misc_feature
<222> LOCATION: (481)..(481)
<223> OTHER INFORMATION: May be any nucleotide

<400> SEQUENCE: 6 ga ggg acc gcc gac cac cac cag ctg cgc tca ctg act ggc ctc atc         47
   Gly Thr Ala Asp His His Gln Leu Arg Ser Leu Thr Gly Leu Ile
   1               5                  10                  15 cga aac ctg tnt cgg aac gct agg aac aag gac gag atg tcc acg aag         95
Arg Asn Leu Xaa Arg Asn Ala Arg Asn Lys Asp Glu Met Ser Thr Lys
                20                  25                  30 gtg gtg agc cac ctg atc gag aag ctg ccg ggc agc gtg ggt gag aag        143
Val Val Ser His Leu Ile Glu Lys Leu Pro Gly Ser Val Gly Glu Lys
            35                  40                  45 tcg ccc cca gcc gag gtg ctg gtc aac atc ata gct gtg ctc aac aac        191
Ser Pro Pro Ala Glu Val Leu Val Asn Ile Ile Ala Val Leu Asn Asn
        50                  55                  60 ctg gtg gtg gcc agc ccc atc gnt gcc cga gac ctg ctg tat ttt gac        239
Leu Val Val Ala Ser Pro Ile Xaa Ala Arg Asp Leu Leu Tyr Phe Asp
    65                  70                  75 gga ctc cga aag ctc atc ttc atc aag aag aag cgg gac agc ccc gac        287
Gly Leu Arg Lys Leu Ile Phe Ile Lys Lys Lys Arg Asp Ser Pro Asp
80                  85                  90                  95 agt nnn aag tnc tcc cgg gca gca tcc agc ctc ctg gnc aac ctg ttg        335
Ser Xaa Lys Xaa Ser Arg Ala Ala Ser Ser Leu Leu Xaa Asn Leu Leu
                100                 105                 110 gca nta caa caa gtt cca ccg nnn ttt ccg ggn gaa ggg ttt tcg gaa        383
Ala Xaa Gln Gln Val Pro Pro Xaa Phe Pro Gly Glu Gly Phe Ser Glu
            115                 120                 125 gga gga ttt ctg ggg cct nnn gtg aag ctt ttn gag gag agg nnn cgt        431
Gly Gly Phe Leu Gly Pro Xaa Val Lys Leu Xaa Glu Glu Arg Xaa Arg
        130                 135                 140 ngn cca ngt nca ggg aca gat tan ttc agt ttt tgg acc cag ctt gng        479
Xaa Pro Xaa Xaa Gly Thr Asp Xaa Phe Ser Phe Trp Thr Gln Leu Xaa
    145                 150                 155 gng agg tat t                                                          489
Xaa Arg Tyr
160

<210> SEQ ID NO 7
<211> LENGTH: 162
<212> TYPE: PRT
<213> ORGANISM: Homo sapiens
<220> FEATURE:
<221> NAME/KEY: misc_feature
<222> LOCATION: (19)..(19)
<223> OTHER INFORMATION: The 'Xaa' at location 19 stands for Tyr, Cys,
      Ser, or Phe.
<220> FEATURE:
<221> NAME/KEY: misc_feature
<222> LOCATION: (71)..(71)
<223> OTHER INFORMATION: The 'Xaa' at location 71 stands for Asp, Gly,
      Ala, or Val.
<220> FEATURE:
<221> NAME/KEY: misc_feature
<222> LOCATION: (97)..(97)
<223> OTHER INFORMATION: The 'Xaa' at location 97 stands for Lys, Asn,
```

```
        Arg, Ser, Thr, Ile,
        Met, Glu, Asp, Gly, Ala, Val, Gln, His, Pro, Leu, a stop codon,
        Tyr, Trp, Cys, or Phe.
<220> FEATURE:
<221> NAME/KEY: misc_feature
<222> LOCATION: (99)..(99)
<223> OTHER INFORMATION: The 'Xaa' at location 99 stands for Tyr, Cys,
        Ser, or Phe.
<220> FEATURE:
<221> NAME/KEY: misc_feature
<222> LOCATION: (108)..(108)
<223> OTHER INFORMATION: The 'Xaa' at location 108 stands for Asp, Gly,
        Ala, or Val.
<220> FEATURE:
<221> NAME/KEY: misc_feature
<222> LOCATION: (113)..(113)
<223> OTHER INFORMATION: The 'Xaa' at location 113 stands for Ile, Val,
        or Leu.
<220> FEATURE:
<221> NAME/KEY: misc_feature
<222> LOCATION: (119)..(119)
<223> OTHER INFORMATION: The 'Xaa' at location 119 stands for Lys, Asn,
        Arg, Ser, Thr, Ile
        , Met, Glu, Asp, Gly, Ala, Val, Gln, His, Pro, Leu, a stop codon,
        Tyr, Trp, Cys, or Phe.
<220> FEATURE:
<221> NAME/KEY: misc_feature
<222> LOCATION: (134)..(134)
<223> OTHER INFORMATION: The 'Xaa' at location 134 stands for Lys, Asn,
        Arg, Ser, Thr, Ile
        , Met, Glu, Asp, Gly, Ala, Val, Gln, His, Pro, Leu, a stop codon,
        Tyr, Trp, Cys, or Phe.
<220> FEATURE:
<221> NAME/KEY: misc_feature
<222> LOCATION: (138)..(138)
<223> OTHER INFORMATION: The 'Xaa' at location 138 stands for Leu, or
        Phe.
<220> FEATURE:
<221> NAME/KEY: misc_feature
<222> LOCATION: (142)..(142)
<223> OTHER INFORMATION: The 'Xaa' at location 142 stands for Lys, Asn,
        Arg, Ser, Thr, Ile
        , Met, Glu, Asp, Gly, Ala, Val, Gln, His, Pro, Leu, a stop codon,
        Tyr, Trp, Cys, or Phe.
<220> FEATURE:
<221> NAME/KEY: misc_feature
<222> LOCATION: (144)..(144)
<223> OTHER INFORMATION: The 'Xaa' at location 144 stands for Arg, Ser,
        Gly, a stop codon,
        Trp, or Cys.
<220> FEATURE:
<221> NAME/KEY: misc_feature
<222> LOCATION: (146)..(146)
<223> OTHER INFORMATION: The 'Xaa' at location 146 stands for Ser, Gly,
        Arg, or Cys.
<220> FEATURE:
<221> NAME/KEY: misc_feature
<222> LOCATION: (147)..(147)
<223> OTHER INFORMATION: The 'Xaa' at location 147 stands for Thr, Ala,
        Pro, or Ser.
<220> FEATURE:
<221> NAME/KEY: misc_feature
<222> LOCATION: (151)..(151)
<223> OTHER INFORMATION: The 'Xaa' at location 151 stands for a stop
        codon, or Tyr.
<220> FEATURE:
<221> NAME/KEY: misc_feature
<222> LOCATION: (159)..(159)
<223> OTHER INFORMATION: The 'Xaa' at location 159 stands for Glu, Gly,
        Ala, or Val.
<220> FEATURE:
<221> NAME/KEY: misc_feature
<222> LOCATION: (160)..(160)
<223> OTHER INFORMATION: The 'Xaa' at location 160 stands for Glu, Gly,
        Ala, or Val.
<220> FEATURE:
<221> NAME/KEY: misc_feature
<222> LOCATION: (58)..(58)
<223> OTHER INFORMATION: May be any nucleotide
```

```
<220> FEATURE:
<221> NAME/KEY: misc_feature
<222> LOCATION: (214)..(214)
<223> OTHER INFORMATION: May be any nucleotide
<220> FEATURE:
<221> NAME/KEY: misc_feature
<222> LOCATION: (291)..(293)
<223> OTHER INFORMATION: May be any nucleotide
<220> FEATURE:
<221> NAME/KEY: misc_feature
<222> LOCATION: (298)..(298)
<223> OTHER INFORMATION: May be any nucleotide
<220> FEATURE:
<221> NAME/KEY: misc_feature
<222> LOCATION: (325)..(325)
<223> OTHER INFORMATION: May be any nucleotide
<220> FEATURE:
<221> NAME/KEY: misc_feature
<222> LOCATION: (339)..(339)
<223> OTHER INFORMATION: May be any nucleotide
<220> FEATURE:
<221> NAME/KEY: misc_feature
<222> LOCATION: (357)..(359)
<223> OTHER INFORMATION: May be any nucleotide
<220> FEATURE:
<221> NAME/KEY: misc_feature
<222> LOCATION: (368)..(368)
<223> OTHER INFORMATION: May be any nucleotide
<220> FEATURE:
<221> NAME/KEY: misc_feature
<222> LOCATION: (402)..(404)
<223> OTHER INFORMATION: May be any nucleotide
<220> FEATURE:
<221> NAME/KEY: misc_feature
<222> LOCATION: (416)..(416)
<223> OTHER INFORMATION: May be any nucleotide
<220> FEATURE:
<221> NAME/KEY: misc_feature
<222> LOCATION: (426)..(428)
<223> OTHER INFORMATION: May be any nucleotide
<220> FEATURE:
<221> NAME/KEY: misc_feature
<222> LOCATION: (432)..(432)
<223> OTHER INFORMATION: May be any nucleotide
<220> FEATURE:
<221> NAME/KEY: misc_feature
<222> LOCATION: (434)..(434)
<223> OTHER INFORMATION: May be any nucleotide
<220> FEATURE:
<221> NAME/KEY: misc_feature
<222> LOCATION: (438)..(438)
<223> OTHER INFORMATION: May be any nucleotide
<220> FEATURE:
<221> NAME/KEY: misc_feature
<222> LOCATION: (441)..(441)
<223> OTHER INFORMATION: May be any nucleotide
<220> FEATURE:
<221> NAME/KEY: misc_feature
<222> LOCATION: (455)..(455)
<223> OTHER INFORMATION: May be any nucleotide
<220> FEATURE:
<221> NAME/KEY: misc_feature
<222> LOCATION: (478)..(478)
<223> OTHER INFORMATION: May be any nucleotide
<220> FEATURE:
<221> NAME/KEY: misc_feature
<222> LOCATION: (481)..(481)
<223> OTHER INFORMATION: May be any nucleotide

<400> SEQUENCE: 7

Gly Thr Ala Asp His His Gln Leu Arg Ser Leu Thr Gly Leu Ile Arg
 1               5                  10                  15

Asn Leu Xaa Arg Asn Ala Arg Asn Lys Asp Glu Met Ser Thr Lys Val
                20                  25                  30

Val Ser His Leu Ile Glu Lys Leu Pro Gly Ser Val Gly Glu Lys Ser
        35                  40                  45
```

Pro Pro Ala Glu Val Leu Val Asn Ile Ile Ala Val Leu Asn Asn Leu
50                   55                  60

Val Val Ala Ser Pro Ile Xaa Ala Arg Asp Leu Leu Tyr Phe Asp Gly
65                  70                  75                  80

Leu Arg Lys Leu Ile Phe Ile Lys Lys Lys Arg Asp Ser Pro Asp Ser
                85                  90                  95

Xaa Lys Xaa Ser Arg Ala Ala Ser Ser Leu Leu Xaa Asn Leu Leu Ala
        100                 105                 110

Xaa Gln Gln Val Pro Pro Xaa Phe Pro Gly Glu Gly Phe Ser Glu Gly
        115                 120                 125

Gly Phe Leu Gly Pro Xaa Val Lys Leu Xaa Glu Glu Arg Xaa Arg Xaa
        130                 135                 140

Pro Xaa Xaa Gly Thr Asp Xaa Phe Ser Phe Trp Thr Gln Leu Xaa Xaa
145                 150                 155                 160

Arg Tyr

<210> SEQ ID NO 8
<211> LENGTH: 442
<212> TYPE: DNA
<213> ORGANISM: Homo sapiens
<220> FEATURE:
<221> NAME/KEY: misc_feature
<222> LOCATION: (84)..(84)
<223> OTHER INFORMATION: May be any nucleotide
<220> FEATURE:
<221> NAME/KEY: misc_feature
<222> LOCATION: (100)..(100)
<223> OTHER INFORMATION: May be any nucleotide
<220> FEATURE:
<221> NAME/KEY: misc_feature
<222> LOCATION: (108)..(108)
<223> OTHER INFORMATION: May be any nucleotide
<220> FEATURE:
<221> NAME/KEY: misc_feature
<222> LOCATION: (120)..(120)
<223> OTHER INFORMATION: May be any nucleotide
<220> FEATURE:
<221> NAME/KEY: misc_feature
<222> LOCATION: (204)..(204)
<223> OTHER INFORMATION: May be any nucleotide
<220> FEATURE:
<221> NAME/KEY: misc_feature
<222> LOCATION: (217)..(217)
<223> OTHER INFORMATION: May be any nucleotide
<220> FEATURE:
<221> NAME/KEY: misc_feature
<222> LOCATION: (271)..(271)
<223> OTHER INFORMATION: May be any nucleotide
<220> FEATURE:
<221> NAME/KEY: misc_feature
<222> LOCATION: (327)..(327)
<223> OTHER INFORMATION: May be any nucleotide
<220> FEATURE:
<221> NAME/KEY: misc_feature
<222> LOCATION: (330)..(330)
<223> OTHER INFORMATION: May be any nucleotide
<220> FEATURE:
<221> NAME/KEY: misc_feature
<222> LOCATION: (334)..(334)
<223> OTHER INFORMATION: May be any nucleotide
<220> FEATURE:
<221> NAME/KEY: misc_feature
<222> LOCATION: (340)..(341)
<223> OTHER INFORMATION: May be any nucleotide
<220> FEATURE:
<221> NAME/KEY: misc_feature
<222> LOCATION: (343)..(343)
<223> OTHER INFORMATION: May be any nucleotide
<220> FEATURE:
<221> NAME/KEY: misc_feature

```
<222> LOCATION: (346)..(346)
<223> OTHER INFORMATION: May be any nucleotide
<220> FEATURE:
<221> NAME/KEY: misc_feature
<222> LOCATION: (352)..(352)
<223> OTHER INFORMATION: May be any nucleotide
<220> FEATURE:
<221> NAME/KEY: misc_feature
<222> LOCATION: (355)..(355)
<223> OTHER INFORMATION: May be any nucleotide
<220> FEATURE:
<221> NAME/KEY: misc_feature
<222> LOCATION: (361)..(361)
<223> OTHER INFORMATION: May be any nucleotide
<220> FEATURE:
<221> NAME/KEY: misc_feature
<222> LOCATION: (374)..(374)
<223> OTHER INFORMATION: May be any nucleotide
<220> FEATURE:
<221> NAME/KEY: misc_feature
<222> LOCATION: (393)..(393)
<223> OTHER INFORMATION: May be any nucleotide
<220> FEATURE:
<221> NAME/KEY: misc_feature
<222> LOCATION: (407)..(407)
<223> OTHER INFORMATION: May be any nucleotide
<220> FEATURE:
<221> NAME/KEY: misc_feature
<222> LOCATION: (420)..(420)
<223> OTHER INFORMATION: May be any nucleotide

<400> SEQUENCE: 8
agcccagccc cagcctgccg gagcccacgg agctacctct acctccactc ctgccaccgc      60
cgccgccctc gaccaccgcc cctntcccca tccgtcccen ctcagggnac caagaagttn     120
caagaggggc cgtgggcgtg ccagggcgct agggaagccg ggtgggggtg agggtagccc     180
ttgagccctg tccctgcggc tgtnaagagc agcaggnacc ctgggccagt tccagagacc     240
tgggggtgtg tttgggggtg gggtgtgagt ncgtatgaaa atgtgtgttt gctggggggca    300 attgtgccct ggaatcatgg gcaggtnggn ccgntccggn nangngnccgg gnttnaaatt    360 ntttccgtgg aagntttaaa gggttgaatt tanggtaaaa aaccttnggg gaagggaagn     420
tttccaaggc aaaaaaaggt tt                                              442

<210> SEQ ID NO 9
<211> LENGTH: 492
<212> TYPE: DNA
<213> ORGANISM: Homo sapiens
<220> FEATURE:
<221> NAME/KEY: CDS
<222> LOCATION: (2)..(490)
<223> OTHER INFORMATION:
<220> FEATURE:
<221> NAME/KEY: misc_feature
<222> LOCATION: (41)..(43)
<223> OTHER INFORMATION: May be any nucleotide
<220> FEATURE:
<221> NAME/KEY: misc_feature
<222> LOCATION: (107)..(107)
<223> OTHER INFORMATION: May be any nucleotide
<220> FEATURE:
<221> NAME/KEY: misc_feature
<222> LOCATION: (119)..(121)
<223> OTHER INFORMATION: May be any nucleotide
<220> FEATURE:
<221> NAME/KEY: misc_feature
<222> LOCATION: (211)..(211)
<223> OTHER INFORMATION: May be any nucleotide
<220> FEATURE:
<221> NAME/KEY: misc_feature
<222> LOCATION: (213)..(213)
<223> OTHER INFORMATION: May be any nucleotide
<220> FEATURE:
```

-continued

```
<221> NAME/KEY: misc_feature
<222> LOCATION: (216)..(216)
<223> OTHER INFORMATION: May be any nucleotide
<220> FEATURE:
<221> NAME/KEY: misc_feature
<222> LOCATION: (256)..(256)
<223> OTHER INFORMATION: May be any nucleotide
<220> FEATURE:
<221> NAME/KEY: misc_feature
<222> LOCATION: (274)..(274)
<223> OTHER INFORMATION: May be any nucleotide
<220> FEATURE:
<221> NAME/KEY: misc_feature
<222> LOCATION: (308)..(310)
<223> OTHER INFORMATION: May be any nucleotide
<220> FEATURE:
<221> NAME/KEY: misc_feature
<222> LOCATION: (314)..(314)
<223> OTHER INFORMATION: May be any nucleotide
<220> FEATURE:
<221> NAME/KEY: misc_feature
<222> LOCATION: (325)..(325)
<223> OTHER INFORMATION: May be any nucleotide
<220> FEATURE:
<221> NAME/KEY: misc_feature
<222> LOCATION: (348)..(348)
<223> OTHER INFORMATION: May be any nucleotide
<220> FEATURE:
<221> NAME/KEY: misc_feature
<222> LOCATION: (354)..(354)
<223> OTHER INFORMATION: May be any nucleotide
<220> FEATURE:
<221> NAME/KEY: misc_feature
<222> LOCATION: (371)..(371)
<223> OTHER INFORMATION: May be any nucleotide
<220> FEATURE:
<221> NAME/KEY: misc_feature
<222> LOCATION: (374)..(374)
<223> OTHER INFORMATION: May be any nucleotide
<220> FEATURE:
<221> NAME/KEY: misc_feature
<222> LOCATION: (391)..(391)
<223> OTHER INFORMATION: May be any nucleotide
<220> FEATURE:
<221> NAME/KEY: misc_feature
<222> LOCATION: (405)..(405)
<223> OTHER INFORMATION: May be any nucleotide
<220> FEATURE:
<221> NAME/KEY: misc_feature
<222> LOCATION: (411)..(411)
<223> OTHER INFORMATION: May be any nucleotide
<220> FEATURE:
<221> NAME/KEY: misc_feature
<222> LOCATION: (425)..(425)
<223> OTHER INFORMATION: May be any nucleotide
<220> FEATURE:
<221> NAME/KEY: misc_feature
<222> LOCATION: (427)..(427)
<223> OTHER INFORMATION: May be any nucleotide
<220> FEATURE:
<221> NAME/KEY: misc_feature
<222> LOCATION: (442)..(442)
<223> OTHER INFORMATION: May be any nucleotide
<220> FEATURE:
<221> NAME/KEY: misc_feature
<222> LOCATION: (465)..(465)
<223> OTHER INFORMATION: May be any nucleotide
<220> FEATURE:
<221> NAME/KEY: misc_feature
<222> LOCATION: (477)..(477)
<223> OTHER INFORMATION: May be any nucleotide
<220> FEATURE:
<221> NAME/KEY: misc_feature
<222> LOCATION: (479)..(479)
<223> OTHER INFORMATION: May be any nucleotide

<400> SEQUENCE: 9 a gac tcc ccg gct ggg tac ccc cct gtg gct ggc tct gcg nnn atc atg      49
```

|  |  |  |  |  |  |  |  |  |  |  |  |  |  |  |
|---|---|---|---|---|---|---|---|---|---|---|---|---|---|---|
| Asp | Ser | Pro | Ala | Gly | Tyr | Pro | Pro | Val | Ala | Gly | Ser | Ala | Xaa | Ile Met |
| 1 |  |  | 5 |  |  |  |  | 10 |  |  |  |  | 15 |  |

```
gat gcc ctg aac agc ctc gcc acg gac tcg cct tgt ggg atc ccc ccc      97
Asp Ala Leu Asn Ser Leu Ala Thr Asp Ser Pro Cys Gly Ile Pro Pro
            20                  25                  30 aag atg tgg naa gac cag ccc nnn ccc ctc gcc ggt gtc tgc cgc ccc     145
Lys Met Trp Xaa Asp Gln Pro Xaa Pro Leu Ala Gly Val Cys Arg Pro
            35                  40                  45 atc caa ggc cgg cct gcc tcg cca cat cta ccc ggc cgt gga gtt cct     193
Ile Gln Gly Arg Pro Ala Ser Pro His Leu Pro Gly Arg Gly Val Pro
        50                  55                  60 ggg gcc ctg cga agc agn gna gna gga gaa act cgg ctc cag aat cca     241
Gly Ala Leu Arg Ser Xaa Xaa Xaa Gly Glu Thr Arg Leu Gln Asn Pro
65                  70                  75                  80 tcc tgc tgg ttc cgn cca ctt ggc cca agc cgn tgg tgc ctg cca ttc     289
Ser Cys Trp Phe Arg Pro Leu Gly Pro Ser Arg Trp Cys Leu Pro Phe
                85                  90                  95 cca tct gca gca tcc cag nnn ctg nat ccc tcc ttn cat ttg agt ggc     337
Pro Ser Ala Ala Ser Gln Xaa Leu Xaa Pro Ser Xaa His Leu Ser Gly
            100                 105                 110 cgt tgt tcc ant cat tna ggt ttt aag gag ttg ngg ntt gag gtg cag     385
Arg Cys Ser Xaa His Xaa Gly Phe Lys Glu Leu Xaa Xaa Glu Val Gln
            115                 120                 125 cca agn caa att aac ggg gnc cat tnt gag aaa aag gaa ncn agg gtt     433
Pro Xaa Gln Ile Asn Gly Xaa His Xaa Glu Lys Lys Glu Xaa Arg Val
        130                 135                 140 tta aaa ttn caa ttg ggg caa ctt tgg ttt ant tca tgg tta ang naa     481
Leu Lys Xaa Gln Leu Gly Gln Leu Trp Phe Xaa Ser Trp Leu Xaa Xaa
145                 150                 155                 160 aaa agt ttg gg                                                       492
Lys Ser Leu
```

<210> SEQ ID NO 10
<211> LENGTH: 163
<212> TYPE: PRT
<213> ORGANISM: Homo sapiens
<220> FEATURE:
<221> NAME/KEY: misc_feature
<222> LOCATION: (14)..(14)
<223> OTHER INFORMATION: The 'Xaa' at location 14 stands for Lys, Asn,
      Arg, Ser, Thr, Ile,
      Met, Glu, Asp, Gly, Ala, Val, Gln, His, Pro, Leu, a stop codon,
      Tyr, Trp, Cys, or Phe.
<220> FEATURE:
<221> NAME/KEY: misc_feature
<222> LOCATION: (36)..(36)
<223> OTHER INFORMATION: The 'Xaa' at location 36 stands for Lys, Glu,
      Gln, or a stop codon.
<220> FEATURE:
<221> NAME/KEY: misc_feature
<222> LOCATION: (40)..(40)
<223> OTHER INFORMATION: The 'Xaa' at location 40 stands for Lys, Asn,
      Arg, Ser, Thr, Ile, Met, Glu, Asp, Gly, Ala, Val, Gln, His, Pro,
      Leu, a stop codon, Tyr, Trp, Cys, or Phe.
<220> FEATURE:
<221> NAME/KEY: misc_feature
<222> LOCATION: (70)..(70)
<223> OTHER INFORMATION: The 'Xaa' at location 70 stands for Arg, or
      Ser.
<220> FEATURE:
<221> NAME/KEY: misc_feature
<222> LOCATION: (71)..(71)
<223> OTHER INFORMATION: The 'Xaa' at location 71 stands for Glu, Gly,
      Ala, or Val.
<220> FEATURE:
<221> NAME/KEY: misc_feature
<222> LOCATION: (72)..(72)
<223> OTHER INFORMATION: The 'Xaa' at location 72 stands for Glu, Gly,

```
      Ala, or Val.
<220> FEATURE:
<221> NAME/KEY: misc_feature
<222> LOCATION: (103)..(103)
<223> OTHER INFORMATION: The 'Xaa' at location 103 stands for Lys, Asn,
      Arg, Ser, Thr, Ile, Met, Glu, Asp, Gly, Ala, Val, Gln, His, Pro,
      Leu, a stop codon, Tyr, Trp, Cys, or Phe.
<220> FEATURE:
<221> NAME/KEY: misc_feature
<222> LOCATION: (105)..(105)
<223> OTHER INFORMATION: The 'Xaa' at location 105 stands for Asn, Asp,
      His, or Tyr.
<220> FEATURE:
<221> NAME/KEY: misc_feature
<222> LOCATION: (108)..(108)
<223> OTHER INFORMATION: The 'Xaa' at location 108 stands for Leu, or
      Phe.
<220> FEATURE:
<221> NAME/KEY: misc_feature
<222> LOCATION: (116)..(116)
<223> OTHER INFORMATION: The 'Xaa' at location 116 stands for Asn, Ser,
      Thr, or Ile.
<220> FEATURE:
<221> NAME/KEY: misc_feature
<222> LOCATION: (118)..(118)
<223> OTHER INFORMATION: The 'Xaa' at location 118 stands for a stop
      codon, Ser, or Leu.
<220> FEATURE:
<221> NAME/KEY: misc_feature
<222> LOCATION: (124)..(124)
<223> OTHER INFORMATION: The 'Xaa' at location 124 stands for Arg, Gly,
      or Trp.
<220> FEATURE:
<221> NAME/KEY: misc_feature
<222> LOCATION: (125)..(125)
<223> OTHER INFORMATION: The 'Xaa' at location 125 stands for Ile, Val,
      Leu, or Phe.
<220> FEATURE:
<221> NAME/KEY: misc_feature
<222> LOCATION: (130)..(130)
<223> OTHER INFORMATION: The 'Xaa' at location 130 stands for Arg, or
      Ser.
<220> FEATURE:
<221> NAME/KEY: misc_feature
<222> LOCATION: (135)..(135)
<223> OTHER INFORMATION: The 'Xaa' at location 135 stands for Asp, Gly,
      Ala, or Val.
<220> FEATURE:
<221> NAME/KEY: misc_feature
<222> LOCATION: (137)..(137)
<223> OTHER INFORMATION: The 'Xaa' at location 137 stands for Tyr, Cys,
      Ser, or Phe.
<220> FEATURE:
<221> NAME/KEY: misc_feature
<222> LOCATION: (142)..(142)
<223> OTHER INFORMATION: The 'Xaa' at location 142 stands for Thr, Ala,
      Pro, or Ser.
<220> FEATURE:
<221> NAME/KEY: misc_feature
<222> LOCATION: (147)..(147)
<223> OTHER INFORMATION: The 'Xaa' at location 147 stands for Leu, or
      Phe.
<220> FEATURE:
<221> NAME/KEY: misc_feature
<222> LOCATION: (155)..(155)
<223> OTHER INFORMATION: The 'Xaa' at location 155 stands for Asn, Ser,
      Thr, or Ile.
<220> FEATURE:
<221> NAME/KEY: misc_feature
<222> LOCATION: (159)..(159)
<223> OTHER INFORMATION: The 'Xaa' at location 159 stands for Lys, Arg,
      Thr, or Met.
<220> FEATURE:
<221> NAME/KEY: misc_feature
<222> LOCATION: (160)..(160)
<223> OTHER INFORMATION: The 'Xaa' at location 160 stands for Lys, Glu,
      Gln, or a stop codon.
<220> FEATURE:
<221> NAME/KEY: misc_feature
```

```
<222> LOCATION: (41)..(43)
<223> OTHER INFORMATION: May be any nucleotide
<220> FEATURE:
<221> NAME/KEY: misc_feature
<222> LOCATION: (107)..(107)
<223> OTHER INFORMATION: May be any nucleotide
<220> FEATURE:
<221> NAME/KEY: misc_feature
<222> LOCATION: (119)..(121)
<223> OTHER INFORMATION: May be any nucleotide
<220> FEATURE:
<221> NAME/KEY: misc_feature
<222> LOCATION: (211)..(211)
<223> OTHER INFORMATION: May be any nucleotide
<220> FEATURE:
<221> NAME/KEY: misc_feature
<222> LOCATION: (213)..(213)
<223> OTHER INFORMATION: May be any nucleotide
<220> FEATURE:
<221> NAME/KEY: misc_feature
<222> LOCATION: (216)..(216)
<223> OTHER INFORMATION: May be any nucleotide
<220> FEATURE:
<221> NAME/KEY: misc_feature
<222> LOCATION: (256)..(256)
<223> OTHER INFORMATION: May be any nucleotide
<220> FEATURE:
<221> NAME/KEY: misc_feature
<222> LOCATION: (274)..(274)
<223> OTHER INFORMATION: May be any nucleotide
<220> FEATURE:
<221> NAME/KEY: misc_feature
<222> LOCATION: (308)..(310)
<223> OTHER INFORMATION: May be any nucleotide
<220> FEATURE:
<221> NAME/KEY: misc_feature
<222> LOCATION: (314)..(314)
<223> OTHER INFORMATION: May be any nucleotide
<220> FEATURE:
<221> NAME/KEY: misc_feature
<222> LOCATION: (325)..(325)
<223> OTHER INFORMATION: May be any nucleotide
<220> FEATURE:
<221> NAME/KEY: misc_feature
<222> LOCATION: (348)..(348)
<223> OTHER INFORMATION: May be any nucleotide
<220> FEATURE:
<221> NAME/KEY: misc_feature
<222> LOCATION: (354)..(354)
<223> OTHER INFORMATION: May be any nucleotide
<220> FEATURE:
<221> NAME/KEY: misc_feature
<222> LOCATION: (371)..(371)
<223> OTHER INFORMATION: May be any nucleotide
<220> FEATURE:
<221> NAME/KEY: misc_feature
<222> LOCATION: (374)..(374)
<223> OTHER INFORMATION: May be any nucleotide
<220> FEATURE:
<221> NAME/KEY: misc_feature
<222> LOCATION: (391)..(391)
<223> OTHER INFORMATION: May be any nucleotide
<220> FEATURE:
<221> NAME/KEY: misc_feature
<222> LOCATION: (405)..(405)
<223> OTHER INFORMATION: May be any nucleotide
<220> FEATURE:
<221> NAME/KEY: misc_feature
<222> LOCATION: (411)..(411)
<223> OTHER INFORMATION: May be any nucleotide
<220> FEATURE:
<221> NAME/KEY: misc_feature
<222> LOCATION: (425)..(425)
<223> OTHER INFORMATION: May be any nucleotide
<220> FEATURE:
<221> NAME/KEY: misc_feature
<222> LOCATION: (427)..(427)
<223> OTHER INFORMATION: May be any nucleotide
<220> FEATURE:
```

<221> NAME/KEY: misc_feature
<222> LOCATION: (442)..(442)
<223> OTHER INFORMATION: May be any nucleotide
<220> FEATURE:
<221> NAME/KEY: misc_feature
<222> LOCATION: (465)..(465)
<223> OTHER INFORMATION: May be any nucleotide
<220> FEATURE:
<221> NAME/KEY: misc_feature
<222> LOCATION: (477)..(477)
<223> OTHER INFORMATION: May be any nucleotide
<220> FEATURE:
<221> NAME/KEY: misc_feature
<222> LOCATION: (479)..(479)
<223> OTHER INFORMATION: May be any nucleotide

<400> SEQUENCE: 10

Asp Ser Pro Ala Gly Tyr Pro Pro Val Ala Gly Ser Ala Xaa Ile Met
1               5                   10                  15

Asp Ala Leu Asn Ser Leu Ala Thr Asp Ser Pro Cys Gly Ile Pro Pro
            20                  25                  30

Lys Met Trp Xaa Asp Gln Pro Xaa Pro Leu Ala Gly Val Cys Arg Pro
        35                  40                  45

Ile Gln Gly Arg Pro Ala Ser Pro His Leu Pro Gly Arg Gly Val Pro
    50                  55                  60

Gly Ala Leu Arg Ser Xaa Xaa Xaa Gly Glu Thr Arg Leu Gln Asn Pro
65                  70                  75                  80

Ser Cys Trp Phe Arg Pro Leu Gly Pro Ser Arg Trp Cys Leu Pro Phe
                85                  90                  95

Pro Ser Ala Ala Ser Gln Xaa Leu Xaa Pro Ser Xaa His Leu Ser Gly
            100                 105                 110

Arg Cys Ser Xaa His Xaa Gly Phe Lys Glu Leu Xaa Xaa Glu Val Gln
        115                 120                 125

Pro Xaa Gln Ile Asn Gly Xaa His Xaa Glu Lys Lys Glu Xaa Arg Val
    130                 135                 140

Leu Lys Xaa Gln Leu Gly Gln Leu Trp Phe Xaa Ser Trp Leu Xaa Xaa
145                 150                 155                 160

Lys Ser Leu

<210> SEQ ID NO 11
<211> LENGTH: 484
<212> TYPE: DNA
<213> ORGANISM: Homo sapiens
<220> FEATURE:
<221> NAME/KEY: misc_feature
<222> LOCATION: (82)..(82)
<223> OTHER INFORMATION: May be any nucleotide
<220> FEATURE:
<221> NAME/KEY: misc_feature
<222> LOCATION: (103)..(103)
<223> OTHER INFORMATION: May be any nucleotide
<220> FEATURE:
<221> NAME/KEY: misc_feature
<222> LOCATION: (122)..(122)
<223> OTHER INFORMATION: May be any nucleotide
<220> FEATURE:
<221> NAME/KEY: misc_feature
<222> LOCATION: (205)..(205)
<223> OTHER INFORMATION: May be any nucleotide
<220> FEATURE:
<221> NAME/KEY: misc_feature
<222> LOCATION: (295)..(295)
<223> OTHER INFORMATION: May be any nucleotide
<220> FEATURE:
<221> NAME/KEY: misc_feature
<222> LOCATION: (297)..(297)
<223> OTHER INFORMATION: May be any nucleotide

```
<220> FEATURE:
<221> NAME/KEY: misc_feature
<222> LOCATION: (331)..(331)
<223> OTHER INFORMATION: May be any nucleotide
<220> FEATURE:
<221> NAME/KEY: misc_feature
<222> LOCATION: (357)..(357)
<223> OTHER INFORMATION: May be any nucleotide
<220> FEATURE:
<221> NAME/KEY: misc_feature
<222> LOCATION: (368)..(368)
<223> OTHER INFORMATION: May be any nucleotide
<220> FEATURE:
<221> NAME/KEY: misc_feature
<222> LOCATION: (375)..(375)
<223> OTHER INFORMATION: May be any nucleotide
<220> FEATURE:
<221> NAME/KEY: misc_feature
<222> LOCATION: (386)..(387)
<223> OTHER INFORMATION: May be any nucleotide
<220> FEATURE:
<221> NAME/KEY: misc_feature
<222> LOCATION: (414)..(414)
<223> OTHER INFORMATION: May be any nucleotide
<220> FEATURE:
<221> NAME/KEY: misc_feature
<222> LOCATION: (420)..(420)
<223> OTHER INFORMATION: May be any nucleotide
<220> FEATURE:
<221> NAME/KEY: misc_feature
<222> LOCATION: (425)..(425)
<223> OTHER INFORMATION: May be any nucleotide
<220> FEATURE:
<221> NAME/KEY: misc_feature
<222> LOCATION: (436)..(437)
<223> OTHER INFORMATION: May be any nucleotide
<220> FEATURE:
<221> NAME/KEY: misc_feature
<222> LOCATION: (440)..(441)
<223> OTHER INFORMATION: May be any nucleotide
<220> FEATURE:
<221> NAME/KEY: misc_feature
<222> LOCATION: (445)..(446)
<223> OTHER INFORMATION: May be any nucleotide
<220> FEATURE:
<221> NAME/KEY: misc_feature
<222> LOCATION: (451)..(451)
<223> OTHER INFORMATION: May be any nucleotide
<220> FEATURE:
<221> NAME/KEY: misc_feature
<222> LOCATION: (464)..(464)
<223> OTHER INFORMATION: May be any nucleotide
<220> FEATURE:
<221> NAME/KEY: misc_feature
<222> LOCATION: (466)..(466)
<223> OTHER INFORMATION: May be any nucleotide
<220> FEATURE:
<221> NAME/KEY: misc_feature
<222> LOCATION: (472)..(473)
<223> OTHER INFORMATION: May be any nucleotide
<220> FEATURE:
<221> NAME/KEY: misc_feature
<222> LOCATION: (480)..(480)
<223> OTHER INFORMATION: May be any nucleotide

<400> SEQUENCE: 11
gcagcagctg gacatcgagg gcgagctgcg ccggctcatg gccaagcccg aggctctgaa      60
gtcactgcag gagcggcggc gngagcagga gctgctggag cantacgtga gcaccgtgaa     120
cnaccgcagt gtacatcgtg gactcgctgg acgaggaccg gctccgggga acaagaggag     180
gatcagatgc tgcgggacat gattnagaaa gctgggcctc cagaggaaga agttccaagt    240
ttccgtttgt tccaagatct tggtcaccaa aaagcaaaaa gcagccccctt cccantngtt   300 agcccattag ggcccttggg ttttggcccg naaccttggg aattccggtt tttggganttt   360
```

-continued

| ggggggggncc atggnttttg gccccnnacc cgggaaaccc ggttttttta attnggggggn | 420 |
| ccctnggttt tttggnncgn naccnngaat ntttgggttt tttngntttg gnnaaagggn | 480 |
| tttt | 484 |

<210> SEQ ID NO 12
<211> LENGTH: 321
<212> TYPE: DNA
<213> ORGANISM: Homo sapiens
<220> FEATURE:
<221> NAME/KEY: misc_feature
<222> LOCATION: (38)..(38)
<223> OTHER INFORMATION: May be any nucleotide
<220> FEATURE:
<221> NAME/KEY: misc_feature
<222> LOCATION: (106)..(106)
<223> OTHER INFORMATION: May be any nucleotide
<220> FEATURE:
<221> NAME/KEY: misc_feature
<222> LOCATION: (114)..(114)
<223> OTHER INFORMATION: May be any nucleotide
<220> FEATURE:
<221> NAME/KEY: misc_feature
<222> LOCATION: (116)..(116)
<223> OTHER INFORMATION: May be any nucleotide
<220> FEATURE:
<221> NAME/KEY: misc_feature
<222> LOCATION: (122)..(122)
<223> OTHER INFORMATION: May be any nucleotide
<220> FEATURE:
<221> NAME/KEY: misc_feature
<222> LOCATION: (220)..(220)
<223> OTHER INFORMATION: May be any nucleotide
<220> FEATURE:
<221> NAME/KEY: misc_feature
<222> LOCATION: (229)..(229)
<223> OTHER INFORMATION: May be any nucleotide
<220> FEATURE:
<221> NAME/KEY: misc_feature
<222> LOCATION: (259)..(259)
<223> OTHER INFORMATION: May be any nucleotide
<220> FEATURE:
<221> NAME/KEY: misc_feature
<222> LOCATION: (269)..(269)
<223> OTHER INFORMATION: May be any nucleotide
<220> FEATURE:
<221> NAME/KEY: misc_feature
<222> LOCATION: (287)..(287)
<223> OTHER INFORMATION: May be any nucleotide
<220> FEATURE:
<221> NAME/KEY: misc_feature
<222> LOCATION: (290)..(290)
<223> OTHER INFORMATION: May be any nucleotide
<220> FEATURE:
<221> NAME/KEY: misc_feature
<222> LOCATION: (312)..(314)
<223> OTHER INFORMATION: May be any nucleotide

<400> SEQUENCE: 12

| aggtcatcgg gcagccttcc ctgtgtgcca agccagcntt cgcttctgaa aaccaaactc | 60 |
| cagccgctgc cagtcgggac ttggtcgccc ggcgctgcca gaatgntcca ctgncnaccg | 120 |
| gnccccctgc ctcggtttcc cttctgttta gtggcgacac aggcacccag ctttggggtg | 180 |
| gtgctgacgc tcccaggggt gccaggagcc actgggacan gggtgaggnt cccagacgtt | 240 |
| ccttcgaggt gcccagttnt ccagggagnt tctgggccca aggcgtnttn agggatcttg | 300 |
| ttcctttaaa cnnnccaatt g | 321 |

<210> SEQ ID NO 13
<211> LENGTH: 343
<212> TYPE: DNA
<213> ORGANISM: Homo sapiens

```
<220> FEATURE:
<221> NAME/KEY: misc_feature
<222> LOCATION: (12)..(12)
<223> OTHER INFORMATION: May be any nucleotide
<220> FEATURE:
<221> NAME/KEY: misc_feature
<222> LOCATION: (27)..(27)
<223> OTHER INFORMATION: May be any nucleotide
<220> FEATURE:
<221> NAME/KEY: misc_feature
<222> LOCATION: (40)..(40)
<223> OTHER INFORMATION: May be any nucleotide
<220> FEATURE:
<221> NAME/KEY: misc_feature
<222> LOCATION: (42)..(42)
<223> OTHER INFORMATION: May be any nucleotide
<220> FEATURE:
<221> NAME/KEY: misc_feature
<222> LOCATION: (45)..(45)
<223> OTHER INFORMATION: May be any nucleotide
<220> FEATURE:
<221> NAME/KEY: misc_feature
<222> LOCATION: (75)..(76)
<223> OTHER INFORMATION: May be any nucleotide
<220> FEATURE:
<221> NAME/KEY: misc_feature
<222> LOCATION: (97)..(97)
<223> OTHER INFORMATION: May be any nucleotide
<220> FEATURE:
<221> NAME/KEY: misc_feature
<222> LOCATION: (99)..(99)
<223> OTHER INFORMATION: May be any nucleotide
<220> FEATURE:
<221> NAME/KEY: misc_feature
<222> LOCATION: (101)..(101)
<223> OTHER INFORMATION: May be any nucleotide
<220> FEATURE:
<221> NAME/KEY: misc_feature
<222> LOCATION: (171)..(171)
<223> OTHER INFORMATION: May be any nucleotide
<220> FEATURE:
<221> NAME/KEY: misc_feature
<222> LOCATION: (208)..(208)
<223> OTHER INFORMATION: May be any nucleotide
<220> FEATURE:
<221> NAME/KEY: misc_feature
<222> LOCATION: (210)..(210)
<223> OTHER INFORMATION: May be any nucleotide
<220> FEATURE:
<221> NAME/KEY: misc_feature
<222> LOCATION: (219)..(219)
<223> OTHER INFORMATION: May be any nucleotide
<220> FEATURE:
<221> NAME/KEY: misc_feature
<222> LOCATION: (224)..(224)
<223> OTHER INFORMATION: May be any nucleotide
<220> FEATURE:
<221> NAME/KEY: misc_feature
<222> LOCATION: (236)..(236)
<223> OTHER INFORMATION: May be any nucleotide
<220> FEATURE:
<221> NAME/KEY: misc_feature
<222> LOCATION: (254)..(254)
<223> OTHER INFORMATION: May be any nucleotide
<220> FEATURE:
<221> NAME/KEY: misc_feature
<222> LOCATION: (267)..(267)
<223> OTHER INFORMATION: May be any nucleotide
<220> FEATURE:
<221> NAME/KEY: misc_feature
<222> LOCATION: (269)..(269)
<223> OTHER INFORMATION: May be any nucleotide
<220> FEATURE:
<221> NAME/KEY: misc_feature
<222> LOCATION: (273)..(273)
<223> OTHER INFORMATION: May be any nucleotide
<220> FEATURE:
<221> NAME/KEY: misc_feature
<222> LOCATION: (275)..(276)
```

<220> FEATURE:
<221> NAME/KEY: misc_feature
<222> LOCATION: (289)..(289)
<223> OTHER INFORMATION: May be any nucleotide
<220> FEATURE:
<221> NAME/KEY: misc_feature
<222> LOCATION: (296)..(298)
<223> OTHER INFORMATION: May be any nucleotide
<220> FEATURE:
<221> NAME/KEY: misc_feature
<222> LOCATION: (302)..(302)
<223> OTHER INFORMATION: May be any nucleotide
<220> FEATURE:
<221> NAME/KEY: misc_feature
<222> LOCATION: (304)..(305)
<223> OTHER INFORMATION: May be any nucleotide
<220> FEATURE:
<221> NAME/KEY: misc_feature
<222> LOCATION: (312)..(312)
<223> OTHER INFORMATION: May be any nucleotide
<220> FEATURE:
<221> NAME/KEY: misc_feature
<222> LOCATION: (315)..(315)
<223> OTHER INFORMATION: May be any nucleotide
<220> FEATURE:
<221> NAME/KEY: misc_feature
<222> LOCATION: (318)..(318)
<223> OTHER INFORMATION: May be any nucleotide
<220> FEATURE:
<221> NAME/KEY: misc_feature
<222> LOCATION: (332)..(332)
<223> OTHER INFORMATION: May be any nucleotide

<400> SEQUENCE: 13

```
acgagaacag angatagagg gcatctntcc caggtgaccn tnctnttctg tcccaggagg      60
gtgggtaatt ccctnnggga tggggctccc acacctncnt naggtcccca ctcagaccag     120
caccagtgtc tgcctctgag aatgttggca gctcacagag agcagggccg ncccgggatg     180
gggggcaggt actccccacc ttcctgcntn cgatcctant tctnatccag cgtccncttt     240
attaccgttt tttnactaat gcttctntng agnanngctc tttggaagna ggagcnnnag     300
cntnntggag cntcncanga gatgtttaag gnttattaag ctt                       343
```

<210> SEQ ID NO 14
<211> LENGTH: 480
<212> TYPE: DNA
<213> ORGANISM: Homo sapiens
<220> FEATURE:
<221> NAME/KEY: misc_feature
<222> LOCATION: (16)..(16)
<223> OTHER INFORMATION: May be any nucleotide
<220> FEATURE:
<221> NAME/KEY: misc_feature
<222> LOCATION: (60)..(60)
<223> OTHER INFORMATION: May be any nucleotide
<220> FEATURE:
<221> NAME/KEY: misc_feature
<222> LOCATION: (124)..(124)
<223> OTHER INFORMATION: May be any nucleotide
<220> FEATURE:
<221> NAME/KEY: misc_feature
<222> LOCATION: (155)..(155)
<223> OTHER INFORMATION: May be any nucleotide
<220> FEATURE:
<221> NAME/KEY: misc_feature
<222> LOCATION: (204)..(204)
<223> OTHER INFORMATION: May be any nucleotide
<220> FEATURE:
<221> NAME/KEY: misc_feature
<222> LOCATION: (246)..(246)
<223> OTHER INFORMATION: May be any nucleotide
<220> FEATURE:
<221> NAME/KEY: misc_feature

```
<222> LOCATION: (265)..(265)
<223> OTHER INFORMATION: May be any nucleotide
<220> FEATURE:
<221> NAME/KEY: misc_feature
<222> LOCATION: (269)..(269)
<223> OTHER INFORMATION: May be any nucleotide
<220> FEATURE:
<221> NAME/KEY: misc_feature
<222> LOCATION: (320)..(320)
<223> OTHER INFORMATION: May be any nucleotide
<220> FEATURE:
<221> NAME/KEY: misc_feature
<222> LOCATION: (331)..(331)
<223> OTHER INFORMATION: May be any nucleotide
<220> FEATURE:
<221> NAME/KEY: misc_feature
<222> LOCATION: (377)..(377)
<223> OTHER INFORMATION: May be any nucleotide
<220> FEATURE:
<221> NAME/KEY: misc_feature
<222> LOCATION: (385)..(385)
<223> OTHER INFORMATION: May be any nucleotide
<220> FEATURE:
<221> NAME/KEY: misc_feature
<222> LOCATION: (395)..(396)
<223> OTHER INFORMATION: May be any nucleotide
<220> FEATURE:
<221> NAME/KEY: misc_feature
<222> LOCATION: (398)..(398)
<223> OTHER INFORMATION: May be any nucleotide
<220> FEATURE:
<221> NAME/KEY: misc_feature
<222> LOCATION: (402)..(402)
<223> OTHER INFORMATION: May be any nucleotide
<220> FEATURE:
<221> NAME/KEY: misc_feature
<222> LOCATION: (413)..(413)
<223> OTHER INFORMATION: May be any nucleotide
<220> FEATURE:
<221> NAME/KEY: misc_feature
<222> LOCATION: (431)..(431)
<223> OTHER INFORMATION: May be any nucleotide
<220> FEATURE:
<221> NAME/KEY: misc_feature
<222> LOCATION: (435)..(435)
<223> OTHER INFORMATION: May be any nucleotide
<220> FEATURE:
<221> NAME/KEY: misc_feature
<222> LOCATION: (439)..(441)
<223> OTHER INFORMATION: May be any nucleotide
<220> FEATURE:
<221> NAME/KEY: misc_feature
<222> LOCATION: (453)..(454)
<223> OTHER INFORMATION: May be any nucleotide
<220> FEATURE:
<221> NAME/KEY: misc_feature
<222> LOCATION: (462)..(462)
<223> OTHER INFORMATION: May be any nucleotide

<400> SEQUENCE: 14
acatttggtg tatgtncttg gctgaggtct acttggcttg cctgctttga tcctgagagn      60
cacccacccc atctcacagt gaataggttg gcaggtgtgg gctggcgggt ggactacacc     120
ctgnagctcc agcctgctgc aatccgtgga agagnccatg gtgcacctgc ggctggaggt     180
ggcagctgcc ccagggaccc cagnccagcc tgttgccatg tccctctcag cagacaattc     240
caggtnctcc tggcagaact gaagnaggnc cagaccctga tgagctcctt ggggttgagga    300 gaagggtgtt tccaggcctn tttggagccg ncttgcccgt atggagttaa ggccttttga     360 attgttttg gggaggnaac ctggnttta aggtnntnaa gnccttggcc cgnatttttgg     420 cttccaaatt nccanttgnn naaatttttt ttnngaattt gnttaaggtt tgggactttt    480

<210> SEQ ID NO 15
```

```
<211> LENGTH: 481
<212> TYPE: DNA
<213> ORGANISM: Homo sapiens
<220> FEATURE:
<221> NAME/KEY: misc_feature
<222> LOCATION: (57)..(57)
<223> OTHER INFORMATION: May be any nucleotide
<220> FEATURE:
<221> NAME/KEY: misc_feature
<222> LOCATION: (187)..(187)
<223> OTHER INFORMATION: May be any nucleotide
<220> FEATURE:
<221> NAME/KEY: misc_feature
<222> LOCATION: (223)..(224)
<223> OTHER INFORMATION: May be any nucleotide
<220> FEATURE:
<221> NAME/KEY: misc_feature
<222> LOCATION: (244)..(244)
<223> OTHER INFORMATION: May be any nucleotide
<220> FEATURE:
<221> NAME/KEY: misc_feature
<222> LOCATION: (248)..(248)
<223> OTHER INFORMATION: May be any nucleotide
<220> FEATURE:
<221> NAME/KEY: misc_feature
<222> LOCATION: (251)..(251)
<223> OTHER INFORMATION: May be any nucleotide
<220> FEATURE:
<221> NAME/KEY: misc_feature
<222> LOCATION: (272)..(272)
<223> OTHER INFORMATION: May be any nucleotide
<220> FEATURE:
<221> NAME/KEY: misc_feature
<222> LOCATION: (294)..(294)
<223> OTHER INFORMATION: May be any nucleotide
<220> FEATURE:
<221> NAME/KEY: misc_feature
<222> LOCATION: (297)..(297)
<223> OTHER INFORMATION: May be any nucleotide
<220> FEATURE:
<221> NAME/KEY: misc_feature
<222> LOCATION: (299)..(299)
<223> OTHER INFORMATION: May be any nucleotide
<220> FEATURE:
<221> NAME/KEY: misc_feature
<222> LOCATION: (312)..(312)
<223> OTHER INFORMATION: May be any nucleotide
<220> FEATURE:
<221> NAME/KEY: misc_feature
<222> LOCATION: (328)..(328)
<223> OTHER INFORMATION: May be any nucleotide
<220> FEATURE:
<221> NAME/KEY: misc_feature
<222> LOCATION: (332)..(332)
<223> OTHER INFORMATION: May be any nucleotide
<220> FEATURE:
<221> NAME/KEY: misc_feature
<222> LOCATION: (336)..(336)
<223> OTHER INFORMATION: May be any nucleotide
<220> FEATURE:
<221> NAME/KEY: misc_feature
<222> LOCATION: (340)..(340)
<223> OTHER INFORMATION: May be any nucleotide
<220> FEATURE:
<221> NAME/KEY: misc_feature
<222> LOCATION: (354)..(354)
<223> OTHER INFORMATION: May be any nucleotide
<220> FEATURE:
<221> NAME/KEY: misc_feature
<222> LOCATION: (362)..(362)
<223> OTHER INFORMATION: May be any nucleotide
<220> FEATURE:
<221> NAME/KEY: misc_feature
<222> LOCATION: (367)..(367)
<223> OTHER INFORMATION: May be any nucleotide
<220> FEATURE:
<221> NAME/KEY: misc_feature
<222> LOCATION: (381)..(381)
<223> OTHER INFORMATION: May be any nucleotide
```

```
<220> FEATURE:
<221> NAME/KEY: misc_feature
<222> LOCATION: (383)..(383)
<223> OTHER INFORMATION: May be any nucleotide
<220> FEATURE:
<221> NAME/KEY: misc_feature
<222> LOCATION: (385)..(385)
<223> OTHER INFORMATION: May be any nucleotide
<220> FEATURE:
<221> NAME/KEY: misc_feature
<222> LOCATION: (396)..(396)
<223> OTHER INFORMATION: May be any nucleotide
<220> FEATURE:
<221> NAME/KEY: misc_feature
<222> LOCATION: (404)..(405)
<223> OTHER INFORMATION: May be any nucleotide
<220> FEATURE:
<221> NAME/KEY: misc_feature
<222> LOCATION: (407)..(407)
<223> OTHER INFORMATION: May be any nucleotide
<220> FEATURE:
<221> NAME/KEY: misc_feature
<222> LOCATION: (409)..(410)
<223> OTHER INFORMATION: May be any nucleotide
<220> FEATURE:
<221> NAME/KEY: misc_feature
<222> LOCATION: (412)..(412)
<223> OTHER INFORMATION: May be any nucleotide
<220> FEATURE:
<221> NAME/KEY: misc_feature
<222> LOCATION: (415)..(415)
<223> OTHER INFORMATION: May be any nucleotide
<220> FEATURE:
<221> NAME/KEY: misc_feature
<222> LOCATION: (428)..(429)
<223> OTHER INFORMATION: May be any nucleotide
<220> FEATURE:
<221> NAME/KEY: misc_feature
<222> LOCATION: (431)..(431)
<223> OTHER INFORMATION: May be any nucleotide
<220> FEATURE:
<221> NAME/KEY: misc_feature
<222> LOCATION: (437)..(437)
<223> OTHER INFORMATION: May be any nucleotide
<220> FEATURE:
<221> NAME/KEY: misc_feature
<222> LOCATION: (442)..(442)
<223> OTHER INFORMATION: May be any nucleotide
<220> FEATURE:
<221> NAME/KEY: misc_feature
<222> LOCATION: (459)..(460)
<223> OTHER INFORMATION: May be any nucleotide
<220> FEATURE:
<221> NAME/KEY: misc_feature
<222> LOCATION: (463)..(464)
<223> OTHER INFORMATION: May be any nucleotide

<400> SEQUENCE: 15
agcattgtgg gtaaaggcct ggaggcagga aagtgaagga caatttcaag aaactcngtt      60
catcaatttt catcaacacc ttcctgggcc atgcctgggt actgaggaac ccagccctga     120
atctggacat cattttccct ttcagagcat agaatgcagg gggatccagg aatgggttaa     180
caggagngaa gcttggttca aggagacctt tgcgtaccag ggnnaaggga gttttgaact     240
ttantctnca nggcaggcag agcacgacag gnttcctacc tggggtcaat tcanttntnc     300
tatttctctt antgttgcca tccgtagntc cncggntaan ttggggaggt ttanggcagg     360
gngaatnggt tttgaacccc ngngngttgg gggttngcaa ttgnngntnn gntgngaacc     420
attgaatnng nggcttnggt gntccaggtt gggatcccnn ttnnaaaaaa aaaaaaaaat     480
t                                                                    481

<210> SEQ ID NO 16
```

```
<211> LENGTH: 484
<212> TYPE: DNA
<213> ORGANISM: Homo sapiens
<220> FEATURE:
<221> NAME/KEY: misc_feature
<222> LOCATION: (35)..(35)
<223> OTHER INFORMATION: May be any nucleotide
<220> FEATURE:
<221> NAME/KEY: misc_feature
<222> LOCATION: (47)..(47)
<223> OTHER INFORMATION: May be any nucleotide
<220> FEATURE:
<221> NAME/KEY: misc_feature
<222> LOCATION: (76)..(76)
<223> OTHER INFORMATION: May be any nucleotide
<220> FEATURE:
<221> NAME/KEY: misc_feature
<222> LOCATION: (162)..(162)
<223> OTHER INFORMATION: May be any nucleotide
<220> FEATURE:
<221> NAME/KEY: misc_feature
<222> LOCATION: (310)..(310)
<223> OTHER INFORMATION: May be any nucleotide
<220> FEATURE:
<221> NAME/KEY: misc_feature
<222> LOCATION: (320)..(320)
<223> OTHER INFORMATION: May be any nucleotide
<220> FEATURE:
<221> NAME/KEY: misc_feature
<222> LOCATION: (323)..(323)
<223> OTHER INFORMATION: May be any nucleotide
<220> FEATURE:
<221> NAME/KEY: misc_feature
<222> LOCATION: (357)..(357)
<223> OTHER INFORMATION: May be any nucleotide
<220> FEATURE:
<221> NAME/KEY: misc_feature
<222> LOCATION: (361)..(361)
<223> OTHER INFORMATION: May be any nucleotide
<220> FEATURE:
<221> NAME/KEY: misc_feature
<222> LOCATION: (369)..(369)
<223> OTHER INFORMATION: May be any nucleotide
<220> FEATURE:
<221> NAME/KEY: misc_feature
<222> LOCATION: (379)..(379)
<223> OTHER INFORMATION: May be any nucleotide
<220> FEATURE:
<221> NAME/KEY: misc_feature
<222> LOCATION: (394)..(394)
<223> OTHER INFORMATION: May be any nucleotide
<220> FEATURE:
<221> NAME/KEY: misc_feature
<222> LOCATION: (400)..(400)
<223> OTHER INFORMATION: May be any nucleotide
<220> FEATURE:
<221> NAME/KEY: misc_feature
<222> LOCATION: (406)..(406)
<223> OTHER INFORMATION: May be any nucleotide
<220> FEATURE:
<221> NAME/KEY: misc_feature
<222> LOCATION: (414)..(414)
<223> OTHER INFORMATION: May be any nucleotide
<220> FEATURE:
<221> NAME/KEY: misc_feature
<222> LOCATION: (417)..(417)
<223> OTHER INFORMATION: May be any nucleotide
<220> FEATURE:
<221> NAME/KEY: misc_feature
<222> LOCATION: (438)..(438)
<223> OTHER INFORMATION: May be any nucleotide
<220> FEATURE:
<221> NAME/KEY: misc_feature
<222> LOCATION: (446)..(446)
<223> OTHER INFORMATION: May be any nucleotide
<220> FEATURE:
<221> NAME/KEY: misc_feature
<222> LOCATION: (449)..(449)
<223> OTHER INFORMATION: May be any nucleotide
```

```
<220> FEATURE:
<221> NAME/KEY: misc_feature
<222> LOCATION: (470)..(470)
<223> OTHER INFORMATION: May be any nucleotide

<400> SEQUENCE: 16
gagacgcact ctctagcccg gcagatgaag gcganggcgg cggccgnact tggatgagat       60
tcaccgcgag ctgcgncctc agggatccgc acgaccccag cccgacccaa acgccgagtt      120
cgaccccgac ctgccagggg gcggcctgca ccgctgtctg gnctgcgcga ggtacttcat      180
cgattccacc aacctgaaga cccacttccg atccaaagac cacaagaaaa ggctgaagca      240
gcttgagcgt cgagccctta cagtcaggaa gaggcggaga gggcagcggg gttattggga      300
ttctatgtgn cccccaggn ggnttggcag tgcccacgga agttttccat tgaggtncct      360
nagattggnt aacttttanc tgaaaatggg cttnaagttn caaggnaaaa gganttnccc      420
ctgggcaatt acgaaagntt tagttnggna gggaggtttc aacccttttn cctttggttt      480
tggg                                                                   484

<210> SEQ ID NO 17
<211> LENGTH: 478
<212> TYPE: DNA
<213> ORGANISM: Homo sapiens
<220> FEATURE:
<221> NAME/KEY: misc_feature
<222> LOCATION: (56)..(56)
<223> OTHER INFORMATION: May be any nucleotide
<220> FEATURE:
<221> NAME/KEY: misc_feature
<222> LOCATION: (61)..(61)
<223> OTHER INFORMATION: May be any nucleotide
<220> FEATURE:
<221> NAME/KEY: misc_feature
<222> LOCATION: (129)..(129)
<223> OTHER INFORMATION: May be any nucleotide
<220> FEATURE:
<221> NAME/KEY: misc_feature
<222> LOCATION: (158)..(158)
<223> OTHER INFORMATION: May be any nucleotide
<220> FEATURE:
<221> NAME/KEY: misc_feature
<222> LOCATION: (206)..(206)
<223> OTHER INFORMATION: May be any nucleotide
<220> FEATURE:
<221> NAME/KEY: misc_feature
<222> LOCATION: (262)..(262)
<223> OTHER INFORMATION: May be any nucleotide
<220> FEATURE:
<221> NAME/KEY: misc_feature
<222> LOCATION: (279)..(279)
<223> OTHER INFORMATION: May be any nucleotide
<220> FEATURE:
<221> NAME/KEY: misc_feature
<222> LOCATION: (284)..(284)
<223> OTHER INFORMATION: May be any nucleotide
<220> FEATURE:
<221> NAME/KEY: misc_feature
<222> LOCATION: (292)..(292)
<223> OTHER INFORMATION: May be any nucleotide
<220> FEATURE:
<221> NAME/KEY: misc_feature
<222> LOCATION: (303)..(303)
<223> OTHER INFORMATION: May be any nucleotide
<220> FEATURE:
<221> NAME/KEY: misc_feature
<222> LOCATION: (310)..(310)
<223> OTHER INFORMATION: May be any nucleotide
<220> FEATURE:
<221> NAME/KEY: misc_feature
<222> LOCATION: (339)..(339)
<223> OTHER INFORMATION: May be any nucleotide
<220> FEATURE:
```

```
<221> NAME/KEY: misc_feature
<222> LOCATION: (357)..(358)
<223> OTHER INFORMATION: May be any nucleotide
<220> FEATURE:
<221> NAME/KEY: misc_feature
<222> LOCATION: (361)..(361)
<223> OTHER INFORMATION: May be any nucleotide
<220> FEATURE:
<221> NAME/KEY: misc_feature
<222> LOCATION: (363)..(363)
<223> OTHER INFORMATION: May be any nucleotide
<220> FEATURE:
<221> NAME/KEY: misc_feature
<222> LOCATION: (372)..(372)
<223> OTHER INFORMATION: May be any nucleotide
<220> FEATURE:
<221> NAME/KEY: misc_feature
<222> LOCATION: (387)..(387)
<223> OTHER INFORMATION: May be any nucleotide
<220> FEATURE:
<221> NAME/KEY: misc_feature
<222> LOCATION: (402)..(403)
<223> OTHER INFORMATION: May be any nucleotide
<220> FEATURE:
<221> NAME/KEY: misc_feature
<222> LOCATION: (409)..(409)
<223> OTHER INFORMATION: May be any nucleotide
<220> FEATURE:
<221> NAME/KEY: misc_feature
<222> LOCATION: (423)..(425)
<223> OTHER INFORMATION: May be any nucleotide
<220> FEATURE:
<221> NAME/KEY: misc_feature
<222> LOCATION: (428)..(428)
<223> OTHER INFORMATION: May be any nucleotide
<220> FEATURE:
<221> NAME/KEY: misc_feature
<222> LOCATION: (434)..(435)
<223> OTHER INFORMATION: May be any nucleotide
<220> FEATURE:
<221> NAME/KEY: misc_feature
<222> LOCATION: (439)..(439)
<223> OTHER INFORMATION: May be any nucleotide
<220> FEATURE:
<221> NAME/KEY: misc_feature
<222> LOCATION: (446)..(446)
<223> OTHER INFORMATION: May be any nucleotide
<220> FEATURE:
<221> NAME/KEY: misc_feature
<222> LOCATION: (450)..(450)
<223> OTHER INFORMATION: May be any nucleotide
<220> FEATURE:
<221> NAME/KEY: misc_feature
<222> LOCATION: (454)..(454)
<223> OTHER INFORMATION: May be any nucleotide
<220> FEATURE:
<221> NAME/KEY: misc_feature
<222> LOCATION: (461)..(462)
<223> OTHER INFORMATION: May be any nucleotide
<220> FEATURE:
<221> NAME/KEY: misc_feature
<222> LOCATION: (464)..(464)
<223> OTHER INFORMATION: May be any nucleotide

<400> SEQUENCE: 17
aggcacagct gttgcgtcag gcaaggtcac ctgcatttat ttattgagca gcagtnctgt     60
ntcaggccca ggggccgagc ccctctccct gttccccetat ggtgtctccg aggccctctg    120
ggagggccnc acatctggga gcagcacctc agagtggnac agaaagcatt agcgtgccac    180
gagcttcacc cgacgccgag cctgtnaagg tgggctgatg gtgcccgttt taacccagcg    240
cttcagggag gttcagaatg gnagccgaaa cccagggggnt gttnagcatc ancttctggg    300
agnccttttn tactttttat ggactggttt cctgggaang ggttggttgg gggaagnnca    360
ngnaggcttg gngttccttt agggttnggg gggcctgttt tnncattcna acccaagctt    420
```
ttnnnttnca tttnncttnt tttttngggn ggcnagtaaa nngntccaag gttttttt    478

<210> SEQ ID NO 18
<211> LENGTH: 480
<212> TYPE: DNA
<213> ORGANISM: Homo sapiens
<220> FEATURE:
<221> NAME/KEY: misc_feature
<222> LOCATION: (85)..(85)
<223> OTHER INFORMATION: May be any nucleotide
<220> FEATURE:
<221> NAME/KEY: misc_feature
<222> LOCATION: (90)..(90)
<223> OTHER INFORMATION: May be any nucleotide
<220> FEATURE:
<221> NAME/KEY: misc_feature
<222> LOCATION: (94)..(94)
<223> OTHER INFORMATION: May be any nucleotide
<220> FEATURE:
<221> NAME/KEY: misc_feature
<222> LOCATION: (274)..(275)
<223> OTHER INFORMATION: May be any nucleotide
<220> FEATURE:
<221> NAME/KEY: misc_feature
<222> LOCATION: (285)..(285)
<223> OTHER INFORMATION: May be any nucleotide
<220> FEATURE:
<221> NAME/KEY: misc_feature
<222> LOCATION: (292)..(292)
<223> OTHER INFORMATION: May be any nucleotide
<220> FEATURE:
<221> NAME/KEY: misc_feature
<222> LOCATION: (300)..(300)
<223> OTHER INFORMATION: May be any nucleotide
<220> FEATURE:
<221> NAME/KEY: misc_feature
<222> LOCATION: (309)..(309)
<223> OTHER INFORMATION: May be any nucleotide
<220> FEATURE:
<221> NAME/KEY: misc_feature
<222> LOCATION: (321)..(321)
<223> OTHER INFORMATION: May be any nucleotide
<220> FEATURE:
<221> NAME/KEY: misc_feature
<222> LOCATION: (323)..(324)
<223> OTHER INFORMATION: May be any nucleotide
<220> FEATURE:
<221> NAME/KEY: misc_feature
<222> LOCATION: (330)..(330)
<223> OTHER INFORMATION: May be any nucleotide
<220> FEATURE:
<221> NAME/KEY: misc_feature
<222> LOCATION: (332)..(332)
<223> OTHER INFORMATION: May be any nucleotide
<220> FEATURE:
<221> NAME/KEY: misc_feature
<222> LOCATION: (342)..(342)
<223> OTHER INFORMATION: May be any nucleotide
<220> FEATURE:
<221> NAME/KEY: misc_feature
<222> LOCATION: (347)..(347)
<223> OTHER INFORMATION: May be any nucleotide
<220> FEATURE:
<221> NAME/KEY: misc_feature
<222> LOCATION: (349)..(350)
<223> OTHER INFORMATION: May be any nucleotide
<220> FEATURE:
<221> NAME/KEY: misc_feature
<222> LOCATION: (356)..(356)
<223> OTHER INFORMATION: May be any nucleotide
<220> FEATURE:
<221> NAME/KEY: misc_feature
<222> LOCATION: (360)..(360)
<223> OTHER INFORMATION: May be any nucleotide
<220> FEATURE:
<221> NAME/KEY: misc_feature
<222> LOCATION: (373)..(374)

<223> OTHER INFORMATION: May be any nucleotide
<220> FEATURE:
<221> NAME/KEY: misc_feature
<222> LOCATION: (376)..(376)
<223> OTHER INFORMATION: May be any nucleotide
<220> FEATURE:
<221> NAME/KEY: misc_feature
<222> LOCATION: (390)..(390)
<223> OTHER INFORMATION: May be any nucleotide
<220> FEATURE:
<221> NAME/KEY: misc_feature
<222> LOCATION: (392)..(392)
<223> OTHER INFORMATION: May be any nucleotide
<220> FEATURE:
<221> NAME/KEY: misc_feature
<222> LOCATION: (402)..(402)
<223> OTHER INFORMATION: May be any nucleotide
<220> FEATURE:
<221> NAME/KEY: misc_feature
<222> LOCATION: (408)..(408)
<223> OTHER INFORMATION: May be any nucleotide
<220> FEATURE:
<221> NAME/KEY: misc_feature
<222> LOCATION: (411)..(411)
<223> OTHER INFORMATION: May be any nucleotide
<220> FEATURE:
<221> NAME/KEY: misc_feature
<222> LOCATION: (413)..(413)
<223> OTHER INFORMATION: May be any nucleotide
<220> FEATURE:
<221> NAME/KEY: misc_feature
<222> LOCATION: (430)..(430)
<223> OTHER INFORMATION: May be any nucleotide
<220> FEATURE:
<221> NAME/KEY: misc_feature
<222> LOCATION: (433)..(434)
<223> OTHER INFORMATION: May be any nucleotide
<220> FEATURE:
<221> NAME/KEY: misc_feature
<222> LOCATION: (442)..(442)
<223> OTHER INFORMATION: May be any nucleotide
<220> FEATURE:
<221> NAME/KEY: misc_feature
<222> LOCATION: (449)..(449)
<223> OTHER INFORMATION: May be any nucleotide
<220> FEATURE:
<221> NAME/KEY: misc_feature
<222> LOCATION: (470)..(470)
<223> OTHER INFORMATION: May be any nucleotide

<400> SEQUENCE: 18

```
gggccacagc tgctcctgcg cctgggcctt acttcctacc gagacttcct gggcaccaac     60
tggtccagct cagctgcctg gctgngacan aagntgacca ccgactgggg tgacacgcag    120
gcctatctgg cggacccact gggggtgggg cgctgcacta gccacagccg atggacttcc    180
ttgttttcct gcgccgctcc cggcaggtgg gctgaggccc ctgggctggt gggacgtaac    240
tggtggggca acctgagcct caggtggaac ctgnncgttg gttnaacct gnaggcaagn     300 ccttgttnt tgggaattg ncnnaaaatn gnggaccaat gnttggncnn agccanttgn      360 ccgattttt atnntnccaa ttgaaagttn gnatttttg gnggaaantt ngnggaagga     420
atttaacttn ganngggggg gnacccgang ggccaaaggg gttttaaaan gaattttttg   480
```

<210> SEQ ID NO 19
<211> LENGTH: 285
<212> TYPE: DNA
<213> ORGANISM: Homo sapiens
<220> FEATURE:
<221> NAME/KEY: misc_feature
<222> LOCATION: (85)..(85)
<223> OTHER INFORMATION: May be any nucleotide
<220> FEATURE:
<221> NAME/KEY: misc_feature
<222> LOCATION: (186)..(186)
<223> OTHER INFORMATION: May be any nucleotide
<220> FEATURE:
<221> NAME/KEY: misc_feature
<222> LOCATION: (190)..(190)
<223> OTHER INFORMATION: May be any nucleotide
<220> FEATURE:
<221> NAME/KEY: misc_feature
<222> LOCATION: (210)..(212)
<223> OTHER INFORMATION: May be any nucleotide
<220> FEATURE:
<221> NAME/KEY: misc_feature
<222> LOCATION: (214)..(214)
<223> OTHER INFORMATION: May be any nucleotide
<220> FEATURE:
<221> NAME/KEY: misc_feature
<222> LOCATION: (218)..(218)
<223> OTHER INFORMATION: May be any nucleotide
<220> FEATURE:
<221> NAME/KEY: misc_feature
<222> LOCATION: (221)..(221)
<223> OTHER INFORMATION: May be any nucleotide
<220> FEATURE:
<221> NAME/KEY: misc_feature
<222> LOCATION: (226)..(226)
<223> OTHER INFORMATION: May be any nucleotide
<220> FEATURE:
<221> NAME/KEY: misc_feature
<222> LOCATION: (230)..(230)
<223> OTHER INFORMATION: May be any nucleotide
<220> FEATURE:
<221> NAME/KEY: misc_feature
<222> LOCATION: (234)..(234)
<223> OTHER INFORMATION: May be any nucleotide
<220> FEATURE:
<221> NAME/KEY: misc_feature
<222> LOCATION: (238)..(238)
<223> OTHER INFORMATION: May be any nucleotide
<220> FEATURE:
<221> NAME/KEY: misc_feature
<222> LOCATION: (250)..(250)
<223> OTHER INFORMATION: May be any nucleotide
<220> FEATURE:
<221> NAME/KEY: misc_feature
<222> LOCATION: (252)..(252)
<223> OTHER INFORMATION: May be any nucleotide
<220> FEATURE:
<221> NAME/KEY: misc_feature
<222> LOCATION: (265)..(265)
<223> OTHER INFORMATION: May be any nucleotide
<220> FEATURE:
<221> NAME/KEY: misc_feature
<222> LOCATION: (271)..(271)
<223> OTHER INFORMATION: May be any nucleotide

<400> SEQUENCE: 19
agccactctg agctcccacg agaaacactg cttctccagg cccggggttg ttggggagag    60
aggcagaggc agctggagcg ccgtntctct cctgctgggg acaacgtttg ggctttgggt   120
attgactgag tggctgacag ttatctttgc aaccccaaac tggctttggg gccaggacaa   180
ggggtnggcn tttatggtgg tccaagttttn nntncttncc naactngggn ttgntccntg   240
actgttggan cntgttaatt ggctntttca ntgggtttta ttttt                   285

<210> SEQ ID NO 20
<211> LENGTH: 419
<212> TYPE: DNA
<213> ORGANISM: Homo sapiens
<220> FEATURE:
<221> NAME/KEY: misc_feature
<222> LOCATION: (124)..(124)
<223> OTHER INFORMATION: May be any nucleotide
<220> FEATURE:
<221> NAME/KEY: misc_feature
<222> LOCATION: (187)..(187)

```
<223> OTHER INFORMATION: May be any nucleotide
<220> FEATURE:
<221> NAME/KEY: misc_feature
<222> LOCATION: (207)..(207)
<223> OTHER INFORMATION: May be any nucleotide
<220> FEATURE:
<221> NAME/KEY: misc_feature
<222> LOCATION: (222)..(222)
<223> OTHER INFORMATION: May be any nucleotide
<220> FEATURE:
<221> NAME/KEY: misc_feature
<222> LOCATION: (257)..(257)
<223> OTHER INFORMATION: May be any nucleotide
<220> FEATURE:
<221> NAME/KEY: misc_feature
<222> LOCATION: (267)..(267)
<223> OTHER INFORMATION: May be any nucleotide
<220> FEATURE:
<221> NAME/KEY: misc_feature
<222> LOCATION: (296)..(296)
<223> OTHER INFORMATION: May be any nucleotide
<220> FEATURE:
<221> NAME/KEY: misc_feature
<222> LOCATION: (321)..(321)
<223> OTHER INFORMATION: May be any nucleotide
<220> FEATURE:
<221> NAME/KEY: misc_feature
<222> LOCATION: (327)..(327)
<223> OTHER INFORMATION: May be any nucleotide
<220> FEATURE:
<221> NAME/KEY: misc_feature
<222> LOCATION: (332)..(332)
<223> OTHER INFORMATION: May be any nucleotide
<220> FEATURE:
<221> NAME/KEY: misc_feature
<222> LOCATION: (353)..(356)
<223> OTHER INFORMATION: May be any nucleotide
<220> FEATURE:
<221> NAME/KEY: misc_feature
<222> LOCATION: (359)..(359)
<223> OTHER INFORMATION: May be any nucleotide
<220> FEATURE:
<221> NAME/KEY: misc_feature
<222> LOCATION: (363)..(365)
<223> OTHER INFORMATION: May be any nucleotide
<220> FEATURE:
<221> NAME/KEY: misc_feature
<222> LOCATION: (368)..(369)
<223> OTHER INFORMATION: May be any nucleotide
<220> FEATURE:
<221> NAME/KEY: misc_feature
<222> LOCATION: (371)..(371)
<223> OTHER INFORMATION: May be any nucleotide
<220> FEATURE:
<221> NAME/KEY: misc_feature
<222> LOCATION: (374)..(374)
<223> OTHER INFORMATION: May be any nucleotide
<220> FEATURE:
<221> NAME/KEY: misc_feature
<222> LOCATION: (389)..(389)
<223> OTHER INFORMATION: May be any nucleotide

<400> SEQUENCE: 20
ccccgttcgc cccctgcaag cgcgcccgct tcgaggactt ctgcccggac tcgtccccgg      60
agcgtccaac atctcaaact tgatctccat ctttggctcc ggcttctcgg ggctggtgag     120
ccgnacagcc ggactcctcg gagcagccgc cgccgctcaa cgggcagctg tgcgccaagc     180
aggcgtncgc cagcctcggc gcctggnact cgagccattg tngccttcta gggaccccg      240 aggggcacag gggaccnggg gccccgnggg ggttggggc cagacaaaga tttggnaaag     300
gggcgagagg agggaacgag nggggncgg gncaattggg ggtttaatttt ggnnnnaang     360 ggnnnaanng nttntttttt tttaaaattnt taaaaaaaaa aaaaaaatt ttgggggg      419
```

-continued

```
<210> SEQ ID NO 21
<211> LENGTH: 328
<212> TYPE: DNA
<213> ORGANISM: Homo sapiens
<220> FEATURE:
<221> NAME/KEY: misc_feature
<222> LOCATION: (4)..(4)
<223> OTHER INFORMATION: May be any nucleotide
<220> FEATURE:
<221> NAME/KEY: misc_feature
<222> LOCATION: (43)..(43)
<223> OTHER INFORMATION: May be any nucleotide
<220> FEATURE:
<221> NAME/KEY: misc_feature
<222> LOCATION: (96)..(96)
<223> OTHER INFORMATION: May be any nucleotide
<220> FEATURE:
<221> NAME/KEY: misc_feature
<222> LOCATION: (118)..(119)
<223> OTHER INFORMATION: May be any nucleotide
<220> FEATURE:
<221> NAME/KEY: misc_feature
<222> LOCATION: (144)..(144)
<223> OTHER INFORMATION: May be any nucleotide
<220> FEATURE:
<221> NAME/KEY: misc_feature
<222> LOCATION: (172)..(172)
<223> OTHER INFORMATION: May be any nucleotide
<220> FEATURE:
<221> NAME/KEY: misc_feature
<222> LOCATION: (281)..(282)
<223> OTHER INFORMATION: May be any nucleotide
<220> FEATURE:
<221> NAME/KEY: misc_feature
<222> LOCATION: (300)..(300)
<223> OTHER INFORMATION: May be any nucleotide
<220> FEATURE:
<221> NAME/KEY: misc_feature
<222> LOCATION: (305)..(305)
<223> OTHER INFORMATION: May be any nucleotide
<220> FEATURE:
<221> NAME/KEY: misc_feature
<222> LOCATION: (308)..(308)
<223> OTHER INFORMATION: May be any nucleotide
<220> FEATURE:
<221> NAME/KEY: misc_feature
<222> LOCATION: (315)..(315)
<223> OTHER INFORMATION: May be any nucleotide

<400> SEQUENCE: 21
agtntcatac cgccaaccac cgctggctgg gaggagtcgg agntgagaac ctacacagag      60
gtggtgacag agtttgggac cgaggtggag cccganttttg ggaccaaggt ggagcccnng    120
tttgagaccc agttggagcc tganttttgag acccagctgg aacccgagtt tnaggaagag   180
gaggaggagg agaaagagga ggagatagcc actggccagg cattcccctt cacaacagta    240
gagacctaca cagtgaactt ttggggactt tttgagatca nngtcctacc agaccccagn   300
ccaanttnag gtttnagcag caggattt                                         328

<210> SEQ ID NO 22
<211> LENGTH: 524
<212> TYPE: DNA
<213> ORGANISM: Homo sapiens
<220> FEATURE:
<221> NAME/KEY: misc_feature
<222> LOCATION: (24)..(24)
<223> OTHER INFORMATION: May be any nucleotide
<220> FEATURE:
<221> NAME/KEY: misc_feature
<222> LOCATION: (94)..(94)
<223> OTHER INFORMATION: May be any nucleotide
<220> FEATURE:
<221> NAME/KEY: misc_feature
<222> LOCATION: (140)..(140)
```

-continued

```
<223> OTHER INFORMATION: May be any nucleotide
<220> FEATURE:
<221> NAME/KEY: misc_feature
<222> LOCATION: (146)..(146)
<223> OTHER INFORMATION: May be any nucleotide
<220> FEATURE:
<221> NAME/KEY: misc_feature
<222> LOCATION: (266)..(266)
<223> OTHER INFORMATION: May be any nucleotide
<220> FEATURE:
<221> NAME/KEY: misc_feature
<222> LOCATION: (271)..(271)
<223> OTHER INFORMATION: May be any nucleotide
<220> FEATURE:
<221> NAME/KEY: misc_feature
<222> LOCATION: (288)..(288)
<223> OTHER INFORMATION: May be any nucleotide
<220> FEATURE:
<221> NAME/KEY: misc_feature
<222> LOCATION: (292)..(292)
<223> OTHER INFORMATION: May be any nucleotide
<220> FEATURE:
<221> NAME/KEY: misc_feature
<222> LOCATION: (295)..(295)
<223> OTHER INFORMATION: May be any nucleotide
<220> FEATURE:
<221> NAME/KEY: misc_feature
<222> LOCATION: (298)..(298)
<223> OTHER INFORMATION: May be any nucleotide
<220> FEATURE:
<221> NAME/KEY: misc_feature
<222> LOCATION: (301)..(301)
<223> OTHER INFORMATION: May be any nucleotide
<220> FEATURE:
<221> NAME/KEY: misc_feature
<222> LOCATION: (304)..(304)
<223> OTHER INFORMATION: May be any nucleotide
<220> FEATURE:
<221> NAME/KEY: misc_feature
<222> LOCATION: (306)..(306)
<223> OTHER INFORMATION: May be any nucleotide
<220> FEATURE:
<221> NAME/KEY: misc_feature
<222> LOCATION: (311)..(311)
<223> OTHER INFORMATION: May be any nucleotide
<220> FEATURE:
<221> NAME/KEY: misc_feature
<222> LOCATION: (315)..(315)
<223> OTHER INFORMATION: May be any nucleotide
<220> FEATURE:
<221> NAME/KEY: misc_feature
<222> LOCATION: (323)..(323)
<223> OTHER INFORMATION: May be any nucleotide
<220> FEATURE:
<221> NAME/KEY: misc_feature
<222> LOCATION: (327)..(327)
<223> OTHER INFORMATION: May be any nucleotide
<220> FEATURE:
<221> NAME/KEY: misc_feature
<222> LOCATION: (331)..(331)
<223> OTHER INFORMATION: May be any nucleotide
<220> FEATURE:
<221> NAME/KEY: misc_feature
<222> LOCATION: (337)..(337)
<223> OTHER INFORMATION: May be any nucleotide
<220> FEATURE:
<221> NAME/KEY: misc_feature
<222> LOCATION: (359)..(360)
<223> OTHER INFORMATION: May be any nucleotide
<220> FEATURE:
<221> NAME/KEY: misc_feature
<222> LOCATION: (365)..(365)
<223> OTHER INFORMATION: May be any nucleotide
<220> FEATURE:
<221> NAME/KEY: misc_feature
<222> LOCATION: (377)..(377)
<223> OTHER INFORMATION: May be any nucleotide
<220> FEATURE:
<221> NAME/KEY: misc_feature
```

```
<222> LOCATION: (381)..(381)
<223> OTHER INFORMATION: May be any nucleotide
<220> FEATURE:
<221> NAME/KEY: misc_feature
<222> LOCATION: (387)..(387)
<223> OTHER INFORMATION: May be any nucleotide
<220> FEATURE:
<221> NAME/KEY: misc_feature
<222> LOCATION: (402)..(403)
<223> OTHER INFORMATION: May be any nucleotide
<220> FEATURE:
<221> NAME/KEY: misc_feature
<222> LOCATION: (406)..(406)
<223> OTHER INFORMATION: May be any nucleotide
<220> FEATURE:
<221> NAME/KEY: misc_feature
<222> LOCATION: (411)..(413)
<223> OTHER INFORMATION: May be any nucleotide
<220> FEATURE:
<221> NAME/KEY: misc_feature
<222> LOCATION: (434)..(435)
<223> OTHER INFORMATION: May be any nucleotide
<220> FEATURE:
<221> NAME/KEY: misc_feature
<222> LOCATION: (454)..(454)
<223> OTHER INFORMATION: May be any nucleotide
<220> FEATURE:
<221> NAME/KEY: misc_feature
<222> LOCATION: (461)..(461)
<223> OTHER INFORMATION: May be any nucleotide
<220> FEATURE:
<221> NAME/KEY: misc_feature
<222> LOCATION: (464)..(464)
<223> OTHER INFORMATION: May be any nucleotide
<220> FEATURE:
<221> NAME/KEY: misc_feature
<222> LOCATION: (466)..(466)
<223> OTHER INFORMATION: May be any nucleotide
<220> FEATURE:
<221> NAME/KEY: misc_feature
<222> LOCATION: (476)..(477)
<223> OTHER INFORMATION: May be any nucleotide
<220> FEATURE:
<221> NAME/KEY: misc_feature
<222> LOCATION: (499)..(501)
<223> OTHER INFORMATION: May be any nucleotide
<220> FEATURE:
<221> NAME/KEY: misc_feature
<222> LOCATION: (514)..(514)
<223> OTHER INFORMATION: May be any nucleotide

<400> SEQUENCE: 22
agggcagaag ccatggccca tgtntgcaca tccagggagg aggacagaag gcccagctca      60
catgtgagtc ctggcagaag ccatggccca tgtntgcaca tccagggagg aggacagaag     120
gcccagctca catgtgagtn cctggncaga agccatggcc catgtttgca catccaggga    180
ggaggacaga aggcccagc tcacatgtga gttcctggca gaagccatgg cccatgtttg     240
cacatccagg gaggaggaca gaaggnccag ntcagtggcc ctggccgnca anttntantt    300
ntangnccga ncagnagggt agntagnctt ntttggngtg tgttccaatt ccgtatttnn    360
ggttnggttt ttggggncca nttcaanaat tggtttgggg tnnttnttttt nnntttaatt    420 aaagttttaa cttnnaaaaa aaaaaaaaaa tttgggggg nttngnattt tttttnnttt     480
ttgggggggt tttaaattnn ncaagtgaaa tgtnttaaat tttg                     524

<210> SEQ ID NO 23
<211> LENGTH: 490
<212> TYPE: DNA
<213> ORGANISM: Homo sapiens
<220> FEATURE:
<221> NAME/KEY: misc_feature
<222> LOCATION: (4)..(4)
```

```
<223> OTHER INFORMATION: May be any nucleotide
<220> FEATURE:
<221> NAME/KEY: misc_feature
<222> LOCATION: (72)..(72)
<223> OTHER INFORMATION: May be any nucleotide
<220> FEATURE:
<221> NAME/KEY: misc_feature
<222> LOCATION: (202)..(202)
<223> OTHER INFORMATION: May be any nucleotide
<220> FEATURE:
<221> NAME/KEY: misc_feature
<222> LOCATION: (210)..(210)
<223> OTHER INFORMATION: May be any nucleotide
<220> FEATURE:
<221> NAME/KEY: misc_feature
<222> LOCATION: (218)..(218)
<223> OTHER INFORMATION: May be any nucleotide
<220> FEATURE:
<221> NAME/KEY: misc_feature
<222> LOCATION: (254)..(254)
<223> OTHER INFORMATION: May be any nucleotide
<220> FEATURE:
<221> NAME/KEY: misc_feature
<222> LOCATION: (270)..(270)
<223> OTHER INFORMATION: May be any nucleotide
<220> FEATURE:
<221> NAME/KEY: misc_feature
<222> LOCATION: (280)..(280)
<223> OTHER INFORMATION: May be any nucleotide
<220> FEATURE:
<221> NAME/KEY: misc_feature
<222> LOCATION: (298)..(298)
<223> OTHER INFORMATION: May be any nucleotide
<220> FEATURE:
<221> NAME/KEY: misc_feature
<222> LOCATION: (309)..(309)
<223> OTHER INFORMATION: May be any nucleotide
<220> FEATURE:
<221> NAME/KEY: misc_feature
<222> LOCATION: (311)..(311)
<223> OTHER INFORMATION: May be any nucleotide
<220> FEATURE:
<221> NAME/KEY: misc_feature
<222> LOCATION: (317)..(317)
<223> OTHER INFORMATION: May be any nucleotide
<220> FEATURE:
<221> NAME/KEY: misc_feature
<222> LOCATION: (324)..(324)
<223> OTHER INFORMATION: May be any nucleotide
<220> FEATURE:
<221> NAME/KEY: misc_feature
<222> LOCATION: (326)..(326)
<223> OTHER INFORMATION: May be any nucleotide
<220> FEATURE:
<221> NAME/KEY: misc_feature
<222> LOCATION: (330)..(330)
<223> OTHER INFORMATION: May be any nucleotide
<220> FEATURE:
<221> NAME/KEY: misc_feature
<222> LOCATION: (345)..(345)
<223> OTHER INFORMATION: May be any nucleotide
<220> FEATURE:
<221> NAME/KEY: misc_feature
<222> LOCATION: (350)..(350)
<223> OTHER INFORMATION: May be any nucleotide
<220> FEATURE:
<221> NAME/KEY: misc_feature
<222> LOCATION: (356)..(356)
<223> OTHER INFORMATION: May be any nucleotide
<220> FEATURE:
<221> NAME/KEY: misc_feature
<222> LOCATION: (375)..(375)
<223> OTHER INFORMATION: May be any nucleotide
<220> FEATURE:
<221> NAME/KEY: misc_feature
<222> LOCATION: (380)..(380)
<223> OTHER INFORMATION: May be any nucleotide
<220> FEATURE:
<221> NAME/KEY: misc_feature
```

```
<222> LOCATION: (384)..(384)
<223> OTHER INFORMATION: May be any nucleotide
<220> FEATURE:
<221> NAME/KEY: misc_feature
<222> LOCATION: (391)..(391)
<223> OTHER INFORMATION: May be any nucleotide
<220> FEATURE:
<221> NAME/KEY: misc_feature
<222> LOCATION: (428)..(428)
<223> OTHER INFORMATION: May be any nucleotide
<220> FEATURE:
<221> NAME/KEY: misc_feature
<222> LOCATION: (442)..(442)
<223> OTHER INFORMATION: May be any nucleotide
<220> FEATURE:
<221> NAME/KEY: misc_feature
<222> LOCATION: (446)..(446)
<223> OTHER INFORMATION: May be any nucleotide
<220> FEATURE:
<221> NAME/KEY: misc_feature
<222> LOCATION: (449)..(450)
<223> OTHER INFORMATION: May be any nucleotide
<220> FEATURE:
<221> NAME/KEY: misc_feature
<222> LOCATION: (453)..(453)
<223> OTHER INFORMATION: May be any nucleotide
<220> FEATURE:
<221> NAME/KEY: misc_feature
<222> LOCATION: (456)..(456)
<223> OTHER INFORMATION: May be any nucleotide
<220> FEATURE:
<221> NAME/KEY: misc_feature
<222> LOCATION: (458)..(458)
<223> OTHER INFORMATION: May be any nucleotide
<220> FEATURE:
<221> NAME/KEY: misc_feature
<222> LOCATION: (469)..(469)
<223> OTHER INFORMATION: May be any nucleotide

<400> SEQUENCE: 23
aggngccctc ctgagcaaga tccacctgta cacacgcggc tgccacagcg accagagcct      60
tagccatctg tntgtcactg aagcagagat gctcagggac ccagaggtag gccagcaact     120
gctgcgggac tctggagcgt gagaaccagc gcctggaggc tgtcctggcg tggcggcgct     180
ctgagctggt cttctggcgg angcaggcgn gcggcctngg aggcaaggct tgaggctgtt     240
gacgggggcc aaanttgagt tccgcgcggn gggcctttn gggaaggttt ttgaaaanga     300
gcttggagnt ntacaanatt tttngnagcn aaaagttggc cccgnccaan cccatnggca     360
aaaacgtttg tttanaaggn aagntttggg naaaaaggga cccggactt gggaaatttt     420 tgttattnaa aacctttagg gnccanagnn ttnttngngg gtttaatng gtttaaaggc     480 aattttgaaa                                                            490

<210> SEQ ID NO 24
<211> LENGTH: 320
<212> TYPE: DNA
<213> ORGANISM: Homo sapiens
<220> FEATURE:
<221> NAME/KEY: misc_feature
<222> LOCATION: (3)..(3)
<223> OTHER INFORMATION: May be any nucleotide
<220> FEATURE:
<221> NAME/KEY: misc_feature
<222> LOCATION: (6)..(6)
<223> OTHER INFORMATION: May be any nucleotide
<220> FEATURE:
<221> NAME/KEY: misc_feature
<222> LOCATION: (8)..(8)
<223> OTHER INFORMATION: May be any nucleotide
<220> FEATURE:
<221> NAME/KEY: misc_feature
<222> LOCATION: (13)..(13)
```

```
<223> OTHER INFORMATION: May be any nucleotide
<220> FEATURE:
<221> NAME/KEY: misc_feature
<222> LOCATION: (18)..(18)
<223> OTHER INFORMATION: May be any nucleotide
<220> FEATURE:
<221> NAME/KEY: misc_feature
<222> LOCATION: (27)..(27)
<223> OTHER INFORMATION: May be any nucleotide
<220> FEATURE:
<221> NAME/KEY: misc_feature
<222> LOCATION: (37)..(37)
<223> OTHER INFORMATION: May be any nucleotide
<220> FEATURE:
<221> NAME/KEY: misc_feature
<222> LOCATION: (43)..(43)
<223> OTHER INFORMATION: May be any nucleotide
<220> FEATURE:
<221> NAME/KEY: misc_feature
<222> LOCATION: (47)..(48)
<223> OTHER INFORMATION: May be any nucleotide
<220> FEATURE:
<221> NAME/KEY: misc_feature
<222> LOCATION: (70)..(70)
<223> OTHER INFORMATION: May be any nucleotide
<220> FEATURE:
<221> NAME/KEY: misc_feature
<222> LOCATION: (73)..(73)
<223> OTHER INFORMATION: May be any nucleotide
<220> FEATURE:
<221> NAME/KEY: misc_feature
<222> LOCATION: (79)..(79)
<223> OTHER INFORMATION: May be any nucleotide
<220> FEATURE:
<221> NAME/KEY: misc_feature
<222> LOCATION: (86)..(86)
<223> OTHER INFORMATION: May be any nucleotide
<220> FEATURE:
<221> NAME/KEY: misc_feature
<222> LOCATION: (96)..(96)
<223> OTHER INFORMATION: May be any nucleotide
<220> FEATURE:
<221> NAME/KEY: misc_feature
<222> LOCATION: (97)..(97)
<223> OTHER INFORMATION: May be any nucleotide
<220> FEATURE:
<221> NAME/KEY: misc_feature
<222> LOCATION: (107)..(107)
<223> OTHER INFORMATION: May be any nucleotide
<220> FEATURE:
<221> NAME/KEY: misc_feature
<222> LOCATION: (110)..(114)
<223> OTHER INFORMATION: May be any nucleotide
<220> FEATURE:
<221> NAME/KEY: misc_feature
<222> LOCATION: (122)..(122)
<223> OTHER INFORMATION: May be any nucleotide
<220> FEATURE:
<221> NAME/KEY: misc_feature
<222> LOCATION: (124)..(124)
<223> OTHER INFORMATION: May be any nucleotide
<220> FEATURE:
<221> NAME/KEY: misc_feature
<222> LOCATION: (137)..(137)
<223> OTHER INFORMATION: May be any nucleotide
<220> FEATURE:
<221> NAME/KEY: misc_feature
<222> LOCATION: (204)..(204)
<223> OTHER INFORMATION: May be any nucleotide
<220> FEATURE:
<221> NAME/KEY: misc_feature
<222> LOCATION: (218)..(218)
<223> OTHER INFORMATION: May be any nucleotide
<220> FEATURE:
<221> NAME/KEY: misc_feature
<222> LOCATION: (258)..(258)
<223> OTHER INFORMATION: May be any nucleotide
<220> FEATURE:
<221> NAME/KEY: misc_feature
```

```
<222> LOCATION: (282)..(282)
<223> OTHER INFORMATION: May be any nucleotide

<400> SEQUENCE: 24
cangcntntc cangaccntg gacctcncct ggccagnctg ganaccnnca tcgtccctat     60
cagtggagtn gcnttacang gcactngcgc gtcganntac atcgccnggn nnnntatcca    120
tntnaactga tgctggngca tcaaacccgc agctgttcgc gcttatgggc acccgggcag    180
gcatcgccag ggaagctgga gctngtggag cagcagtntc ggctggagca gctgagtgcg    240
gcagagctgc agagcagnaa ccagggccac tgggctgact gnctacagcg tacagagccc    300
ggttggacaa ggacctggaa                                                320

<210> SEQ ID NO 25
<211> LENGTH: 21
<212> TYPE: DNA
<213> ORGANISM: Artificial Sequence
<220> FEATURE:
<223> OTHER INFORMATION: Oligonucleotide

<400> SEQUENCE: 25
gccaccatgg atgttttcaa g                                               21

<210> SEQ ID NO 26
<211> LENGTH: 28
<212> TYPE: DNA
<213> ORGANISM: Artificial Sequence
<220> FEATURE:
<223> OTHER INFORMATION: Oligonucleotide

<400> SEQUENCE: 26
gcgcagatct gtctccccca ctctgggc                                        28

<210> SEQ ID NO 27
<211> LENGTH: 18
<212> TYPE: DNA
<213> ORGANISM: Artificial Sequence
<220> FEATURE:
<223> OTHER INFORMATION: Oligonucleotide

<400> SEQUENCE: 27
atgcttccgg ctcgtatg                                                   18

<210> SEQ ID NO 28
<211> LENGTH: 19
<212> TYPE: DNA
<213> ORGANISM: Artificial Sequence
<220> FEATURE:
<223> OTHER INFORMATION: Oligonucleotide

<400> SEQUENCE: 28
gggttttccc agtcacgac                                                  19

<210> SEQ ID NO 29
<211> LENGTH: 36
<212> TYPE: DNA
<213> ORGANISM: Artificial Sequence
<220> FEATURE:
<223> OTHER INFORMATION: Oligonucleotide

<400> SEQUENCE: 29
aaaggatccc ccgccatcat ggatgttttc aagaag                               36

<210> SEQ ID NO 30
```

```
<211> LENGTH: 27
<212> TYPE: DNA
<213> ORGANISM: Artificial Sequence
<220> FEATURE:
<223> OTHER INFORMATION: Oligonucleotide

<400> SEQUENCE: 30
aaatctagac tagtctcccc cactctg                                27

<210> SEQ ID NO 31
<211> LENGTH: 9
<212> TYPE: PRT
<213> ORGANISM: Homo sapiens

<400> SEQUENCE: 31

Leu Phe Gln Gly Pro Pro Pro Gln Arg
1               5

<210> SEQ ID NO 32
<211> LENGTH: 9
<212> TYPE: PRT
<213> ORGANISM: Homo sapiens

<400> SEQUENCE: 32

Ala Val Arg Pro Val Pro Asp Pro Ala
1               5

<210> SEQ ID NO 33
<211> LENGTH: 31
<212> TYPE: PRT
<213> ORGANISM: Homo sapiens

<400> SEQUENCE: 33

Leu Ala Arg Arg Gln Ser Pro Gln Val Thr Gln Gln Gly Arg Arg Glu
1               5                   10                  15

Leu Gln Ala Arg Gly Arg Pro Ala Ala Gly Gly Asp Ala Pro Gly
            20                  25                  30

<210> SEQ ID NO 34
<211> LENGTH: 19
<212> TYPE: PRT
<213> ORGANISM: Homo sapiens

<400> SEQUENCE: 34

Gly Glu Glu Gly Gly Ala Ala Arg Pro Asp Ala Val Thr Glu His Ala
1               5                   10                  15

Gly Ala Asp

<210> SEQ ID NO 35
<211> LENGTH: 66
<212> TYPE: PRT
<213> ORGANISM: Homo sapiens

<400> SEQUENCE: 35

Arg Gln Gly Ala Glu Pro Gly Arg Val Ser Val Leu Ala Gly Ala Ala
1               5                   10                  15

Arg Leu Pro Pro Gly Ala Gly Ala Leu Gly Gly Cys Pro Gly Cys
            20                  25                  30

His Leu Gly His Gln Ser Gly Pro Leu Lys Pro Arg Gln His Val His
            35                  40                  45

Tyr Arg Asp Val Leu Pro Gln Ala Ala Gly Gly Pro Pro Gly Pro Gln
        50                  55                  60
```

```
Val Pro
 65

<210> SEQ ID NO 36
<211> LENGTH: 10
<212> TYPE: PRT
<213> ORGANISM: Homo sapiens

<400> SEQUENCE: 36

Asp Ser His Ile Gly Ala Cys Ser Arg Asp
1               5                   10

<210> SEQ ID NO 37
<211> LENGTH: 12
<212> TYPE: PRT
<213> ORGANISM: Homo sapiens

<400> SEQUENCE: 37

Ile Lys Lys Ala Lys Ala Lys Lys Lys Lys Lys Lys
1               5                   10

<210> SEQ ID NO 38
<211> LENGTH: 133
<212> TYPE: PRT
<213> ORGANISM: Homo sapiens

<400> SEQUENCE: 38

Ala Arg Ala His Phe Gln Pro Pro Gly Pro Gln Ala Val Gln Ile His
1               5                   10                  15

Phe Ala Ala Gly Asp Phe Phe Arg Asp Pro Leu Pro Ser Ala Glu Leu
                20                  25                  30

Tyr Val Leu Cys Arg Ile Leu His Asp Trp Pro Asp Asp Lys Val His
            35                  40                  45

Lys Leu Leu Ser Arg Val Ala Glu Ser Cys Lys Pro Gly Ala Gly Leu
    50                  55                  60

Leu Leu Val Glu Thr Leu Leu Asp Glu Glu Lys Arg Val Ala Gln Arg
65                  70                  75                  80

Ala Leu Met Gln Ser Leu Asn Met Leu Val Gln Thr Glu Gly Lys Glu
                85                  90                  95

Arg Ser Leu Gly Glu Tyr Gln Cys Leu Leu Glu Leu His Gly Phe His
            100                 105                 110

Gln Val Gln Val Val His Leu Gly Gly Val Leu Asp Ala Ile Leu Ala
        115                 120                 125

Thr Lys Val Ala Pro
    130

<210> SEQ ID NO 39
<211> LENGTH: 29
<212> TYPE: PRT
<213> ORGANISM: Homo sapiens

<400> SEQUENCE: 39

Ser Pro Gly Ser Met Phe Ile Ile Gly Met Ser Ser Pro Arg Leu Gln
1               5                   10                  15

Val Asp Arg Pro Val Pro Lys Tyr His Arg Thr Val Thr
                20                  25

<210> SEQ ID NO 40
<211> LENGTH: 7
<212> TYPE: PRT
<213> ORGANISM: Homo sapiens
```

-continued

```
<400> SEQUENCE: 40

Glu Arg Val Val Thr Glu
1               5

<210> SEQ ID NO 41
<211> LENGTH: 10
<212> TYPE: PRT
<213> ORGANISM: Homo sapiens

<400> SEQUENCE: 41

Arg Lys Gln Lys Pro Lys Lys Lys Lys
1               5                   10

<210> SEQ ID NO 42
<211> LENGTH: 81
<212> TYPE: PRT
<213> ORGANISM: Homo sapiens

<400> SEQUENCE: 42

His Glu Pro Thr Ser Asn Pro Pro Asp Arg Arg Gln Cys Arg Ser Thr
1               5                   10                  15

Ser Gln Gln Val Thr Phe Ser Gly Thr Pro Ser Pro Ala Leu Ser Cys
            20                  25                  30

Thr Ser Cys Ala Gly Ser Cys Met Thr Gly Gln Thr Thr Lys Ser Thr
        35                  40                  45

Ser Tyr Ser Ala Gly Ser Pro Arg Ala Ala Ser Gln Gly Pro Ala Cys
    50                  55                  60

Cys Trp Trp Arg Arg Ser Trp Met Arg Arg Gly Trp Arg Ser Ala
65                  70                  75                  80

Pro

<210> SEQ ID NO 43
<211> LENGTH: 55
<212> TYPE: PRT
<213> ORGANISM: Homo sapiens

<400> SEQUENCE: 43

Thr Cys Trp Cys Arg Leu Lys Ala Arg Ser Gly Ala Trp Ala Ser Ile
1               5                   10                  15

Ser Ala Cys Trp Ser Cys Thr Ala Ser Thr Arg Cys Arg Trp Cys Thr
            20                  25                  30

Trp Gly Val Ser Trp Met Pro Ser Trp Pro Pro Lys Trp Pro Pro Glu
        35                  40                  45

Ala Gln Ala Ala Cys Ser Leu
    50                  55

<210> SEQ ID NO 44
<211> LENGTH: 24
<212> TYPE: PRT
<213> ORGANISM: Homo sapiens

<400> SEQUENCE: 44

Gly Cys Pro Pro Gly Cys Arg Trp Thr Ala Arg Ser Pro Ser Thr
1               5                   10                  15

Ile Gly Gln Ser His Arg Ser Val
            20

<210> SEQ ID NO 45
<211> LENGTH: 13
```

```
-continued

<212> TYPE: PRT
<213> ORGANISM: Homo sapiens

<400> SEQUENCE: 45

Leu Asn Lys Glu Ser Lys Ser Gln Lys Lys Lys Lys
1               5                   10
```

ANTIBODIES TO BREAST SPECIFIC GENE 1

CROSS REFERENCE TO RELATED APPLICATIONS

This application is a continuation of and claims priority under 35 U.S.C. § 120 to U.S. application Ser. No. 08/673,284, filed Jun. 28, 1996 now abandoned ; which is a non-provisional of and claims benefit under 35 U.S.C. § 119(e) to U.S. Provisional Application No. 60/000,602, filed Jun. 30, 1995; each of which is hereby incorporated by reference in its entirety.

BACKGROUND OF THE INVENTION

This invention relates to newly identified polynucleotides, polypeptides encoded by such polynucleotides, and the use of such polynucleotides and polypeptides for detecting disorders of the breast, particularly the presence of breast cancer and breast cancer metastases. The present invention further relates to inhibiting the production and function of the polypeptides of the present invention. The twenty breast specific genes of the present invention are sometimes hereinafter referred to as "BSG1", "BSG2" etc.

The mammary gland is subject to a variety of disorders that should be readily detectable. Detection may be accomplished by inspection which usually consists of palpation. Unfortunately, so few periodic self-examinations are made that many breast masses are discovered only by accidental palpation. Aspiration of suspected cysts with a fine-gauge needle is another fairly common diagnostic practice. Mammography or xeroradiography (soft-tissue x-ray) of the breast of yet another. A biopsy of a lesion or suspected area is an extreme method of diagnostic test.

There are many types of tumors and cysts which affect the mammary gland. Fibroadenomas is the most common benign breast tumor. As a pathological entity, it ranks third behind cystic disease and carcinoma, respectively. These tumors are seen most frequently in young people and are usually readily recognized because they feel encapsulated. Fibrocystic disease, a benign condition, is the most common disease of the female breast, occurring in about 20% of pre-menopausal women. Lipomas of the breast are also common and they are benign in nature. Carcinoma of the breast is the most common malignant condition among women and carries with it the highest fatality rate of all cancers affecting this sex. At some during her life, one of every 15 women in the USA will develop cancer of the breast. Its reported annual incidence is 70 per 100,000 females in the population in 1947, rising to 72.5 in 1969 for whites, and rising from 47.8 to 60.1 for blacks. The annual mortality rate from 1930 to the present has remained fairly constant, at approximately 23 per 100,000 female population. Breast cancer is rare in men, but when it does occur, it usually not recognized until late, and thus the results of treatment are poor. In women, carcinoma of the breast is rarely seen before age 30 and the incidence rises rapidly after menopause. For this reason, post-menopausal breast masses should be considered cancer until proved otherwise.

BRIEF SUMMARY OF THE INVENTION

In accordance with an aspect of the present invention, there are provided nucleic acid probes comprising nucleic acid molecules of sufficient length to specifically hybridize to the RNA transcribed from the human breast specific genes of the present invention or to DNA corresponding to such RNA.

In accordance with another aspect of the present invention there is provided a method of and products for diagnosing breast cancer formation and breast cancer metastases by detecting the presence of RNA transcribed from the human breast specific genes of the present invention or DNA corresponding to such RNA in a sample derived from a host.

In accordance with yet another aspect of the present invention, there is provided a method of and products for diagnosing breast cancer formation and breast cancer metastases by detecting an altered level of a polypeptide corresponding to the breast specific genes of the present invention in a sample derived from a host, whereby an elevated level of the polypeptide indicates a breast cancer diagnosis.

In accordance with another aspect of the present invention, there are provided isolated polynucleotides encoding human breast specific polypeptides, including mRNAs, DNAs, cDNAs, genomic DNAs, as well as antisense analogs and biologically active and diagnostically or therapeutically useful fragments thereof.

In accordance with still another aspect of the present invention there are provided human breast specific genes which include polynucleotides as set forth in the sequence listing.

In accordance with a further aspect of the present invention, there are provided novel polypeptides encoded by the polynucleotides, as well as biologically active and diagnostically or therapeutically useful fragments, analogs and derivatives thereof.

In accordance with yet a further aspect of the present invention, there is provided a process for producing such polypeptides by recombinant techniques comprising culturing recombinant prokaryotic and/or eukaryotic host cells, containing a polynucleotide of the present invention, under conditions promoting expression of said proteins and subsequent recovery of said proteins.

In accordance with yet a further aspect of the present invention, there are provided antibodies specific to such polypeptides, which may be employed to detect breast cancer cells or breast cancer metastasis.

In accordance with another aspect of the present invention, there are provided processes for using one or more of the polypeptides of the present invention to treat breast cancer and for using the polypeptides to screen for compounds which interact with the polypeptides, for example, compounds which inhibit or activate the polypeptides of the present invention.

In accordance with yet another aspect of the present invention, there is provided a screen for detecting compounds which inhibit activation of one or more of the polynucleotides and/or polypeptides of the present invention which may be used to therapeutically, for example, in the treatment of breast cancer.

In accordance with yet a further aspect of the present invention, there are provided processes for utilizing such polypeptides, or polynucleotides encoding such polypeptides, for in vitro purposes related to scientific research, synthesis of DNA and manufacture of DNA vectors.

These and other aspects of the present invention should be apparent to those skilled in the art from the teachings herein.

BRIEF DESCRIPTION OF THE DRAWINGS

The following drawings are illustrative of embodiments of the invention and are not meant to limit the scope of the invention as encompassed by the claims.

FIG. 1 (SEQ ID NO:1) is a full length cDNA sequence of breast specific gene 1 of the present invention.

FIG. 2 (SEQ ID NO:2) is a partial cDNA sequence and the corresponding deduced amino acid sequence of breast specific gene 2 (HBGBP 46) of the present invention.

FIG. 3 (SEQ ID NO:4) is a partial cDNA sequence and deduced amino acid sequence of breast specific gene 3 of the invention.

FIG. 4 (SEQ ID NO:6) is a partial cDNA sequence and the corresponding deduced amino acid sequence of breast specific gene 4 of the present invention.

FIG. 5 (SEQ ID NO:8) is a partial cDNA sequence of breast specific gene 5 of the present invention.

FIG. 6 (SEQ ID NO:9) is a partial cDNA and deduced amino acid sequence of breast specific gene 6 of the present invention.

FIG. 7 (SEQ ID NO:11) is a partial cDNA sequence of breast specific gene 7 of the present invention.

FIG. 8 (SEQ ID NO:12) is a partial cDNA sequence of breast specific gene 8 of the present invention.

FIG. 9 (SEQ ID NO:13) is a partial cDNA sequence of breast specific gene 9 of the present invention.

FIG. 10 (SEQ ID NO:14) is a partial cDNA sequence of breast specific gene 10 of the present invention.

FIG. 11 (SEQ ID NO:15) is a partial cDNA sequence of breast specific gene 11 of the present invention.

FIG. 12 (SEQ ID NO:16) is a partial cDNA sequence of breast specific gene 12 of the present invention.

FIG. 13 (SEQ ID NO:17) is a partial cDNA sequence of breast specific gene 13 of the present invention.

FIG. 14 (SEQ ID NO:18) is a partial cDNA sequence of breast specific gene 14 of the present invention.

FIG. 15 (SEQ ID NO:19) is a partial cDNA sequence of breast specific gene 15 of the present invention.

FIG. 16 (SEQ ID NO:20) is a partial cDNA sequence of breast specific gene 16 of the present invention.

FIG. 17 (SEQ ID NO:21) is a partial cDNA sequence of breast specific gene 17 of the present invention.

FIG. 18 (SEQ ID NO:22) is a partial cDNA sequence of breast specific gene 18 of the present invention.

FIG. 19 (SEQ ID NO:23) is a partial cDNA sequence of breast specific gene 19 of the present invention.

FIG. 20 (SEQ ID NO:24) is a partial cDNA sequence of breast specific gene 20 of the present invention.

DETAILED DESCRIPTION OF THE INVENTION

The term "breast specific gene" means that such gene is primarily expressed in tissues derived from the breast, and such genes may be expressed in cells derived from tissues other than from the breast. However, the expression of such genes is significantly higher in tissues derived from the breast than from non-breast tissues.

In accordance with one aspect of the present invention there is provided a polynucleotide which encodes a mature polypeptide encoded by the polynucleotide having the sequence of FIG. 1 (SEQ ID NO:1) and fragments, analogues and derivatives thereof.

In accordance with a further aspect of the present invention there is provided a polynucleotide which encodes the same mature polypeptide as a human gene having a coding portion which contains a polynucleotide which is at least 90% identical (preferably at least 95% identical and most preferably at least 97% or 100% identical) to one of the polynucleotides of FIGS. 2–20 (SEQ ID NO:2, 4, 6, 8, 9, 11–24), as well as fragments thereof.

In accordance with still another aspect of the present invention there is provided a polynucleotide which encodes for the same mature polypeptide as a human gene whose coding portion includes a polynucleotide which is at least 90% identical to (preferably at least 95% identical to and most preferably at least 97% or 100% identical) to one of the polynucleotides included in ATCC 97175 of Jun. 2, 1995.

In accordance with yet another aspect of the present invention, there is provided a polynucleotide probe which hybridizes to mRNA (or the corresponding cDNA) which is transcribed from the coding portion of a human gene which coding portion includes a DNA sequence which is at least 90% identical to (preferably at least 95% identical to) and most preferably at least 97% or 100% identical) to one of the polynucleotide sequences of FIGS. 1–20 (SEQ ID NO:2, 4, 6, 8, 9, 11–24).

The present invention further relates to a mature polypeptide encoded by a coding portion of a human gene which coding portion includes a DNA sequence which is at least 90% identical to (preferably at least 95% identical to and more preferably 97% or 100% identical to) one of the polynucleotides of FIG. 2–20 (SEQ ID NO:2, 4, 6, 8, 9, 11–24), and analogues, derivatives and fragments thereof.

The present invention also relates to one of the mature polypeptides encoded by the polynucleotide of FIG. 1 (SEQ ID NO:1) and fragments, analogues and derivatives thereof.

The present invention further relates to the same mature polypeptide encoded by a human gene whose coding portion includes DNA which is at least 90% identical to (preferably at least 95% identical to and more preferably at least 97% or 100% identical to) one of the polynucleotides included in ATCC Deposit No. 97175 deposited Jun. 2, 1995.

In accordance with an aspect of the present invention, there are provided isolated nucleic acids (polynucleotides) which encode for the mature polypeptides encoded by the polynucleotide of FIG. 1 (SEQ ID NO:1) or fragments, analogues or derivatives thereof.

The polynucleotides of the present invention may be in the form of RNA or in the form of DNA, which DNA includes cDNA, genomic DNA, and synthetic DNA. The DNA may be double-stranded or single-stranded, and if single stranded may be the coding strand or non-coding (anti-sense) strand. The coding sequence which encodes the mature polypeptide may include DNA identical to FIGS. 1–20 (SEQ ID NO:1–2, 4, 6, 8–9, 10–24) or that of the deposited clone or may be a different coding sequence which coding sequence, as a result of the redundancy or degeneracy of the genetic code, encodes the same mature polypeptide as the coding sequence of a gene which coding sequence includes the DNA of FIGS. 1–20 (SEQ ID NO:1–2, 4, 6, 8–9, 10–24) or the deposited cDNA.

The polynucleotide which encodes a mature polypeptide of the present invention may include, but is not limited to: only the coding sequence for the mature polypeptide; the coding sequence for the mature polypeptide and additional coding sequence such as a leader or secretory sequence or a proprotein sequence; the coding sequence for the mature polypeptide (and optionally additional coding sequence) and non-coding sequence, such as introns or non-coding sequence 5' and/or 3' of the coding sequence for the mature polypeptide.

Thus, the term "polynucleotide encoding a polypeptide" encompasses a polynucleotide which includes only coding sequence for the polypeptide as well as a polynucleotide which includes additional coding and/or non-coding sequence.

The present invention further relates to variants of the hereinabove described polynucleotides which encode fragments, analogs and derivatives of a mature polypeptide of the present invention. The variant of the polynucleotide may be a naturally occurring allelic variant of the polynucleotide or a non-naturally occurring variant of the polynucleotide.

Thus, the present invention includes polynucleotides encoding the same mature polypeptide as hereinabove described as well as variants of such polynucleotides which variants encode a fragment, derivative or analog of a polypeptide of the invention. Such nucleotide variants include deletion variants, substitution variants and addition or insertion variants.

The polynucleotides of the invention may have a coding sequence which is a naturally occurring allelic variant of the human gene whose coding sequence includes DNA as shown in FIGS. 1–20 (SEQ ID NO:1–2, 4, 6, 8–9, 10–24) or of the deposited clone. As known in the art, an allelic variant is an alternate form of a polynucleotide sequence which may have a substitution, deletion or addition of one or more nucleotides, which does not substantially alter the function of the encoded polypeptide.

The present invention also includes polynucleotides, wherein the coding sequence for the mature polypeptide may be fused in the same reading frame to a polynucleotide sequence which aids in expression and secretion of a polypeptide from a host cell, for example, a leader sequence which functions as a secretory sequence for controlling transport of a polypeptide from the cell. The polypeptide having a leader sequence is a preprotein and may have the leader sequence cleaved by the host cell to form the mature form of the polypeptide. The polynucleotides may also encode a proprotein which is the mature protein plus additional 5' amino acid residues. A mature protein having a prosequence is a proprotein and is an inactive form of the protein. Once the prosequence is cleaved an active mature protein remains.

Thus, for example, the polynucleotide of the present invention may encode a mature protein, or a protein having a prosequence or a protein having both a presequence and a presequence (leader sequence).

The polynucleotides of the present invention may also have the coding sequence fused in frame to a marker sequence which allows for purification of the polypeptide of the present invention. The marker sequence may be a hexa-histidine tag supplied by a pQE-9 vector to provide for purification of the mature polypeptide fused to the marker in the case of a bacterial host, or, for example, the marker sequence may be a hemagglutinin (HA) tag when a mammalian host, e.g. COS-7 cells, is used. The HA tag corresponds to an epitope derived from the influenza hemagglutinin protein (Wilson, I., et al., Cell, 37:767 (1984)).

The present invention further relates to polynucleotides which hybridize to the hereinabove-described polynucleotides if there is at least 70%, preferably at least 90%, and more preferably at least 95% identity between the sequences. The present invention particularly relates to polynucleotides which hybridize under stringent conditions to the hereinabove-described polynucleotides. As herein used, the term "stringent conditions" means hybridization will occur only if there is at least 95% and preferably at least 97% identity between the sequences. The polynucleotides which hybridize to the hereinabove described polynucleotides in a preferred embodiment encode polypeptides which retain substantially the same biological function or activity as the mature polypeptide of the present invention encoded by a coding sequence which includes the DNA of FIGS. 1–20 (SEQ ID NO:1–2, 4, 6, 8–9, 10–24) or the deposited cDNA(s).

Alternatively, the polynucleotide may have at least 10 or 20 bases, preferably at least 30 bases, and more preferably at least 50 bases which hybridize to a polynucleotide of the present invention and which has an identity thereto, as hereinabove described, and which may or may not retain activity. For example, such polynucleotides may be employed as probes for polynucleotides, for example, for recovery of the polynucleotide or as a diagnostic probe or as a PCR primer.

Thus, the present invention is directed to polynucleotides having at least a 70% identity, preferably at least 90% and more preferably at least 95% identity to a polynucleotide which encodes the mature polypeptide encoded by a human gene which includes the DNA of one of FIGS. 1–20 (SEQ ID NO:1–2, 4, 6, 8–9, 10–24) as well as fragments thereof, which fragments have at least 30 bases and preferably at least 50 bases and to polypeptides encoded by such polynucleotides.

The partial sequences are specific tags for messenger RNA molecules. The complete sequence of that messenger RNA, in the form of cDNA, is determined using the partial sequence as a probe to identify a cDNA clone corresponding to a full-length transcript. The partial cDNA clone can also be used as a probe to identify a genomic clone or clones that contain the complete gene including regulatory and promoter regions, exons, and introns.

The partial sequences of FIGS. 2–20 (SEQ ID NO:2, 4, 6, 8, 9, 11–24) may be used to identify the corresponding full length gene from which they were derived. The partial sequences can be nick-translated or end-labelled with $^{32}p$ using polynucleotide kinase using labelling methods known to those with skill in the art (Basic Methods in Molecular Biology, L. G. Davis, M. D. Dibner, and J. F. Battey, ed., Elsevier Press, NY, 1986). A lambda library prepared from human breast tissue can be directly screened with the labelled sequences of interest or the library can be converted en masse to pBluescript (Stratagene Cloning Systems, La Jolla, Calif. 92037) to facilitate bacterial breasty screening. Regarding pBluescript, see Sambrook et al., Molecular Cloning-A Laboratory Manual, Cold Spring Harbor Laboratory Press (1989), pg. 1.20 Both methods are well known in the art. Briefly, filters with bacterial colonies containing the library in pBluescript or bacterial lawns containing lambda plaques are denatured and the DNA is fixed to the filters. The filters are hybridized with the labelled probe using hybridization conditions described by Davis et al., supra. The partial sequences, cloned into lambda or pBluescript, can be used as positive controls to assess background binding and to adjust the hybridization and washing stringencies necessary for accurate clone identification. The resulting autoradiograms are compared to duplicate plates of colonies or plaques; each exposed spot corresponds to a positive breasty or plaque. The colonies or plaques are selected, expanded and the DNA is isolated from the colonies for further analysis and sequencing.

Positive cDNA clones are analyzed to determine the amount of additional sequence they contain using PCR with one primer from the partial sequence and the other primer from the vector. Clones with a larger vector-insert PCR product than the original partial sequence are analyzed by restriction digestion and DNA sequencing to determine whether they contain an insert of the same size or similar as the mRNA size determined from Northern blot Analysis.

Once one or more overlapping cDNA clones are identified, the complete sequence of the clones can be determined. The preferred method is to use exonuclease III digestion (McCombie, W. R, Kirkness, E., Fleming, J. T., Kerlavage, A. R., Iovannisci, D. M., and Martin-Gallardo, R., Methods, 3:33–40, 1991). A series of deletion clones are generated, each of which is sequenced. The resulting overlapping sequences are assembled into a single contiguous sequence of high redundancy (usually three to five overlapping sequences at each nucleotide position), resulting in a highly accurate final sequence.

The DNA sequences (as well as the corresponding RNA sequences) also include sequences which are or contain a DNA sequence identical to one contained in and isolatable from ATCC Deposit No. 97175, deposited Jun. 2, 1995, and fragments or portions of the isolated DNA sequences (and corresponding RNA sequences), as well as DNA (RNA) sequences encoding the same polypeptide. In particular. DNA (RNA) secuences encoding BSG1 (SEQ ID NO:32) and the amino acid sequence encoded thereby (SEQ ID NO:33) are contained in and isolatable from ATCC Deposit No. 97175 using routine techniques known in the art. A cDNA clone, HBGBP46, encoding BSG2 was deposited as ATCC Deposit No. PTA-1545 on Mar. 22, 2000, at the American Type Culture Collection, Patent Depository, 10801 University Boulevard, Manassas, Va. 20110-2209.

The deposit(s) referred to herein will be maintained under the terms of the Budapest Treaty on the International Recognition of the Deposit of Micro-organisms for purposes of Patent Procedure. These deposits are provided merely as convenience to those of skill in the art and are not an admission that a deposit is required under 35 U.S.C. §112. The sequence of the polynucleotides contained in the deposited materials, as well as the amino acid sequence of the polypeptides encoded thereby, are incorporated herein by reference and are controlling in the event of any conflict with any description of sequences herein. A license may be required to make, use or sell the deposited materials, and no such license is hereby granted.

The present invention further relates to polynucleotides which have at least 10 bases, preferably at least 20 bases, and may have 30 or more bases, which polynucleotides are hybridizable to and have at least a 70% identity to RNA (and DNA which corresponds to such RNA) transcribed from a human gene whose coding portion includes DNA as hereinabove described.

Thus, the polynucleotide sequences which hybridize as described above may be used to hybridize to and detect the expression of the human genes to which they correspond for use in diagnostic assays as hereinafter described.

In accordance with still another aspect of the present invention there are provided diagnostic assays for detecting micrometastases of breast cancer in a host. While applicant does not wish to limit the reasoning of the present invention to any specific scientific theory, it is believed that the presence of active transcription of a breast specific gene of the present invention in cells of the host, other than those derived from the breast, is indicative of breast cancer metastases. This is true because, while the breast specific genes are found in all cells of the body, their transcription to mRNA, cDNA and expression products is primarily limited to the breast in non-diseased individuals. However, if breast cancer is present, breast cancer cells migrate from the cancer to other cells, such that these other cells are now actively transcribing and expressing a breast specific gene at a greater level than is normally found in non-diseased individuals, i.e., transcription is higher than found in non-breast tissues in healthy individuals. It is the detection of this enhanced transcription or enhanced protein expression in cells, other than those derived from the breast, which is indicative of metastases of breast cancer.

In one example of such a diagnostic assay, an RNA sequence in a sample derived from a tissue other than the breast is detected by hybridization to a probe. The sample contains a nucleic acid or a mixture of nucleic acids, at least one of which is suspected of containing a human breast specific gene or fragment thereof of the present invention which is transcribed and expressed in such tissue. Thus, for example, in a form of an assay for determining the presence of a specific RNA in cells, initially RNA is isolated from the cells.

A sample may be obtained from cells derived from tissue other than from the breast including but not limited to blood, urine, saliva, tissue biopsy and autopsy material. The use of such methods for detecting enhanced transcription to mRNA from a human breast specific gene of the present invention or fragment thereof in a sample obtained from cells derived from other than the breast is well within the scope of those skilled in the art from the teachings herein.

The isolation of mRNA comprises isolating total cellular RNA by disrupting a cell and performing differential centrifugation. Once the total RNA is isolated, mRNA is isolated by making use of the adenine nucleotide residues known to those skilled in the art as a poly(A) tail found on virtually every eukaryotic mRNA molecule at the 3' end thereof. Oligonucleotides composed of only deoxythymidine [olig(dT)] are linked to cellulose and the oligo(dT)-cellulose packed into small columns. When a preparation of total cellular RNA is passed through such a column, the mRNA molecules bind to the oligo(dT) by the poly(A)tails while the rest of the RNA flows through the column. The bound mRNAs are then eluted from the column and collected.

One example of detecting isolated mRNA transcribed from a breast specific gene of the present invention comprises screening the collected mRNAs with the gene specific oligonucleotide probes, as hereinabove described.

It is also appreciated that such probes can be and are preferably labeled with an analytically detectable reagent to facilitate identification of the probe. Useful reagents include but are not limited to radioactivity, fluorescent dyes or enzymes capable of catalyzing the formation of a detectable product.

An example of detecting a polynucleotide complementary to the mRNA sequence (cDNA) utilizes the polymerase chain reaction (PCR) in conjunction with reverse transcriptase. PCR is a very powerful method for the specific amplification of DNA or RNA stretches (Saiki et al., *Nature*, 234:163–166 (1986)). One application of this technology is in nucleic acid probe technology to bring up nucleic acid sequences present in low copy numbers to a detectable level. Numerous diagnostic and scientific applications of this method have been described by H. A. Erlich (ed.) in PCR Technology-Principles and Applications for DNA Amplification, Stockton Press, USA, 1989, and by M. A. Inis (ed.) in PCR Protocols, Academic Press, San Diego, USA, 1990.

RT-PCR is a combination of PCR with the reverse transcriptase enzyme. Reverse transcriptase is an enzyme which produces cDNA molecules from corresponding mRNA molecules. This is important since PCR amplifies nucleic acid molecules, particularly DNA, and this DNA may be produced from the mRNA isolated from a sample derived from the host.

A specific example of an RT-PCR diagnostic assay involves removing a sample from a tissue of a host. Such a sample will be from a tissue, other than the breast, for example, blood. Therefore, an example of such a diagnostic assay comprises whole blood gradient isolation of nucleated cells, total RNA extraction, RT-PCR of total RNA and agarose gel electrophoresis of PCR products. The PCR products comprise cDNA complementary to RNA transcribed from one or more breast specific genes of the present invention or fragments thereof. More particularly, a blood sample is obtained and the whole blood is combined with an equal volume of phosphate buffered saline, centrifuged and the lymphocyte and granulocyte layer is carefully aspirated and rediluted in phosphate buffered saline and centrifuged again. The supernate is discarded and the pellet containing nucleated cells is used for RNA extraction using the RNazole B method as described by the manufacturer (Tel-Test Inc., Friendswood, Tex.).

Oligonucleotide primers and probes are prepared with high specificity to the DNA sequences of the present invention. The probes are at least 10 base pairs in length, preferably at least 30 base pairs in length and most preferably at least 50 base pairs in length or more. The reverse transcriptase reaction and PCR amplification are performed sequentially without interruption. Taq polymerase is used during PCR and the PCR products are concentrated and the entire sample is run on a Tris-borate-EDTA agarose gel containing ethidium bromide.

In accordance with another aspect of the present invention, there is provided a method of diagnosing a disorder of the breast, for example breast cancer, by determining altered levels of the breast specific polypeptides of the present invention in a biological sample, derived from tissue other than from the breast. Elevated levels of the breast specific polypeptides of the present invention, indicates active transcription and expression of the corresponding breast specific gene product. Assays used to detect levels of a breast specific gene polypeptide in a sample derived from a host are well-known to those skilled in the art and include radioimmunoassays, competitive-binding assays, Western blot analysis, ELISA assays and "sandwich" assays. A biological sample may include, but is not limited to, tissue extracts, cell samples or biological fluids, however, in accordance with the present invention, a biological sample specifically does not include tissue or cells of the breast.

An ELISA assay (Coligan, et al., *Current Protocols in Immunology*, 1(2), Chapter 6, 1991) initially comprises preparing an antibody specific to a breast specific polypeptide of the present invention, preferably a monoclonal antibody. In addition, a reporter antibody is prepared against the monoclonal antibody. To the reporter antibody is attached a detectable reagent such as radioactivity, fluorescence or, in this example, a horseradish peroxidase enzyme. A sample is removed from a host and incubated on a solid support, e.g., a polystyrene dish, that binds the proteins in the sample. Any free protein binding sites on the dish are then covered by incubating with a non-specific protein, such as BSA. Next, the monoclonal antibody is incubated in the dish during which time the monoclonal antibodies attach to the breast specific polypeptide attached to the polystyrene dish. All unbound monoclonal antibody is washed out with buffer. The reporter antibody linked to horseradish peroxidase is now placed in the dish resulting in binding of the reporter antibody to any monoclonal antibody bound to the breast specific gene polypeptide. Unattached reporter antibody is then washed out. Peroxidase substrates are then added to the dish and the amount of color developed in a given time period is a measurement of the amount of the breast specific polypeptide present in a given volume of patient sample when compared against a standard curve.

A competition assay may be employed where antibodies specific to a breast specific polypeptide are attached to a solid support. The breast specific polypeptide is then labeled and the labeled polypeptide a sample derived from the host are passed over the solid support and the amount of label detected, for example, by liquid scintillation chromatography, can be correlated to a quantity of the breast specific polypeptide in the sample.

A "sandwich" assay is similar to an ELISA assay. In a "sandwich" assay, breast specific polypeptides are passed over a solid support and bind to antibody attached to the solid support. A second antibody is then bound to the breast specific polypeptide. A third antibody which is labeled and is specific to the second antibody, is then passed over the solid support and binds to the second antibody and an amount can then be quantified.

In alternative methods, labeled antibodies to a breast specific polypeptide are used. In a one-step assay, the target molecule, if it is present, is immobilized and incubated with a labeled antibody. The labeled antibody binds to the immobilized target molecule. After washing to remove the unbound molecules, the sample is assayed for the presence of the label. In a two-step assay, immobilized target molecule is incubated with an unlabeled antibody. The target molecule-labeled antibody complex, if present, is then bound to a second, labeled antibody that is specific for the unlabeled antibody. The sample is washed and assayed for the presence of the label.

Such antibodies specific to breast specific gene proteins, for example, anti-idiotypic antibodies, can be used to detect breast cancer cells by being labeled and described above and binding tightly to the breast cancer cells, and, therefore, detect their presence.

The antibodies may also be used to target breast cancer cells, for example, in a method of homing interaction agents which, when contacting breast cancer cells, destroy them. This is true since the antibodies are specific for breast specific genes which are primarily expressed in breast cancer, and a linking of the interaction agent to the antibody would cause the interaction agent to be carried directly to the breast.

Antibodies of this type may also be used to do in vivo imaging, for example, by labeling the antibodies to facilitate scanning of the breast. One method for imaging comprises contacting any cancer cells of the breast to be imaged with an anti-breast specific gene protein antibody labeled with a detectable marker. The method is performed under conditions such that the labeled antibody binds to the breast specific gene proteins. In a specific example, the antibodies interact with the breast, for example, breast cancer cells, and fluoresce upon such contact such that imaging and visibility of the breast is enhanced to allow a determination of the diseased or non-diseased state of the breast.

The choice of marker used to label the antibodies will vary depending upon the application. However, the choice of marker is readily determinable to one skilled in the art. These labeled antibodies may be used in immunoassays as well as in histological applications to detect the presence of the proteins. The labeled antibodies may be polyclonal or monoclonal.

The presence of active transcription, which is greater than that normally found, of the breast specific genes in cells other than from the breast, by the presence of an altered level of mRNA, cDNA or expression products is an important indication of the presence of a breast cancer which has metastasized, since breast cancer cells are migrating from the breast into the general circulation. Accordingly, this phenomenon may have important clinical implications since the method of treating a localized, as opposed to a metastasized, tumor is entirely different.

Of the 20 breast specific genes disclosed, only breast specific gene 1 is a full-length gene. Breast specific gene 1 is 79% identical and 83% similar to human Alzheimer disease amyloid gene. Breast specific gene 2 is 30% identical and 48% similar to human hydroxyindole-o-methyltransferase gene. Breast specific gene 3 is 58% identical and 62% similar to human 06-methylguanine-DNA methyltransferase gene. Breast specific gene 4 is 34% identical and 65% similar to the mouse p120 gene. Breast specific gene 5 is 78% identical and 89% similar to human p70 ribosomal S6 kinase alpha-II gene. Breast specific gene 6 is 77% identical and 79% similar to the human transcription factor NFATp gene.

As stated previously, the breast specific genes of the present invention are putative molecular markers in the diagnosis of breast cancer formation, and breast cancer metastases. As shown in the following Table 1, the presence of the breast specific genes when tested in normal breast, breast cancer, embryo and other cancer libraries, the breast specific genes of the present invention were found to be most prevalent in the breast cancer library, indicating that the genes of the present invention may be employed for detecting breast cancer, as discussed previously. The table also indicates a putative identification, based on homology, of BSG1 through BSG6 to known genes.

TABLE 1

| Genes | Homolog Gene Name (Class) | Norm Br | Br Ca | Embryo | Other Cancers | Others |
|---|---|---|---|---|---|---|
| BSG1 | AD Amyloid (3) | 1 | 6 | | | 1 |
| BSG2 | Hydroxyindole-o-methytransferase (2) | | 3 | 1 | 1 | |
| BSG3 | O-6-methylguanine-DNA methyltransferase (1) | | 3 | 1 | 1 | |
| BSG4 | P120 (3) | | 3 | | 1 | |
| BSG5 | p70 ribosomal S6 Kinase alpha-II (2) | | 3 | | 1 | |
| BSG6 | Transcription factor NFATp(3) | 2 | | | | |
| BSG7 | | | 2 | 1 | | |
| BSG8 | | | 4 | | 3 | 1 |
| BSG8 | | | 2 | | | |
| BSG9 | | | 3 | | | |
| BSG10 | | | 3 | | | |
| BSG11 | | | 3 | | | |
| BSG12 | | 3 | 3 | | | |
| BSG13 | | | 3 | | | |
| BSG14 | | | 2 | | | |
| BSG15 | | 3 | | | | |
| BSG16 | | 1 | 1 | 1 | | |
| BSG17 | | | 2 | | 1 | |
| BSG18 | | 2 | | | | |
| BSG19 | | 1 | 1 | | | |
| BSG20 | | 2 | | | | |

The assays described above may also be used to test whether bone marrow preserved before chemotherapy is contaminated with micrometastases of a breast cancer cell. In the assay, blood cells from the bone marrow are isolated and treated as described above, this method allows one to determine whether preserved bone marrow is still suitable for transplantation after chemotherapy.

The present invention further relates to mature polypeptides, for example the BSG1 polypeptide, as well as fragments, analogs and derivatives of such polypeptide.

The terms "fragment," "derivative" and "analog" when referring to the polypeptides encoded by the genes of the invention means a polypeptide which retains essentially the same biological function or activity as such polypeptide. Thus, an analog includes a proprotein which can be activated by cleavage of the proprotein portion to produce an active mature polypeptide.

The polypeptides of the present invention may be recombinant polypeptides, natural polypeptides or synthetic polypeptides, preferably recombinant polypeptides.

The fragment, derivative or analog of the polypeptides encoded by the genes of the invention may be (i) one in which one or more of the amino acid residues are substituted with a conserved or non-conserved amino acid residue (preferably a conserved amino acid residue) and such substituted amino acid residue may or may not be one encoded by the genetic code, or (ii) one in which one or more of the amino acid residues includes a substituent group, or (iii) one in which the polypeptide is fused with another compound, such as a compound to increase the half-life of the polypeptide (for example, polyethylene glycol), or (iv) one in which the additional amino acids are fused to the polypeptide, such as a leader or secretory sequence or a sequence which is employed for purification of the mature polypeptide or a proprotein sequence. Such fragments, derivatives and analogs are deemed to be within the scope of those skilled in the art from the teachings herein.

The polypeptides and polynucleotides of the present invention are preferably provided in an isolated form, and preferably are purified to homogeneity.

The term "isolated" means that the material is removed from its original environment (e.g., the natural environment if it is naturally occurring). For example, a naturally-occurring polynucleotide or polypeptide present in a living animal is not isolated, but the same polynucleotide or polypeptide, separated from some or all of the coexisting materials in the natural system, is isolated. Such polynucleotides may be part of a vector.

The polypeptides of the present invention include the polypeptides encoded by the polynucleotide of FIG. 1 (SEQ ID NO:1) (in particular the mature polypeptides) as well as polypeptides which have at least 70% similarity (preferably at least a 70% identity) to the polypeptides encoded by the polynucleotide of FIG. 1 (SEQ ID NO:1) and preferably at least a 90% similarity (preferably at least a 90% identity) to the polypeptides of FIGS. 8 and 9 (SEQ ID NO:12 and 13) and more preferably at least a 95% similarity (still more preferably at least 95% identity) to the polypeptides encoded by the polynucleotide of (SEQ ID NO:1) and also include portions of such polypeptides with such portion of the polypeptide generally containing at least 30 amino acids and more preferably at least 50 amino acids.

As known in the art "similarity" between two polypeptides is determined by comparing the amino acid sequence and its conserved amino acid substitutes of one polypeptide to the sequence of a second polypeptide.

Fragments or portions of the polypeptides of the present invention may be employed for producing the corresponding full-length polypeptide by peptide synthesis; therefore, the fragments may be employed as intermediates for producing the full-length polypeptides. Fragments or portions of the polynucleotides of the present invention may be used to synthesize full-length polynucleotides of the present invention.

The present invention also relates to vectors which include polynucleotides of the present invention, host cells which are genetically engineered with vectors of the invention and the production of polypeptides of the invention by recombinant techniques.

Host cells are genetically engineered (transduced or transformed or transfected) with the vectors of this invention which may be, for example, a cloning vector or an expression vector. The vector may be, for example, in the form of a plasmid, a viral particle, a phage, etc. The engineered host cells can be cultured in conventional nutrient media modified as appropriate for activating promoters, selecting transformants or amplifying the breast specific genes. The culture conditions, such as temperature, pH and the like, are those previously used with the host cell selected for expression, and will be apparent to those of ordinarily skill in the art.

The polynucleotides of the present invention may be employed for producing polypeptides by recombinant techniques. Thus, for example, the polynucleotide may be included in any one of a variety of expression vectors for expressing a polypeptide. Such vectors include chromosomal, nonchromosomal and synthetic DNA sequences, e.g., derivatives of SV40; bacterial plasmids; phage DNA; baculovirus; yeast plasmids; vectors derived from combinations of plasmids and phage DNA, viral DNA such as vaccinia, adenovirus, fowl pox virus, and pseudorabies. However, any other vector may be used as long as it is replicable and viable in the host.

The appropriate DNA sequence may be inserted into the vector by a variety of procedures. In general, the DNA sequence is inserted into an appropriate restriction endonuclease site(s) by procedures known in the art. Such procedures and others are deemed to be within the scope of those skilled in the art.

The DNA sequence in the expression vector is operatively linked to an appropriate expression control sequence(s) (promoter) to direct mRNA synthesis. As representative examples of such promoters, there may be mentioned: LTR or SV40 promoter, the *E. coli*. lac or trp, the phage lambda $P_L$ promoter and other promoters known to control expression of genes in prokaryotic or eukaryotic cells or their viruses. The expression vector also contains a ribosome binding site for translation initiation and a transcription terminator. The vector may also include appropriate sequences for amplifying expression.

In addition, the expression vectors preferably contain one or more selectable marker genes to provide a phenotypic trait for selection of transformed host cells such as dihydrofolate reductase or neomycin resistance for eukaryotic cell culture, or such as tetracycline or ampicillin resistance in *E. coli*.

The vector containing the appropriate DNA sequence as hereinabove described, as well as an appropriate promoter or control sequence, may be employed to transform an appropriate host to permit the host to express the protein.

As representative examples of appropriate hosts, there may be mentioned: bacterial cells, such as *E. coli, Streptomyces, Salmonella typhimurium*; fungal cells, such as yeast; insect cells such as *Drosophila* S2 and *Spodoptera* Sf9; animal cells such as CHO, COS or Bowes melanoma; adenoviruses; plant cells, etc. The selection of an appropriate host is deemed to be within the scope of those skilled in the art from the teachings herein.

More particularly, the present invention also includes recombinant constructs comprising one or more of the sequences as broadly described above. The constructs comprise a vector, such as a plasmid or viral vector, into which a sequence of the invention has been inserted, in a forward or reverse orientation. In a preferred aspect of this embodiment, the construct further comprises regulatory sequences, including, for example, a promoter, operably linked to the sequence. Large numbers of suitable vectors and promoters are known to those of skill in the art, and are commercially available. The following vectors are provided by way of example. Bacterial: pQE70, pQE60, pQE-9 (Qiagen), pBS, pD10, phagescript, psiX174, pbluescript SK, pBSKS, pNH8A, pNH16a, pNH18A, pNH46A (Stratagene): ptrc99a, pKK223-3, pKK233-3, pDR540, pRIT5 (Pharmacia). Eukaryotic: pWLNEO, pSV2CAT, pOG44, pXT1, pSG (Stratagene) pSVK3, pBPV, pMSG, pSVL (Pharmacia). However, any other plasmid or vector may be used as long as they are replicable and viable in the host.

Promoter regions can be selected from any desired gene using CAT (chloramphenicol transferase) vectors or other vectors with selectable markers. Two appropriate vectors are pKK232-8 and pCM7. Particular named bacterial promoters include lacI, lacZ, T3, T7, gpt, lambda $P_R$, $P_L$ and trp. Eukaryotic promoters include CMV immediate early, HSV thyridine kinase, early and late SV40, LTRs from retrovirus, and mouse metallothionein-I. Selection of the appropriate vector and promoter is well within the level of ordinary skill in the art.

In a further embodiment, the present invention relates to host cells containing the above-described constructs. The host cell can be a higher eukaryotic cell, such as a mammalian cell, or a lower eukaryotic cell, such as a yeast cell, or the host cell can be a prokaryotic cell, such as a bacterial cell. Introduction of the construct into the host cell can be effected by calcium phosphate transfection, DEAE-Dextran mediated transfection, or electroporation (Davis, L., Dibner, M., Battey, I., Basic Methods in Molecular Biology, (1986)).

The constructs in host cells can be used in a conventional manner to produce the gene product encoded by the recombinant sequence. Alternatively, the polypeptides of the invention can be synthetically produced by conventional peptide synthesizers.

Proteins can be expressed in mammalian cells, yeast, bacteria, or other cells under the control of appropriate promoters. Cell-free translation systems can also be employed to produce such proteins using RNAs derived from the DNA constructs of the present invention. Appropriate cloning and expression vectors for use with prokaryotic and eukaryotic hosts are described by Sambrook, et al., Molecular Cloning: A Laboratory Manual, Second Edition, Cold Spring Harbor, N.Y., (1989), the disclosure of which is hereby incorporated by reference.

Transcription of the DNA encoding the polypeptides of the present invention by higher eukaryotes is increased by inserting an enhancer sequence into the vector. Enhancers are cis-acting elements of DNA, usually about from 10 to 300 bp that act on a promoter to increase its transcription. Examples including the SV40 enhancer on the late side of the replication origin bp 100 to 270, a cytomegalovirus early promoter enhancer, the polyoma enhancer on the late side of the replication origin, and adenovirus enhancers.

Generally, recombinant expression vectors will include origins of replication and selectable markers permitting transformation of the host cell, e.g., the ampicillin resistance gene of *E. coli* and *S. cerevisiae* TRP1 gene, and a promoter derived from a highly-expressed gene to direct transcription of a downstream structural sequence. Such promoters can be derived from operons encoding glycolytic enzymes such as 3-phosphoglycerate kinase (PGK), -factor, acid phosphatase, or heat shock proteins, among others. The heterologous structural sequence is assembled in appropriate phase with translation initiation and termination sequences. Optionally, the heterologous sequence can encode a fusion protein including an N-terminal identification peptide imparting desired characteristics, e.g., stabilization or simplified purification of expressed recombinant product.

Useful expression vectors for bacterial use are constructed by inserting a structural DNA sequence encoding a desired protein together with suitable translation initiation and termination signals in operable reading frame with a functional promoter. The vector will comprise one or more phenotypic selectable markers and an origin of replication to ensure maintenance of the vector and to, if desirable, provide amplification within the host. Suitable prokaryotic hosts for transformation include *E. coli, Bacillus subtilis, Salmonella typhimurium* and various species within the genera *Pseudomonas, Streptomyces*, and *Staphylococcus*, although others may also be employed as a matter of choice.

As a representative but nonlimiting example, useful expression vectors for bacterial use can comprise a selectable marker and bacterial origin of replication derived from commercially available plasmids comprising genetic elements of the well known cloning vector pBR322 (ATCC 37017). Such commercial vectors include, for example, pKK223-3 (Pharmacia Fine Chemicals, Uppsala, Sweden) and GEMI (Promega Biotec, Madison, Wis., USA). These pBR322 "backbone" sections are combined with an appropriate promoter and the structural sequence to be expressed.

Following transformation of a suitable host strain and growth of the host strain to an appropriate cell density, the selected promoter is induced by appropriate means (e.g., temperature shift or chemical induction) and cells are cultured for an additional period.

Cells are typically harvested by centrifugation, disrupted by physical or chemical means, and the resulting crude extract retained for further purification.

Microbial cells employed in expression of proteins can be disrupted by any convenient method, including freeze-thaw cycling, sonication, mechanical disruption, or use of cell lysing agents, such methods are well know to those skilled in the art.

Various mammalian cell culture systems can also be employed to express recombinant protein. Examples of mammalian expression systems include the COS-7 lines of monkey kidney fibroblasts, described by Gluzman, Cell, 23:175 (1981), and other cell lines capable of expressing a compatible vector, for example, the C127, 3T3, CHO, HeLa and BHK cell lines. Mammalian expression vectors will comprise an origin of replication, a suitable promoter and enhancer, and also any necessary ribosome binding sites, polyadenylation site, splice donor and acceptor sites, transcriptional termination sequences, and 5' flanking nontranscribed sequences. DNA sequences derived from the SV40 splice, and polyadenylation sites may be used to provide the required nontranscribed genetic elements.

The breast specific gene polypeptides can be recovered and purified from recombinant cell cultures by methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Protein refolding steps can be used, as necessary, in completing configuration of the mature protein. Finally, high performance liquid chromatography (HPLC) can be employed for final purification steps.

The polynucleotides of the present invention may have the coding sequence fused in frame to a marker sequence which allows for purification of the polypeptide of the present invention. An example of a marker sequence is a hexahistidine tag which may be supplied by a vector, preferably a pQE-9 vector, which provides for purification of the polypeptide fused to the marker in the case of a bacterial host, or, for example, the marker sequence may be a hemagglutinin (HA) tag when a mammalian host, e.g. COS-7 cells, is used. The HA tag corresponds to an epitope derived from the influenza hemagglutinin protein (Wilson, I., et al., Cell, 37:767 (1984)).

The polypeptides of the present invention may be a naturally purified product, or a product of chemical synthetic procedures, or produced by recombinant techniques from a prokaryotic or eukaryotic host (for example, by bacterial, yeast, higher plant, insect and mammalian cells in culture). Depending upon the host employed in a recombinant production procedure, the polypeptides of the present invention may be glycosylated or may be non-glycosylated. Polypeptides of the invention may also include an initial methionine amino acid residue.

BSG1, and other breast specific genes, and the protein product thereof may be employed for early detection of breast cancer since they are over-expressed in the breast cancer state.

In accordance with another aspect of the present invention there are provided assays which may be used to screen for therapeutics to inhibit the action of the breast specific genes or breast specific proteins of the present invention. The present invention discloses methods for selecting a therapeutic which forms a complex with breast specific gene proteins with sufficient affinity to prevent their biological action. The methods include various assays, including competitive assays where the proteins are immobilized to a support, and are contacted with a natural substrate and a labeled therapeutic either simultaneously or in either consecutive order, and determining whether the therapeutic effectively competes with the natural substrate in a manner sufficient to prevent binding of the protein to its substrate.

In another embodiment, the substrate is immobilized to a support, and is contacted with both a labeled breast specific polypeptide and a therapeutic (or unlabeled proteins and a labeled therapeutic), and it is determined whether the amount of the breast specific polypeptide bound to the substrate is reduced in comparison to the assay without the therapeutic added. The breast specific polypeptide may be labeled with antibodies.

Potential therapeutic compounds include antibodies and anti-idiotypic antibodies as described above, or in some cases, an oligonucleotide, which binds to the polypeptide.

Another example is an antisense construct prepared using antisense technology, which is directed to a breast specific polynucleotide to prevent transcription. Antisense technology can be used to control gene expression through triple-helix formation or antisense DNA or RNA, both of which methods are based on binding of a polynucleotide to DNA or RNA. For example, the 5' coding portion of the polynucleotide sequence, which encodes for the mature polypeptides of the present invention, is used to design an antisense RNA oligonucleotide of from about 10 to 40 base pairs in length. A DNA oligonucleotide is designed to be complementary to a region of the gene involved in transcription (triple helix—see Lee et al., Nucl. Acids Res., 6:3073 (1979); Cooney et al, Science, 241:456 (1988); and Dervan et al., Science, 251: 1360 (1991)), thereby preventing transcription and the production of a breast specific polynucleotide. The antisense RNA oligonucleotide hybridizes to the mRNA in vivo and blocks translation of the mRNA molecule into the breast specific genes polypeptide (antisense—Okano, J. Neurochem., 56:560 (1991); Oligodeoxynucleotides as Antisense Inhibitors of Gene Expression, CRC Press, Boca Raton, Fla.(1988)). The oligonucleotides described above can also be delivered to cells such that the antisense RNA or DNA may be expressed in vivo to inhibit production of the breast specific polypeptides.

Another example is a small molecule which binds to and occupies the active site of the breast specific polypeptide thereby making the active site inaccessible to substrate such that normal biological activity is prevented. Examples of small molecules include but are not limited to small peptides or peptide-like molecules.

These compounds may be employed to treat breast cancer, since they interact with the function of breast specific polypeptides in a manner sufficient to inhibit natural function which is necessary for the viability of breast cancer cells. This is true since the BSGs and, their protein products are primarily expressed in breast cancer tissues and are, therefore, suspected of being critical to the formation of this state.

The compounds may be employed in a composition with a pharmaceutically acceptable carrier, e.g., as hereinafter described.

The compounds of the present invention may be employed in combination with a suitable pharmaceutical carrier. Such compositions comprise a therapeutically effective amount of the polypeptide, and a pharmaceutically acceptable carrier or excipient. Such a carrier includes but is not limited to saline, buffered saline, dextrose, water, glycerol, ethanol, and combinations thereof. The formulation should suit the mode of administration.

The invention also provides a pharmaceutical pack or kit comprising one or more containers filled with one or more of the ingredients of the pharmaceutical compositions of the invention. Associated with such container(s) can be a notice in the form prescribed by a governmental agency regulating the manufacture, use or sale of pharmaceuticals or biological products, which notice reflects approval by the agency of manufacture, use or sale for human administration. In addition, the pharmaceutical compositions may be employed in conjunction with other therapeutic compounds.

The pharmaceutical compositions may be administered in a convenient manner such as by the oral, topical, intravenous, intraperitoneal, intramuscular, subcutaneous, intranasal, intra-anal or intradermal routes. The pharmaceutical compositions are administered in an amount which is effective for treating and/or prophylaxis of the specific indication. In general, they are administered in an amount of at least about 10 g/kg body weight and in most cases they will be administered in an amount not in excess of about 8 mg/Kg body weight per day. In most cases, the dosage is from about 10 g/kg to about 1 mg/kg body weight daily, taking into account the routes of administration, symptoms, etc.

The breast specific genes and compounds which are polypeptides may also be employed in accordance with the present invention by expression of such polypeptides in vivo, which is often referred to as "gene therapy."

Thus, for example, cells from a patient may be engineered with a polynucleotide (DNA or RNA) encoding a polypeptide ex vivo, with the engineered cells then being provided to a patient to be treated with the polypeptide. Such methods are well-known in the art. For example, cells may be engineered by procedures known in the art by use of a retroviral particle containing RNA encoding a polypeptide of the present invention.

Similarly, cells may be engineered in vivo for expression of a polypeptide in vivo by, for example, procedures known in the art. As known in the art, a producer cell for producing a retroviral particle containing RNA encoding a polypeptide of the present invention may be administered to a patient for engineering cells in vivo and expression of the polypeptide in vivo. These and other methods for administering a polypeptide of the present invention by such method should be apparent to those skilled in the art from the teachings of the present invention. For example, the expression vehicle for engineering cells may be other than a retrovirus, for example, an adenovirus which may be used to engineer cells in vivo after combination with a suitable delivery vehicle.

Retroviruses from which the retroviral plasmid vectors hereinabove mentioned may be derived include, but are not limited to, Moloney Murine Leukemia Virus, spleen necrosis virus, retroviruses such as Rous Sarcoma Virus, Harvey Sarcoma Virus, avian leukosis virus, gibbon ape leukemia virus, human immunodeficiency virus, adenovirus, Myeloproliferative Sarcoma Virus, and mammary tumor virus. In one embodiment, the retroviral plasmid vector is derived from Moloney Murine Leukemia Virus.

The vector includes one or more promoters. Suitable promoters which may be employed include, but are not limited to, the retroviral LTR; the SV40 promoter; and the human cytomegalovirus (CMV) promoter described in Miller, et al., *Biotechniques*, Vol. 7, No. 9, 980–990 (1989), or any other promoter (e.g., cellular promoters such as eukaryotic cellular promoters including, but not limited to, the histone, pol III, and -actin promoters). Other viral promoters which may be employed include, but are not limited to, adenovirus promoters, thymidine kinase (TK) promoters, and B19 parvovirus promoters. The selection of a suitable promoter will be apparent to those skilled in the art from the teachings contained herein.

The nucleic acid sequence encoding the polypeptide of the present invention is under the control of a suitable promoter. Suitable promoters which may be employed include, but are not limited to, adenoviral promoters, such as the adenoviral major late promoter; or heterologous promoters, such as the cytomegalovirus (CMV) promoter; the respiratory syncytial virus (RSV) promoter; inducible promoters, such as the MMT promoter, the metallothionein promoter; heat shock promoters; the albumin promoter; the ApoAI promoter; human globin promoters; viral thymidine kinase promoters, such as the Herpes Simplex thymidine kinase promoter; retroviral LTRs (including the modified retroviral LTRs hereinabove described); the -actin promoter; and human growth hormone promoters. The promoter also may be the native promoter which controls the genes encoding the polypeptides.

The retroviral plasmid vector is employed to transduce packaging cell lines to form producer cell lines. Examples of packaging cells which may be transfected include, but are not limited to, the PE501, PA317, -2, -AM, PA12, T19-14X, VT-19-17-H2, CRE, CRIP, GP+E-86, GP+envAm12, and DAN cell lines as described in Miller, *Human Gene Therapy*, Vol. 1, pgs. 5–14 (1990), which is incorporated herein by reference in its entirety. The vector may transduce the packaging cells through any means known in the art. Such means include, but are not limited to, electroporation, the use of liposomes, and $CaPO_4$ precipitation. In one alternative, the retroviral plasmid vector may be encapsulated into a liposome, or coupled to a lipid, and then administered to a host.

The producer cell line generates infectious retroviral vector particles which include the nucleic acid sequence(s) encoding the polypeptides. Such retroviral vector particles then may be employed, to transduce eukaryotic cells, either in vitro or in vivo. The transduced eukaryotic cells will express the nucleic acid sequence(s) encoding the polypeptide. Eukaryotic cells which may be transduced include, but are not limited to, embryonic stem cells, embryonic carcinoma cells, as well as hematopoietic stem cells, hepatocytes, fibroblasts, myoblasts, keratinocytes, endothelial cells, and bronchial epithelial cells.

This invention is also related to the use of a breast specific genes of the present invention as a diagnostic. For example, some diseases result from inherited defective genes. The breast specific genes, CSG7 and CSG10, for example, have been found to have a reduced expression in breast cancer cells as compared to that in normal cells. Further, the remaining breast specific genes of the present invention are overexpressed in breast cancer. Accordingly, a mutation in these genes allows a detection of breast disorders, for example, breast cancer. A mutation in a breast specific gene of the present invention at the DNA level may be detected by a variety of techniques. Nucleic acids used for diagnosis (genomic DNA, mRNA, etc.) may be obtained from a patient's cells, other than from the breast, such as from blood, urine, saliva, tissue biopsy and autopsy material. The genomic DNA may be used directly for detection or may be amplified enzymatically by using PCR (Saiki, et al., *Nature*, 324:163–166 (1986)) prior to analysis. RNA or cDNA may also be used for the same purpose. As an example, PCR primers complementary to the nucleic acid of the instant invention can be used to identify and analyze mutations in a breast specific polynucleotide of the present invention. For example, deletions and insertions can be detected by a change in size of the amplified product in comparison to the normal genotype. Point mutations can be identified by hybridizing amplified DNA to radiolabelled breast specific RNA or, alternatively, radiolabelled antisense DNA sequences.

Another well-established method for screening for mutations in particular segments of DNA after PCR amplification is single-strand conformation polymorphism (SSCP) analysis. PCR products are prepared for SSCP by ten cycles of reamplification to incorporate $^{32}$P-dCTP, digested with an appropriate restriction enzyme to generate 200–300 bp fragments, and denatured by heating to 85 C. for 5 min. and then plunged into ice. Electrophoresis is then carried out in a nondenaturing gel (5% glycerol, 5% acrylamide) (Glavac, D. and Dean, M., Human Mutation, 2:404–414 (1993)).

Sequence differences between the reference gene and "mutants" may be revealed by the direct DNA sequencing method. In addition, cloned DNA segments may be used as probes to detect specific DNA segments. The sensitivity of this method is greatly enhanced when combined with PCR. For example, a sequencing primer is used with double-stranded PCR product or a single-stranded template molecule generated by a modified PCR. The sequence determination is performed by conventional procedures with radiolabeled nucleotides or by automatic sequencing procedures with fluorescent-tags.

Genetic testing based on DNA sequence differences may be achieved by detection of alteration in electrophoretic mobility of DNA fragments and gels with or without denaturing agents. Small sequence deletions and insertions can be visualized by high-resolution gel electrophoresis. DNA fragments of different sequences may be distinguished on denaturing formamide gradient gels in which the mobilities of different DNA fragments are retarded in the gel at different positions according to their specific melting or partial melting temperatures (see, e.g., Myers, et al., *Science*, 230:1242 (1985)). In addition, sequence alterations, in particular small deletions, may be detected as changes in the migration pattern of DNA.

Sequence changes at specific locations may also be revealed by nuclease protection assays, such as Rnase and SI protection or the chemical cleavage method (e.g., Cotton, et al., *PNAS, USA*, 85:4397–4401 (1985)).

Thus, the detection of the specific DNA sequence may be achieved by methods such as hybridization, RNase protection, chemical cleavage, direct DNA sequencing, or the use of restriction enzymes (e.g., Restriction Fragment Length Polymorphisms (RFLP)) and Southern blotting.

The sequences of the present invention are also valuable for chromosome identification. The sequence is specifically targeted to and can hybridize with a particular location on an individual human chromosome. Moreover, there is a current need for identifying particular sites on the chromosome. Few chromosome marking reagents based on actual sequence data (repeat polymorphisms) are presently available for marking chromosomal location. The mapping of DNAs to chromosomes according to the present invention is an important first step in correlating those sequences with genes associated with disease.

Briefly, sequences can be mapped to chromosomes by preparing PCR primers (preferably 15–25 bp) from the cDNA. Computer analysis of the 3' untranslated region is used to rapidly select primers that do not span more than one exon in the genomic DNA, thus complicating the amplification process. These primers are then used for PCR screening of somatic cell hybrids containing individual human chromosomes. Only those hybrids containing the human gene corresponding to the primer will yield an amplified fragment.

PCR mapping of somatic cell hybrids is a rapid procedure for assigning a particular DNA to a particular chromosome. Using the present invention with the same oligonucleotide primers, sublocalization can be achieved with panels of fragments from specific chromosomes or pools of large genomic clones in an analogous manner. Other mapping strategies that can similarly be used to map to its chromosome include in situ hybridization, prescreening with labeled flow-sorted chromosomes and preselection by hybridization to construct chromosome specific-cDNA libraries.

Fluorescence in situ hybridization (FISH) of a cDNA clone to a metaphase chromosomal spread can be used to provide a precise chromosomal location in one step. This technique can be used with cDNA as short as 50 or 60 bases. For a review of this technique, see Verma et al., Human Chromosomes: a Manual of Basic Techniques, Pergamon Press, New York (1988).

Once a sequence has been mapped to a precise chromosomal location, the physical position of the sequence on the chromosome can be correlated with genetic map data. Such data are found, for example, in V. McKusick, Mendelian Inheritance in Man (available on line through Johns Hopkins University Welch Medical Library). The relationship between genes and diseases that have been mapped to the same chromosomal region are then identified through linkage analysis (coinheritance of physically adjacent genes).

Next, it is necessary to determine the differences in the cDNA or genomic sequence between affected and unaffected individuals. If a mutation is observed in some or all of the affected individuals but not in any normal individuals, then the mutation is likely to be the causative agent of the disease.

With current resolution of physical mapping and genetic mapping techniques, a cDNA precisely localized to a chromosomal region associated with the disease could be one of between 50 and 500 potential causative genes. (This assumes 1 megabase mapping resolution and one gene per 20 kb).

The polypeptides, their fragments or other derivatives, or analogs thereof, or cells expressing them can be used as an immunogen to produce antibodies thereto. These antibodies can be, for example, polyclonal or monoclonal antibodies. The present invention also includes chimeric, single chain, and humanized antibodies, as well as Fab fragments, or the product of an Fab expression library. Various procedures known in the art may be used for the production of such antibodies and fragments.

Antibodies generated against the polypeptides corresponding to a sequence of the present invention can be obtained by direct injection of the polypeptides into an animal or by administering the polypeptides to an animal, preferably a nonhuman. The antibody so obtained will then bind the polypeptides itself. In this manner, even a sequence encoding only a fragment of the polypeptides can be used to generate antibodies binding the whole native polypeptides. Such antibodies can then be used to isolate the polypeptide from tissue expressing that polypeptide.

For preparation of monoclonal antibodies, any technique which provides antibodies produced by continuous cell line cultures can be used. Examples include the hybridoma technique (Kohler and Milstein, 1975, *Nature*, 256:495–497), the trioma technique, the human B-cell hybridoma technique (Kozbor et al., 1983, Immunology Today 4:72), and the EBV-hybridoma technique to produce human monoclonal antibodies (Cole, et al., 1985, in Monoclonal Antibodies and Cancer Therapy, Alan R. Liss, Inc., pp. 77–96).

Techniques described for the production of single chain antibodies (U.S. Pat. No. 4,946,778) can be adapted to produce single chain antibodies to immunogenic polypeptide products of this invention. Transgenic mice may also be used to generate antibodies.

The antibodies may also be employed to target breast cancer cells, for example, in a method of homing interaction agents which, when contacting breast cancer cells, destroy them. This is true since the antibodies are specific for the breast specific polypeptides of the present invention. A linking of the interaction agent to the antibody would cause the interaction agent to be carried directly to the breast.

Antibodies of this type may also be used to do in vivo imaging, for example, by labeling the antibodies to facilitate scanning of the pelvic area and the breast. One method for imaging comprises contacting any cancer cells of the breast to be imaged with an anti-breast specific protein-antibody labeled with a detectable marker. The method is performed under conditions such that the labeled antibody binds to the breast specific polypeptides. In a specific example, the antibodies interact with the breast, for example, breast cancer cells, and fluoresce upon contact such that imaging and visibility of the breast are enhanced to allow a determination of the diseased or non-diseased state of the breast.

The present invention will be further described with reference to the following examples; however, it is to be understood that the present invention is not limited to such examples. All parts or amounts, unless otherwise specified, are by weight.

In order to facilitate understanding of the following examples certain frequently occurring methods and/or terms will be described.

"Plasmids" are designated by a lower case p preceded and/or followed by capital letters and/or numbers. The starting plasmids herein are either commercially available, publicly available on an unrestricted basis, or can be constructed from available plasmids in accord with published procedures. In addition, equivalent plasmids to those described are known in the art and will be apparent to the ordinarily skilled artisan.

"Digestion" of DNA refers to catalytic cleavage of the DNA with a restriction enzyme that acts only at certain sequences in the DNA. The various restriction enzymes used herein are commercially available and their reaction conditions, cofactors and other requirements were used as would be known to the ordinarily skilled artisan. For analytical purposes, typically 1 µg of plasmid or DNA fragment is used with about 2 units of enzyme in about 20 µl of buffer solution. For the purpose of isolating DNA fragments for plasmid construction, typically 5 to 50 µg of DNA are digested with 20 to 250 units of enzyme in a larger volume. Appropriate buffers and substrate amounts for particular restriction enzymes are specified by the manufacturer. Incubation times of about 1 hour at 37° C. are ordinarily used, but may vary in accordance with the supplier's instructions. After digestion the reaction is electrophoresed directly on a polyacrylamide gel to isolate the desired fragment.

Size separation of the cleaved fragments is performed using 1 percent TAE agarose gel described by Sambrook, et al., "Molecular Cloning: A Laboratory Manual" Cold Spring Laboratory Press,(1989).

"Oligonucleotides" refers to either a single stranded polydeoxynucleotide or two complementary polydeoxynucleotide strands which may be chemically synthesized. Such synthetic oligonucleotides have no 5' phosphate and thus will not ligate to another oligonucleotide without adding a phosphate with an ATP in the presence of a kinase. A synthetic oligonucleotide will ligate to a fragment that has not been dephosphorylated.

"Ligation" refers to the process of forming phosphodiester bonds between two double stranded nucleic acid fragments (Maniatis, T., et al., Id., p. 146). Unless otherwise provided, ligation may be accomplished using known buffers and conditions with 10 units of T4 DNA ligase ("ligase") per 0.5 µg of approximately equimolar amounts of the DNA fragments to be ligated.

Unless otherwise stated, transformation was performed as described in the method of Graham, F. and Van der Eb, A., Virology, 52:456–457 (1973).

EXAMPLE 1

Determination of Transcription of a breast specific gene

To assess the presence or absence of active transcription of a breast specific gene RNA, approximately 6 ml of venous blood is obtained with a standard venipuncture technique using heparinized tubes. Whole blood is mixed with an equal volume of phosphate buffered saline, which is then layered over 8 ml of Ficoll (Pharmacia, Uppsala, Sweden) in a 15-ml polystyrene tube. The gradient is centrifuged at 1800×g for 20 min at 5 C. The lymphocyte and granulocyte layer (approximately 5 ml) is carefully aspirated and rediluted up to 50 ml with phosphate-buffered saline in a 50-ml tube, which is centrifuged again at 1800×g for 20 min. at 5 C. The supernatant is discarded and the pellet containing nucleated cells is used for RNA extraction using the RNazole B method as described by the manufacturer (Tel-Test Inc., Friendswood, Tex.).

To determine the quantity of mRNA, a probe is designed with an identity to at least a portion of the mRNA sequence transcribed from a human gene whose coding portion includes a DNA sequence of FIGS. 1–20 (SEQ ID NO:1–2, 4, 6, 8–9, 10–24). This probe is mixed with the extracted RNA and the mixed DNA and RNA are precipitated with ethanol −70 C. for 15 minutes). The pellet is resuspended in hybridization buffer and dissolved. The tubes containing the mixture are incubated in a 72 C. water bath for 10–15 mins. to denature the DNA. The tubes are rapidly transferred to a water bath at the desired hybridization temperature. Hybridization temperature depends on the G+C content of the DNA. Hybridization is done for 3 hrs. 0.3 ml of nuclease-S 1 buffer is added and mixed well. 50 1 of 4.0 M ammonium acetate and 0.1 M EDTA is added to stop the reaction. The mixture is extracted with phenol/chloroform and 20 g of carrier tRNA is added and precipitation is done with an equal volume of isopropanol. The precipitate is dissolved in 40 1 of TE (pH 7.4) and run on an alkaline agarose gel. Following electrophoresis, the RNA is microsequenced to confirm the nucleotide sequence. (See Favaloro, J. et al., Methods Enzymol., 65:718 (1980) for a more detailed review).

Two oligonucleotide primers are employed to amplify the sequence isolated by the above methods. The 5 primer is 20 nucleotides long and the 3 primer is a complimentary sequence for the 3 end of the isolated mRNA. The primers are custom designed according to the isolated mRNA. The reverse transcriptase reaction and PCR amplification are performed sequentially without interruption in a Perkin Elmer 9600 PCR machine (Emeryville, Calif.). Four hundred ng total RNA in 20 1 diethylpyrocarbonate treated water are placed in a 65 C. water bath for 5 min. and then quickly chilled on ice immediately prior to the addition of PCR reagents. The 50-1 total PCR volume consisted of 2.5 units Taq polymerase (Perkin-Elmer). 2 units avian myeloblastosis virus reverse transcriptase (Boehringer Mannheim, Indianapolis, Ind.); 200 M each of dCTP, dATP, dGTP and dTTP (Perkin Elmer); 18 pM each primer, 10 mM Tris-HCl; 50 mM KCl; and 2 mM $MgCl_2$ (Perkin Elmer). PCR conditions are as follows: cycle 1 is 42 C. for 15 min then 97 C. for 15 s (1 cycle); cycle 2 is 95 C. for 1 min. 60 C for 1 min, and 72 C. for 30 s (15 cycles); cycle 3 is 95 C for 1 min. 60 C. for 1 min., and 72 C for 1 min. (10 cycles); cycle 4 is 95 C for 1 min., 60 C for 1 min., and 72 C for 2 min. (8 cycles); cycle 5 is 72 C for 15 min. (1 cycle); and the final cycle is a 4 C hold until sample is taken out of the machine. The 50-1 PCR products are concentrated down to 10 1 with vacuum centrifugation, and a sample is then run on a thin 1.2% Tris-borate-EDTA agarose gel containing ethidium bromide. A band of expected size would indicate that this gene is present in the tissue assayed. The amount of RNA in the pellet may be quantified in numerous ways, for example, it may be weighed.

Verification of the nucleotide sequence of the PCR products is done by microsequencing. The PCR product is purified with a Qiagen PCR Product Purification Kit (Qiagen, Chatsworth, Calif.) as described by the manufacturer. One g of the PCR product undergoes PCR sequencing by using the Taq DyeDeoxy Terminator Cycle sequencing kit in a Perkin-Elmer 9600 PCR machine as described by Applied Biosystems (Foster, Calif.). The sequenced product is purified using Centri-Sep columns (Princeton Separations, Adelphia, N.J.) as described by the company. This product is then analyzed with an ABI model 373A DNA sequencing system (Applied Biosystems) integrated with a Macintosh IIci computer.

EXAMPLE 2

Bacterial Expression and Purification of the BSG Proteins and Use For Preparing a Monoclonal Antibody The DNA sequence encoding a polypeptide of the present invention, for this example BSG1, ATCC #97175, is initially amplified using PCR oligonucleotide primers corresponding to the 5' sequences of the protein and the vector sequences 3' to the protein. Additional nucleotides corresponding to the DNA sequence are added to the 5' and 3' sequences respectively. The 5' oligonucleotide primer has the sequence 5' GCCACC<u>ATG</u>GATGTTTTCAAG 3' (SEQ ID NO:25) and contains an NcoI restriction enzyme site followed by 15 nucleotides of coding sequence starting from the initial amino acid of the processed protein. The 3' sequence 5' GCGCAGATCTGTCTCCCCCACTCTGGGC 3' (SEQ ID NO:26) and contains a complementary sequence to a BglII restriction enzyme site and is followed by 18 nucleotides of the nucleic acid sequence encoding the protein. The restriction enzyme sites correspond to the restriction enzyme sites on a bacterial expression vector, pQE-60 (Qiagen, Inc. Chatsworth, Calif.). pQE-60 encodes antibiotic resistance ($Amp^r$), a bacterial origin of replication (ori), an IPTG-regulatable promoter operator (P/O), a ribosome binding site (RBS), a 6-His tag and restriction enzyme sites. pQE-60 is then digested with NcoI and BglII. The amplified sequences are ligated into pQE-60 and inserted in frame with the sequence encoding for the histidine tag and the RBS. The ligation mixture is then used to transform an E. coli strain M15/rep 4 (Qiagen) by the procedure described in Sambrook, J. et al., Molecular Cloning: A Laboratory Manual, Cold Spring Laboratory Press, (1989). M15/rep4 contains multiple copies of the plasmid pREP4, which expresses the lacI repressor and also confers kanamycin resistance ($Kan^r$). Transformants are identified by their ability to grow on LB plates and ampicillin/kanamycin resistant colonies are selected. Plasmid DNA is isolated and confirmed by restriction analysis.

Clones containing the desired constructs are grown overnight (O/N) in liquid culture in LB media supplemented with both Amp (100 ug/ml) and Kan (25 ug/ml). The O/N culture is used to inoculate a large culture at a ratio of 1:100 to 1:250. The cells are grown to an optical density 600 ($O.D.^{600}$) of between 0.4 and 0.6. IPTG ("Isopropyl-B-D-thiogalacto pyranoside") is then added to a final concentration of 1 mM. IPTG induces by inactivating the lacI repressor, clearing the P/O leading to increased gene expression. Cells are grown an extra 3 to 4 hours. Cells are then harvested by centrifugation. The cell pellet is solubilized in the chaotropic agent 6 Molar Guanidine HCl. After clarification, solubilized protein is purified from this solution by chromatography on a Nickel-Chelate column under conditions that allow for tight binding by proteins containing the 6-His tag (Hochuli, E. et al., J. Chromatography 411:177–184 (1984)). BSG1 protein (>90% pure) is eluted from the column in 6 molar guanidine HCl pH 5.0 and for the purpose of renaturation adjusted to 3 molar guanidine HCl, 100 mM sodium phosphate, 10 mmolar glutathione (reduced) and 2 mmolar glutathione (oxidized). After incubation in this solution for 12 hours the protein is dialyzed to 10 mmolar sodium phosphate.

The protein purified in this manner may be used as an epitope to raise monoclonal antibodies specific to such protein. The monoclonal antibodies generated against the polypeptide the isolated protein can be obtained by direct injection of the polypeptides into an animal or by administering the polypeptides to an animal. The antibodies so obtained will then bind to the protein itself. Such antibodies can then be used to isolate the protein from tissue expressing that polypeptide by the use of an, for example, ELISA assay.

EXAMPLE 3

Preparation of cDNA Libraries from Breast Tissue

Total cellular RNA is prepared from tissues by the guanidinium-phenol method as previously described (P. Chomczynski and N. Sacchi, Anal. Biochem., 162: 156–159 (1987)) using RNAzol (Cinna-Biotecx). An additional ethanol precipitation of the RNA is included. Poly A mRNA is isolated from the total RNA using oligo dT-coated latex beads (Qiagen). Two rounds of poly A selection are performed to ensure better separation from non-polyadenylated material when sufficient quantities of total RNA are available.

The mRNA selected on the oligo dT is used for the synthesis of cDNA by a modification of the method of Gobbler and Hoffman (Gobbler, U. and B. J. Hoffman, 1983, Gene, 25:263). The first strand synthesis is performed using either Moloney murine sarcoma virus reverse transcriptase (Stratagene) or Superscript II (RNase H minus Moloney murine reverse transcriptase, Gibco-BRL). First strand synthesis is primed using a primer/linker containing an Xho I restriction site. The nucleotide mix used in the synthesis contains methylated dCTP to prevent restriction within the cDNA sequence. For second-strand synthesis $E.\ coli$ polymerase Klenow fragment is used and [$^{32}$P]-dATP is incorporated as a tracer of nucleotide incorporation.

Following 2nd strand synthesis, the cDNA is made blunt ended using either T4 DNA polymerase or Klenow fragment. Eco RI adapters are added to the cDNA and the cDNA is restricted with Xho I. The cDNA is size fractionated over a Sephacryl S-500 column (Pharmacia) to remove excess linkers and cDNAs under approximately 500 base pairs.

The cDNA is cloned unidirectionally into the Eco RI-Xho I sites of either pBluescript II phagemid or lambda Uni-zap XR (Stratagene). In the case of cloning into pBluescript II, the plasmids are electroporated into $E.\ coli$ SURE competent cells (Stratagene). When the cDNA is cloned into Uni-Zap XR it is packaged using the Gigipack II packaging extract (Stratagene). The packaged phage is used to infect SURE cells and amplified. The pBluescript phagemid containing the cDNA inserts are excised from the lambda Zap phage using the helper phage ExAssist (Stratagene). The rescued phagemid is plated on SOLR $E.\ coli$ cells (Stratagene).

Preparation of Sequencing Templates

Template DNA for sequencing is prepared by 1) a boiling method or 2) PCR amplification.

The boiling method is a modification of the method of Holmes and Quigley (Holmes, D. S. and M. Quigley, 1981, Anal. Biochem., 114:193). Colonies from either cDNA cloned into Bluescript II or rescued Bluescript phagemid are grown in an enriched bacterial media overnight. 400 µl of cells are centrifuged and resuspended in STET (0.1M NaCl, 10 mM TRIS Ph 8.0, 1.0 mM EDTA and 5% Triton X-100) including lysozyme (80 µg/ml) and RNase A (4 µg/ml). Cells are boiled for 40 seconds and centrifuged for 10 minutes. The supernatant is removed and the DNA is precipitated with PEG/NaCl and washed with 70% ethanol (2×). Templates are resuspended in water at approximately 250 ng/µl.

Preparation of templates by PCR is a modification of the method of Rosenthal et al. (Rosenthal, et al., Nucleic Acids Res., 1993, 21:173–174). Colonies containing cDNA cloned into pBluescript II or rescued pBluescript phagemid are grown overnight in LB containing ampicillin in a 96 well tissue culture plate. Two µl of the cultures are used as template in a PCR reaction (Saiki, R K, et al., Science, 239:487–493, 1988; and Saiki, R K, et al., Science, 230: 1350–1354, 1985) using a tricine buffer system (Ponce and Micol., Nucleic Acids Res., 1992, 20: 1992.) and 200 µM dNTPs. The primer set chosen for amplification of the templates is outside of primer sites chosen for sequencing of the templates. The primers used are 5'-ATGCTTCCG-GCTCGTATG-3' (SEQ ID NO:27) which is 5' of the M13 reverse sequence in pBluescript and oligonucleotide probe. To isolate a particular clone, a specific oligonucleotide with 30–40 nucleotides is synthesized using an Applied Biosystems DNA synthesizer according to one of the partial sequences described in this application. The oligonucleotide is labeled with $^{32}$p-ATP using T4 polynucleotide kinase and purified according to the standard protocol (Maniatis et al., Molecular Cloning: A Laboratory Manual, Cold Spring Harbor Press, Cold Spring, N.Y., 1982). The Lambda cDNA library is plated on 1.5% agar plate to a density of 20,000–50,000 pfu/150 mm plate. These plates are screened using Nylon membranes according to the standard phage screening protocol (Stratagene, 1993). Specifically, the Nylon membrane with denatured and fixed phage DNA is prehybridized in 6×SSC, 20 mM NaH$_2$PO$_4$, 0.4% SDS, 5×Denhardt's 500 µg/ml denatured, sonicated salmon sperm DNA; and 6×SSC, 0.1% SDS. After one hour of prehybridization, the membrane is hybridized with hybridization buffer 6×SSC, 20 mM NaH$_2$PO$_4$, 0.4% SDS, 500 µg/ml denatured, sonicated salmon sperm DNA with 1×10$^6$ cpm/ml $^{32}$P-probe overnight at 42 C. The membrane is washed at 45–50 C. with washing buffer 6×SSC, 0.1% SDS for 20–30 minutes dried and exposed to Kodak X-ray film overnight. Positive clones are isolated and purified by secondary and tertiary screening. The purified clone sequenced to verify its identity to the partial sequence described in this application.

An alternative approach to screen the cDNA library prepared from human breast tissue is to prepare a DNA probe corresponding to the entire partial sequence. To prepare a probe, two oligonucleotide primers of 17–20 nucleotides derived from both ends of the partial sequence reported are synthesized and purified. These two oligonucleotides are used to amplify the probe using the cDNA library template. The DNA template is prepared from the phage lysate of the cDNA library according to the standard phage DNA preparation protocol (Maniatis et al.). The polymerase chain reaction is carried out in 25 µl reaction mixture with 0.5 µg of the above cDNA template. The reaction mixture is 1.5–5 mM MgCl$_2$, 0.01% (w/v) gelatin, 20 µM each of dATP, dCTP, dGTP, dTTP, 25 pmol of each primer and 0.25 Unit of Taq polymerase. Thirty five cycles of PCR (denaturation at 94 C for 1 min; annealing at 55 C for 1 min; elongation at 72 C for 1 min) are performed with the Perkin-Elmer Cetus automated thermal cycler. The amplified product is analyzed by agarose gel electrophoresis and the DNA band with expected molecular weight is excised and purified. The PCR product is verified to be the probe by subcloning and sequencing the DNA product. The probe is labeled with the Multiprime DNA Labelling System (Amersham) at a specific activity <1×10$^9$ dmp/µg. This probe is used to screen the lambda cDNA library according to Stratagene's protocol. Hybridization is carried out with 5× TEN 92OXTEN:0.3M Tris-HCl pH 8.0, 0.02M EDTA and 3MNaCl), 5× Denhardt's, 0.5% sodium pyrophosphate, 0.1% SDS, 0.2 mg/ml heat denatured salmon sperm DNA and 1×10$^6$ cpm/ml of [$^{32}$P]-labeled probe at 55 C. for 12 hours. The filters are washed in 0.5× TEN at room temperature for 20–30 min., then at 55 C. for 15 min. The filters are dried and autoradiographed at −70 C. using Kodak XAR-5 film. The positive clones are purified by secondary and tertiary screening. The sequence of the isolated clone are verified by DNA sequencing.

General procedures for obtaining complete sequences from partial sequences described herein are summarized as follows;

Procedure 1

Selected human DNA from the partial sequence clone (the cDNA clone that was sequenced to give the partial sequence) is purified e.g., by endonuclease digestion using Eco-R1, gel electrophoresis, and isolation of the clone by removal from low melting agarose gel. The isolated insert DNA, is radiolabeled e.g., with $^{32}$P labels, preferably by nick translation or random primer labeling. The labeled insert is used as a probe to screen a lambda phage cDNA library or a plasmid cDNA library. Colonies containing clones related to the probe cDNA are identified and purified by known purification methods. The ends of the newly purified clones are nucleotide sequenced to identify full length sequences. Complete sequencing of full length clones is then performed by Exonuclease III digestion or primer walking. Northern blots of the mRNA from various tissues using at least part of the deposited clone from which the partial sequence is obtained as a probe can optionally be performed to check the size of the mRNA against that of the purported full length cDNA.

The following procedures 2 and 3 can be used to obtain full length genes or full length coding portions of genes where a clone isolated from the deposited clone mixture does not contain a full length sequence. A library derived from human breast tissue or from the deposited clone mixture is also applicable to obtaining full length sequences from clones obtained from sources other than the deposited mixture by use of the partial sequences of the present invention.

Procedure 2

RACE Protocol For Recovery of Full-Length Genes

Partial cDNA clones can be made full-length by utilizing the rapid amplification of cDNA ends (RACE) procedure described in Frohman, M. A., Dush, M. K. and Martin, G. R. (1998)Proc. Natl Acad. Sci. USA, 85:8998–9002. A cDNA clone missing either the 5' clone missing either the 5' or 3' end can be reconstructed to include the absent base pairs extending to the translational start or stop codon, respectively. In most cases, cDNAs are missing the start of translation therefor. The following briefly describes a modification of this original 5' RACE procedure. Poly A+ or total RNA is reverse transcribed with Superscript II (Gibco/BRL) and an antisense or complementary primer specific to the cDNA sequence. The primer is removed from the reaction with a Microcon Concentrator (Amicon). The first-strand cDNA is then tailed with dATP and terminal deoxynucleotide transferase (Gibco/BRL). Thus, an anchor sequence is produced which is needed for PCR amplification. The second strand is synthesized from the dA-tail in PCR buffer, Taq DNA polymerase (Perkin-Elmer Cetus), an oligo-dT primer containing three adjacent restriction sites (XhoI, SalI and ClaI) at the 5' end and a primer containing just these restriction sites. This double-stranded cDNA is PCR amplified for 40 cycles with the same primers as well as a nested cDNA-specific antisense primer. The PCR products are size-separated on an ethidium bromide-agarose gel and the region of gel containing cDNA products the predicted size of missing protein-coding DNA is removed. cDNA is purified from the agarose with the Magic PCR Prep kit (Promega), restriction digested with XhoI or SalI, and ligated to a plasmid such as pBluescript SKII (Stratagene) at ShoI and EcoRV sites. This DNA is transformed into bacteria and the plasmid clones sequenced to identify the correct protein-coding inserts. Correct 5' ends are confirmed by comparing this sequence with the putatively identified homologue and overlap with the partial cDNA clone.

Several quality-controlled kits are available for purchase. Similar reagents and methods to those above are supplied in kit form from Gibco/BRL. A second kit is available from Clontech which is a modification of a related technique, SLIC (single-stranded ligation to single-stranded cDNA) developed by Dumas et al. (Dumas, J. B., Edwards, M., Delort, J. and Mallet, Jr., 1991, Nucleic Acids Res., 19:5227–5232). The major differences in procedure are that the RNA is alkaline hydrolyzed after reverse transcription and RNA ligase is used to join a restriction site-containing anchor primer to the first-strand cDNA. This obviates the necessity for the dA-tailing reaction which results in a polyT stretch that is difficult to sequence past.

An alternative to generating 5' cDNA from RNA is to use cDNA library double-stranded DNA. An asymmetric PCR-amplified antisense cDNA strand is synthesized with an antisense cDNA-specific primer and a plasmid-anchored primer. These primers are removed and a symmetric PCR reaction is performed with a nested cDNA-specific antisense primer and the plasmid-anchored primer.

Procedure 3

RNA Ligase Protocol For Generating The 5' End Sequences To Obtain Full Length Genes Once a gene of interest is identified, several methods are available for the identification of the 5' or 3' portions of the gene which may not be present in the original deposited clone. These methods include but are not limited to filter probing, clone enrichment using specific probes and protocols similar and identical to 5' and 3' RACE. While the full length gene may be present in a library and can be identified by probing, a useful method for generating the 5' end is to use the existing sequence information from the original partial sequence to generate the missing information. A method similar to 5' RACE is available for generating the missing 5' end of a desired full-length gene. (This method was published by Fromont-Racine et al, Nucleic Acids Res., 21(7):1683–1684 (1993). Briefly, a specific RNA oligonucleotide is ligated to the 5' ends of a population of RNA presumably containing full-length gene RNA transcript and a primer set containing a primer specific to the ligated RNA oligonucleotide. A primer specific to a known sequence (EST) of the gene of interest is used to PCR amplify the 5' portion of the desired full length gene which may then be sequenced and used to generate the full length gene. This method starts with total RNA isolated from the desired source, poly A RNA may be used but is not a prerequisite for this procedure. The RNA preparation may then be treated with phosphatase if necessary to eliminate 5' phosphate groups on degraded or damaged RNA which may interfere with the later RNA ligase step. The phosphatase if used is then inactivated and the RNA is treated with tobacco acid pyrophosphatase in order to remove the cap structure present at the 5' ends of messenger RNAs. This reaction leaves a 5' phosphate group at the 5' end of the cap-cleaved RNA which can then be ligated to an RNA oligonucleotide using T4 RNA ligase. This modified RNA preparation can then be used as a template for first strand cDNA synthesis using a gene-specific oligonucleotide. The first stand synthesis reaction can then be used as a template for PCR amplification of the desired 5' end using a primer specific to the ligated RNA oligonucleotide and a primer specific to the known sequence (EST) of the gene of interest. The resultant product is then sequenced and analyzed to confirm that the 5' end sequence belongs to the partial sequence.

EXAMPLE 5

Cloning and expression of BSG1 using the baculovirus expression system

The DNA sequence encoding the full length BSG1 protein, ATCC#97175, was amplified using PCR oligonucleotide primers corresponding to the 5' and 3' sequences of the gene:

The 5' primer has the sequence 5' AAAGGATC-CCCCGCCATC<u>ATG</u>GATGTTTTCAAGAAG 3' (SEQ ID NO:29) and contains a BamHI restriction enzyme site (in bold) followed by 8 nucleotides resembling an efficient signal for the initiation of translation in eukaryotic cells (Kozak, M., J. Mol. Biol., 196:947–950 (1987) of the BSG1 gene (the initiation codon for translation "ATG" is underlined).

The 3' primer has the sequence 5' AAATCTAGAC-TAGTCTCCCCCACTCTG 3' (SEQ ID NO:30) and contains the cleavage site for the restriction endonuclease XbaI and 21 nucleotides complementary to the 3' sequence of the BSG1 gene. The amplified sequences were isolated from a 1% agarose gel using a commercially available kit ("Geneclean," BIO 101 Inc., La Jolla, Calif.). The fragment was then digested with the endonucleases BamHI and XbaI and then purified again on a 1% agarose gel. This fragment is designated F2.

The vector pA2 (modification of pVL941 vector, discussed below) is used for the expression of the BSG1 protein using the baculovirus expression system (for review see: Summers, M. D. and Smith, G. E. 1987, A manual of methods for baculovirus vectors and insect cell culture procedures, Texas Agricultural Experimental Station Bulletin No. 1555). This expression vector contains the strong polyhedrin promoter of the Autographa californica nuclear polyhedrosis virus (AcMNPV) followed by the recognition sites for the restriction endonucleases BamHI and XbaI. The polyadenylation site of the simian virus (SV)40 is used for efficient polyadenylation. For an easy selection of recombinant virus the beta-galactosidase gene from *E. coli* is inserted in the same orientation as the polyhedrin promoter followed by the polyadenylation signal of the polyhedrin gene. The polyhedrin sequences are flanked at both sides by viral sequences for the cell-mediated homologous recombination of co-transfected wild-type viral DNA. Many other baculovirus vectors could be used in place of pA2 such as pRG1, pAc373, pVL941 and pAcIM1 (Luckow, V. A. and Summers, M. D., Virology, 170:31–39).

The plasmid was digested with the restriction enzymes BamHI and XbaI and dephosphorylated using calf intestinal phosphatase by procedures known in the art. The DNA was then isolated from a 1% agarose gel using the commercially available kit ("Geneclean" BIO 101 Inc., La Jolla, Calif.). This vector DNA is designated V2.

Fragment F2 and the dephosphorylated plasmid pA2 were ligated with T4 DNA ligase. *E. coli* HB101 cells were then transformed and bacteria identified that contained the plasmid (pBacBSG1) with the BSG1 gene using the enzymes BamHI and XbaI. The sequence of the cloned fragment was confirmed by DNA sequencing.

5 µg of the plasmid pBacBSG1 was co-transfected with 1.0 µg of a commercially available linearized baculovirus ("BaculoGold™ baculovirus DNA", Pharmingen, San Diego, Calif.) using the lipofection method (Felgner et al. Proc. Natl . Acad. Sci. USA, 84:7413–7417 (1987)).

1 µg of BaculoGold™ virus DNA and 5 µg of the plasmid pBacBSG1 were mixed in a sterile well of a microtiter plate containing 50/µl of serum free Grace's medium (Life Technologies Inc., Gaithersburg, Md.). Afterwards 10 µl Lipofectin plus 90 µl Grace's medium were added, mixed and incubated for 15 minutes at room temperature. Then the transfection mixture was added drop-wise to the Sf9 insect cells (ATCC CRL 1711) seeded in a 35 mm tissue culture plate with 1 ml Grace's medium without serum. The plate was rocked back and forth to mix the newly added solution. The plate was then incubated for 5 hours at 27 C. After 5 hours the transfection solution was removed from the plate and 1 ml of Grace's insect medium supplemented with 10% fetal calf serum was added. The plate was put back into an incubator and cultivation continued at 27 C. for four days.

After four days the supernatant was collected and a plaque assay performed similar as described by Summers and Smith (supra). As a modification an agarose gel with "Blue Gal" (Life Technologies Inc., Gaithersburg) was used which allows an easy isolation of blue stained plaques. (A detailed description of a "plaque assay" can also be found in the user's guide for insect cell culture and baculovirology distributed by Life Technologies Inc., Gaithersburg, page 9–10).

Four days after the serial dilution, the virus was added to the cells and blue stained plaques were picked with the tip of an Eppendorf pipette. The agar containing the recombinant viruses was then resuspended in an Eppendorf tube containing 200 µl of Grace's medium. The agar was removed by a brief centrifugation and the supernatant containing the recombinant baculovirus was used to infect Sf9 cells seeded in 35 mm dishes. Four days later the supernatants of these culture dishes were harvested and then stored at 4 C.

Sf9 cells were grown in Grace's medium supplemented with 10% heat-inactivated FBS. The cells were infected with the recombinant baculovirus V-BSG1 at a multiplicity of infection (MOI) of 2. Six hours later the medium was removed and replaced with SF900 II medium minus methionine and cysteine (Life Technologies Inc., Gaithersburg). 42 hours later 5 µCi of $^{35}$S-methionine and 5 µCi $^{35}$S cysteine (Amersham) were added. The cells were further incubated for 16 hours before they were harvested by centrifugation and the labelled proteins visualized by SDS-PAGE and autoradiography.

EXAMPLE 6

Expression of Recombinant BSG1 in COS cells

The expression of plasmid, BSG1 HA is derived from a vector pcDNAI/Amp (Invitrogen) containing:1) SV40 origin of replication, 2) ampicillin resistance gene, 3) *E. coli* replication origin, 4) CMV promoter followed by a polylinker region, an SV40 intron and polyadenylation site. A DNA fragment encoding the entire precursor and a HA tag fused in frame to its 3' end was cloned into the polylinker region of the vector, therefore, the recombinant protein expression is directed under the CMV promoter. The HA tag corresponds to an epitope derived from the influenza hemagglutinin protein as previously described (I. Wilson, H. Niman, R. Heighten, A Cherenson, M. Connolly, and R. Lerner, 1984, Cell 37:767, (1984)). The infusion of HA tag to the target protein allows easy detection of the recombinant protein with an antibody that recognizes the HA epitope.

The plasmid construction strategy is described as follows:

The DNA sequence encoding BSG1, ATCC #97175, was constructed by PCR using two primers: the 5' primer AAAGGATCCCCCGCCATC ATGGATGTTTTCAAGAAG 3' (SEQ ID NO:29) contains a BamHI site followed by 18 nucleotides of BSG1 coding sequence starting from the initiation codon; the 3' sequence AAATCTAGACTAAAGCGTAGTCTGG-GACGTCGTATGGGTACTCCTGGGGTCTC CCCCACTCTGGGG 3' (SEQ ID NO:31) contains complementary sequences to an XbaI site, translation stop codon, HA tag and the last 18 nucleotides of the BamHI coding sequence (not including the stop codon). Therefore, the PCR product contains an BamHI site, BSG1 coding sequence followed by HA tag fused in frame, a translation termination stop codon next to the HA tag, and an XbaI site. The PCR amplified DNA fragment and the vector, pcDNAI/Amp, were digested with BamHI and XbaI restriction enzyme and ligated. The ligation mixture was transformed into E. coli strain SURE (available from Stratagene Cloning Systems, 11099 North Torrey Pines Road, La Jolla, Calif. 92037) the transformed culture was plated on ampicillin media plates and resistant colonies were selected. Plasmid DNA was isolated from transformants and examined by restriction analysis for the presence of the correct fragment. For expression of the recombinant BSG protein, COS cells were transfected with the expression vector by DEAE-DEXTRAN method (J. Sambrook, E. Fritsch, T. Maniatis, Molecular Cloning: A Laboratory Manual, Cold Spring Laboratory Press, (1989)). The expression of the BSG HA protein was detected by radiolabelling and immunoprecipitation method (E. Harlow, D. Lane, Antibodies: A Laboratory Manual, Cold Spring Harbor Laboratory Press, (1988)). Cells were labelled for 8 hours with $^{35}$S-cysteine two days post transfection. Culture media was then collected and cells were lysed with detergent (RIPA buffer (150 mM NaCl, 1% NP-40, 0.1% SDS, 1% NP-40, 0.5% DOC, 50 mM Tris, pH 7.5) (Wilson, I. et al., Id. 37:767 (1984)). Both cell lysate and culture media were precipitated with an HA specific monoclonal antibody. Proteins precipitated were analyzed on 15% SDS-PAGE gels.

Numerous modifications and variations of the present invention are possible in light of the above teachings and, therefore, within the scope of the appended claims, the invention may be practiced otherwise than as particularly described.

What is claimed is:

1. An isolated antibody or fragment thereof that specifically binds to a protein whose amino acid sequence consists of the amino acid sequence of the BSG1 polypeptide encoded by the BSG1 cDNA contained in ATCC Deposit No. 97175, wherein said protein is overexpressed in breast cancer.

2. The antibody or fragment thereof of claim 1 wherein said protein bound by said antibody or fragment thereof is glycosylated.

3. The antibody or fragment thereof of claim 1 wherein said antibody or fragment thereof is polyclonal.

4. The antibody or fragment thereof of claim 1 wherein said antibody or fragment thereof is monoclonal.

5. The antibody or fragment thereof of claim 1 which is selected from the group consisting of:
   (a) a single chain antibody; and
   (b) a Fab fragment.

6. The antibody or fragment thereof of claim 1 which is labeled.

7. The antibody or fragment thereof of claim 1 wherein said antibody or fragment thereof specifically binds to said protein in a Western blot or an ELISA.

8. An isolated cell that produces the antibody or fragment thereof of claim 1.

9. A hybridoma that produces the antibody or fragment thereof of claim 1.

10. A method of detecting a BSG1 protein consisting of SEQ ID NO:33 in a biological sample comprising:
    (a) contacting the biological sample with the antibody or fragment thereof of claim 1; and
    (b) detecting the BSG1 protein in the biological sample.

11. An isolated antibody or fragment thereof that specifically binds a BSG1 protein purified from a cell culture wherein said protein is encoded by a the BSG1 cDNA contained ATCC Deposit No. 97175.

12. The antibody or fragment thereof of claim 11 wherein said antibody or fragment thereof is monoclonal.

13. The antibody or fragment thereof of claim 11 wherein said antibody or fragment thereof is polyclonal.

14. The antibody or fragment thereof of claim 11 which is selected from the group consisting of:
    (a) a single chain antibody; and
    (b) a Fab fragment.

15. The antibody or fragment thereof of claim 11 wherein said antibody or fragment thereof specifically binds to said protein in a Western blot or an ELISA.

16. The antibody or fragment thereof of claim 11 wherein the amino acid sequence of said protein consists of the mature polypeptide encoded by the BSG1 cDNA contained in ATCC Deposit No. 97175.

* * * * *